(12) United States Patent
Nakao et al.

(10) Patent No.: US 8,149,236 B2
(45) Date of Patent: Apr. 3, 2012

(54) INFORMATION PROCESSING APPARATUS AND PROGRAM

(75) Inventors: Megumi Nakao, Nara (JP); Kotaro Minato, Nara (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 1073 days.

(21) Appl. No.: 11/989,768

(22) PCT Filed: Jul. 18, 2006

(86) PCT No.: PCT/JP2006/314148
§ 371 (c)(1),
(2), (4) Date: Jan. 31, 2008

(87) PCT Pub. No.: WO2007/015365
PCT Pub. Date: Feb. 8, 2007

(65) Prior Publication Data
US 2010/0149174 A1  Jun. 17, 2010

(30) Foreign Application Priority Data

Aug. 1, 2005 (JP) ................................. 2005-222477
Sep. 6, 2005 (JP) ................................. 2005-257415

(51) Int. Cl.
*G06T 15/00* (2011.01)

(52) U.S. Cl. ............ 345/423; 345/419; 345/422; 703/2; 703/6; 703/11; 382/173; 434/268; 434/270

(58) Field of Classification Search .................. 345/419, 345/422, 423, 581, 589, 619; 703/2, 6, 11; 382/173; 434/268, 270
See application file for complete search history.

(56) References Cited

U.S. PATENT DOCUMENTS
5,768,413 A * 6/1998 Levin et al. ................... 382/173
(Continued)

FOREIGN PATENT DOCUMENTS
JP          54-135548 A    10/1979
(Continued)

OTHER PUBLICATIONS

Toriwaki et al., "Visualization of the Human Body toward the Navigation Diagnosis with the Virtualized Human Body", Journal of Visualization, vol. 1, No. 1, pp. 111-124, 1998.

(Continued)

*Primary Examiner* — Phu Nguyen
(74) *Attorney, Agent, or Firm* — Rader, Fishman & Grauer PLLC

(57) ABSTRACT

Conventional information processing apparatuses have the problem of not being able to easily extract and observe a three-dimensional region of interest from 3D voxel data. The present invention provides an information processing apparatus in which a first slice information group, which is multiple pieces of slice information obtained as a result of extraction from 3D voxel information using a first three-dimensional region mask extracting the 3D voxel information, is stored, wherein the information processing apparatus: receives input regarding a second three-dimensional region mask; acquires second mesh information constituting the second three-dimensional region mask; determines an internal region, which is a region inside the second mesh information, and an external region, which is a region outside the second mesh information, for each slice information in the first slice information group, based on the second mesh information; and outputs the first slice information group such that the internal region and the external region are visually distinguished from each other. With this information processing apparatus, it is possible to easily extract and observe a three-dimensional region of interest from 3D voxel data.

5 Claims, 79 Drawing Sheets

U.S. PATENT DOCUMENTS

| | | | |
|---|---|---|---|
| 7,191,110 B1 * | 3/2007 | Charbel et al. | 703/11 |
| 7,739,090 B2 * | 6/2010 | Charbel et al. | 703/11 |

FOREIGN PATENT DOCUMENTS

| | | | |
|---|---|---|---|
| JP | 01-209583 A | 8/1989 | |
| JP | 11-272157 A | 10/1999 | |
| JP | 2000-222601 A | 8/2000 | |
| JP | 2002-329216 A | 11/2002 | |
| JP | 2003-44869 A | 2/2003 | |
| JP | 2003-91735 A | 3/2003 | |
| JP | 2003-141566 A | 5/2003 | |
| JP | 2004-133550 A | 4/2004 | |
| JP | 2004-215916 A | 8/2004 | |
| WO | WO-2006/013813 A1 | 2/2006 | |

OTHER PUBLICATIONS

B. Pflesser et al., "Planning and Rehearsal of Surgical Interventions in the Volume Model", Proc. Medicine Meets Virtual Reality Conference, pp. 259-264, 2000.

A. Kaufman et al., "Volume Graphics", IEEE Computer, vol. 26, No. 7, pp. 51-64, 1993.

W. Chen et al., "Real-time Ray Casting Rendering of Volume Clipping in Medical Visualization", Journal of Computer Science and Technology, vol. 18, Issue 6, pp. 804-814, 2003.

B. Cabral et al., "Accelerated Volume Rendering and Tomographic Reconstruction Using Texture Mapping Hardware", Proc. Symposium on Volume Visualization '94, pp. 91-98, 1994.

U. Kuhnapfel et al., "Endoscopic Surgery Training Using Virtual Reality and Deformable Tissue Simulation", Computers & Graphics (Elsevier Science), vol. 24, No. 5, p. 671-682, 2000.

Yamamoto et al., "Palpation Simulator of Beating Aorta for Cardiovascular Surgery Training", IEEJ Trans. SM, vol. 123, No. 3, pp. 85-91, 2003.

Nakao et al., "Volumetric Mask and its Real-time Processing for Volume Interaction", TVRSJ, vol. 10, No. 4, pp. 591-598, 2005.

Megumi Nakao et al., "Butsuri Tokusei ni Motoduita Koseisai Katsu Taiwateki na Nansoshiki Sekkai Shuho", Transactions of Information Processing Society of Japan, vol. 44, No. 8, pp. 2255-2265, 2003.

M. Nakao et al., Evaluation and User Study of Haptic Simulator for Learning Palpation in Cardiovascular Surgery, International Conference of Artificial Reality and Tele-Existence (ICAT), pp. 203-208, 2003.

Yoshihiro Kuroda et al., "Fukusu Zokikan no Sesshoku Simulation o Jitsugen Suru Densei Taikan no Sogo Sayo Model", Transaction of the Virtual Reality Society of Japan, vol. 8, No. 2, pp. 155-162, 2003.

Nakao et al., "ActiveHeart System: Proposal and implemtation of a graphic and haptic simulation of heart beats", pp. 97-104; URL—http://www.interaction-ipsj.org/archives/paper2001/pdf2001/nakao.pdf.

Office Action from Japanese Patent Office for application No. 2007-529203 dated Sep. 2, 2011.

* cited by examiner

FIG.6

$(x_1, y_1, z_1, col_1, e_1), (x_2, y_2, z_2, col_2, e_2), \text{---}$ $\text{---}, (x_n, y_n, z_n, col_n, e_n)$

FIG.7

| point identifier | positional information |
|---|---|
| A | $(x_1, y_1, z_1)$ |
| B | $(x_2, y_2, z_2)$ |
| C | $(x_3, y_3, z_3)$ |
| 0 | $(x_4, y_4, z_4)$ |
| ┊ | ┊ |

FIG.10

| point identifier | positional information |
|---|---|
| A′ | ( $x'_1$, $y'_1$, $z'_1$ ) |
| B′ | ( $x'_2$, $y'_2$, $z'_2$ ) |
| C′ | ( $x'_3$, $y'_3$, $z'_3$ ) |
| O′ | ( $x'_4$, $y'_4$, $z'_4$ ) |
| ⋮ | ⋮ | input menu for elasticity information

FIG.24
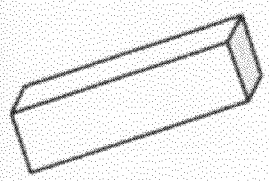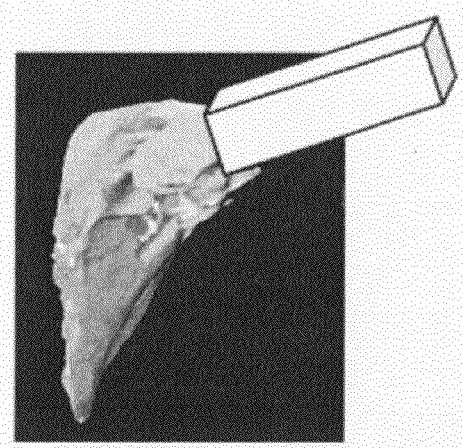

FIG.39

| point identifier | positional information |
|---|---|
| A | $(x_1, y_1, z_1)$ |
| B | $(x_2, y_2, z_2)$ |
| C | $(x_3, y_3, z_3)$ |
| 0 | $(x_4, y_4, z_4)$ |
| ⋮ | ⋮ |

FIG.40

$(x_1, y_1, z_1, col_1), (x_2, y_2, z_2, col_2),$ -----------

----------------------------------------

----------------------------------------

----------------------------------------

-------------------------, $(x_n, y_n, z_n, col_n)$

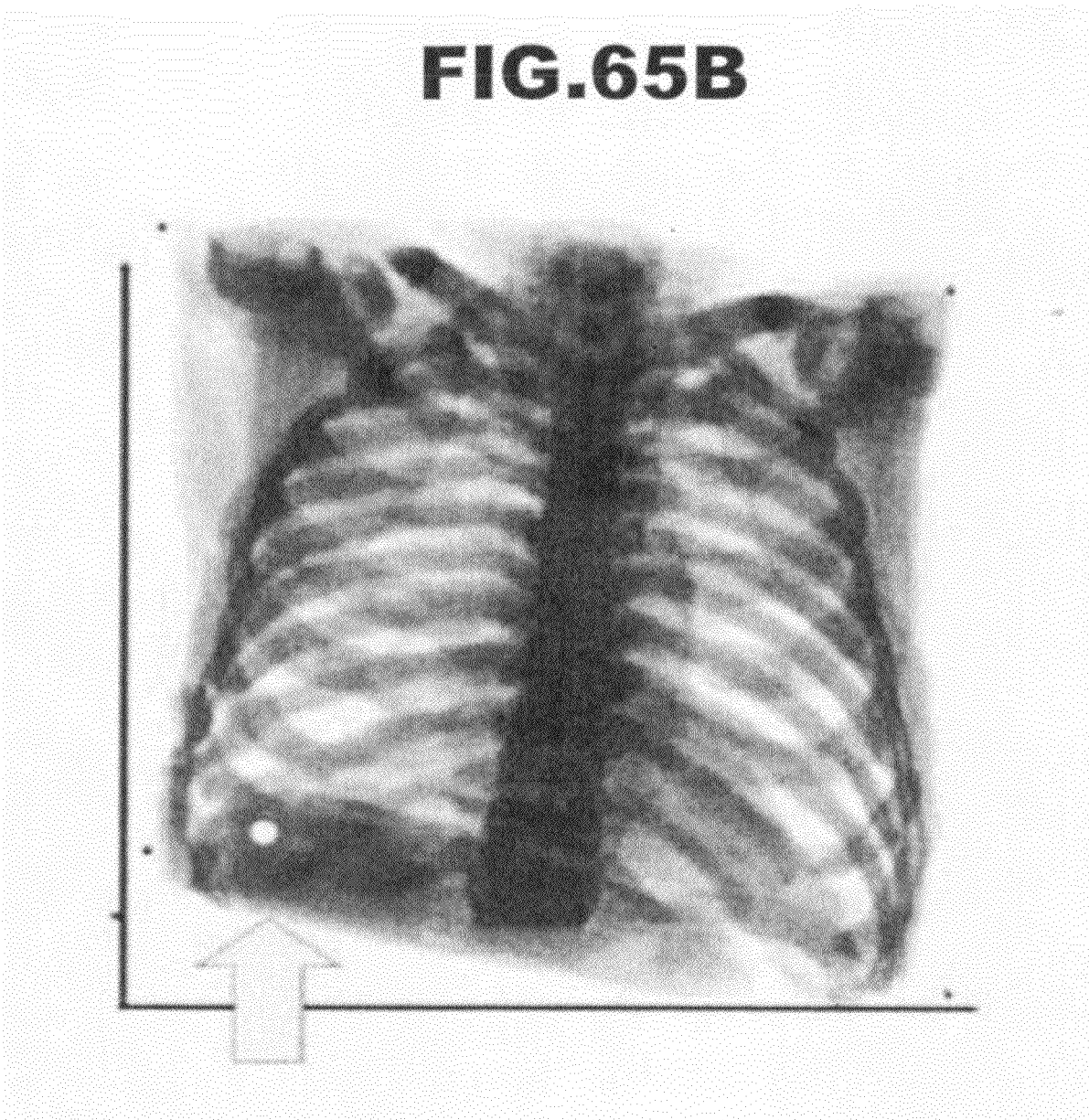

INFORMATION PROCESSING APPARATUS AND PROGRAM

TECHNICAL FIELD

The present invention relates to information processing apparatuses and the like for outputting three-dimensional objects and manipulating three-dimensional objects.

BACKGROUND ART

In the medical field, for example, medical image software or visualization systems using computer graphics or image processing techniques are extensively used. In computer-aided diagnoses or preoperative planning, an environment is necessary in which a region of interest on a medical image can be flexibly and interactively referred to (see Non-Patent Documents 1 and 2, for example).

Herein, a collection of two-dimensional images acquired by CT or MRI is volume data constituted by a huge number of voxels. In order to provide intuitive understanding of a complex three-dimensional structure inside the human body, it is necessary to render the structure together with its interior.

In conventional information processing apparatuses for this request, typically, a three-dimensionally reconstructed image using display of sliced tomographic images or volume rendering is used in preoperative planning or intraoperative navigation (see Non-Patent Documents 3 and 4, for example). Furthermore, clipping expression at an arbitrary plane on a reconstructed image is extensively used for observing the interior of an organ (see Non-Patent Document 5, for example).

Furthermore, as a conventional information processing apparatus, there is an interactive system such as a VR surgical simulator. This interactive system uses polygons in order to define a three-dimensional geometric shape (see Non-Patent Document 6, for example).

Herein, as an input/output device relating to this information processing apparatus, there is PHANToM. PHANToM is an input/output device for receiving input of positional data, giving feedback to a computer, and generating a force vector and driving a motor (see Non-Patent Document 7, for example).

Furthermore, as a technique relating to the present invention, there are an algorithm for calculating deformation (Non-Patent Document 8, for example) and an algorithm for rendering (Non-Patent Document 9, for example).

Also, recently, radiotherapy is attracting attention as a method for effectively treating cancer. However, there is the problem that if an affected area moves due to breathing as in the case of lung tumors, an efficient treatment is difficult. Currently, countermeasures are taken such as setting a wide irradiation area, or implementing a marker in the vicinity of a tumor and irradiating this position in synchronization with breathing. In a radiotherapy apparatus that is currently under development, an accelerator tube for generating radiation includes a gimbal function, and thus a head can be freely swung. There is a demand for a treatment in which a tumor is irradiated with radiation while being tracked using these characteristics.

[Non-Patent Document 1] J. Toriwaki and one other, "Visualization of the Human Body toward the Navigation Diagnosis with the Virtualized Human Body", Journal of Visualization, 1998, Vol. 1, No. 1, pp. 111-124.

[Non-Patent Document 2] B. Pflesser and three others, "Planning and Rehearsal of Surgical Interventions in the Volume Model", Proc. Medicine Meets Virtual Reality Conference, 2000, pp. 259-264.

[Non-Patent Document 3] A. Kaufman and two others, "Volume Graphics", IEEE Computer, 1993, Vol. 26, No. 7, pp. 51-64.

[Non-Patent Document 4] W. Chen and two others, "Real-time Ray Casting Rendering of Volume Clipping in Medical Visualization", Journal of Computer Science and Technique, 2003, Vol. 18, Issue 6, pp. 804-814.

[Non-Patent Document 5] B. Cabral and two others, "Accelerated Volume Rendering and Tomographic Reconstruction Using Texture Mapping Hardware", Proc. Symposium on Volume Visualization '94, 1994, pp. 91-98.

[Non-Patent Document 6] U. Kuhnapfel and two others, "Endoscopic Surgery Training Using Virtual Reality and Deformable Tissue Simulation", Computers & Graphics (Elsevier Science), 2000, Vol. 24, No. 5, pp. 671-682.

[Non-Patent Document 7] Website, the Internet <URL: http://www.nissho-ele.co.jp/3d/3Dmodeling/phamtom03.htm>

[Non-Patent Document 8] Yasuhiro Yamamoto et al., "Palpation Simulator of Beating Aorta for Cardiovascular Surgery Training", Journal of the Institute of Electrical Engineers of Japan, 2003, Vol. 123-E, No. 3, pp. 85-92.

[Non-Patent Document 9] Megumi Nakao and two others, "Volumetric Mask and its Real-time Processing for Volume Interaction", Journal of the Virtual Reality Society of Japan, 2005, Vol. 10, No. 4, pp. 591-598.

DISCLOSURE OF INVENTION

Problems to be Solved by the Invention

However, the above-described conventional techniques have the problem that information relating to the elasticity of a three-dimensional object cannot be expressed. More specifically, for example, in a surgical simulation, a surgeon using the information processing apparatus cannot obtain a feel of putting a scalpel into the human trunk, which is a three-dimensional object, and thus surgical simulation cannot be sufficiently performed in the above-described conventional techniques.

Furthermore, in the above-described conventional techniques, for example, deformation of an organ caused in a case where the organ is held or pinched with surgical instruments cannot be simulated.

Furthermore, the conventional techniques according to Non-Patent Documents 1 to 5 have the problem that a three-dimensional region of interest cannot be extracted and observed with an interactive and simple manipulation. Accordingly, for example, an observation focusing on a specific organ among portions constituting the human body cannot be performed.

Also, in the conventional technique according to Non-Patent Document 6, a segmentation process that typically takes considerable effort is necessary in order to define a complex three-dimensional shape of an organ. Accordingly, a three-dimensional region of interest cannot be easily extracted and observed. Moreover, at the time of surface generation from a medical image, color information on the inside of an organ may be lost, or shapes important for a diagnosis may not be reflected. Since the data is used for a diagnosis or preoperative planning, a change or information loss of the data has to be avoided. Herein, the segmentation process refers to a process in which a collection of medical images is divided into units such as organs, by adding anatomical information thereto.

It is also an object of the present invention to realize tracking irradiation of a moving object, by performing a simulation to estimate movement of a lung tumor due to breathing, in order to perform the above-described treatment in which a tumor is irradiated with radiation while being tracked. The simulation result is displayed as a DRR (digitally reconstructed radiograph). The DRR is obtained, for example, by reconstructing a direct radiograph based on CT data of a patient, and is mainly used for treatment planning and the like. It is an object of the present invention to construct an environment in which a surgeon compares DRRs and time-series direct radiographs obtained in the treatment, confirms the validity of the simulation, and then performs irradiation.

Mean for Solving the Problems

A first aspect of the present invention is directed to an information processing apparatus, comprising: a slice information group storage portion in which a slice information group having multiple pieces of slice information is stored, the slice information being information constituted based on two-dimensional image data obtained as a result of extraction with multiple planes from 3D voxel information, which is volume texture of a three-dimensional object, and being constituted by information of multiple points having positional information, which is information indicating position, and elasticity information, which is information of elasticity; a slice information group output portion that outputs the slice information group; an instruction receiving portion that receives an instruction for a given point or region in the slice information group that has been output; a positional information acquiring portion that acquirers at least one piece of positional information of the point, or a point constituting the region, corresponding to the instruction; an elasticity information acquiring portion that acquires at least one piece of elasticity information paired with the at least one piece of positional information that has been acquired by the positional information acquiring portion; and an elasticity information output portion that performs output based on the at least one piece of elasticity information that has been acquired by the elasticity information acquiring portion.

With this configuration, it is possible to handle information relating to the elasticity of a three-dimensional object.

Furthermore, a second aspect of the present invention is directed to an information processing apparatus, comprising: an object information storage portion in which 3D voxel information, which is volume texture of a three-dimensional object, is stored; a slice information group storage portion in which a slice information group having multiple pieces of slice information is stored, the slice information being information constituted based on two-dimensional image data obtained as a result of extraction with multiple planes from the 3D voxel information, and being constituted by information of multiple points having positional information, which is information indicating position, and color information, which is information of color; a first mesh information storage portion in which first mesh information, which is three-dimensional mesh information of the three-dimensional object, is stored; a slice information group output portion that outputs the slice information group; an instruction receiving portion that receives an instruction for a given point or region in the slice information group that has been output; a second mesh information acquiring portion that deforms the first mesh information based on the instruction, thereby acquiring second mesh information constituting the deformed shape; a first slice information group acquiring portion that acquires a first slice information group, which is multiple pieces of slice information that do not have color information, based on the second mesh information; a color information determining portion that determines color information of each point that is contained in the multiple pieces of slice information constituting the first slice information group, and that corresponds to a point in the 3D voxel information; a second slice information group acquiring portion that sets new color information for each point in the first slice information group that has been acquired by the first slice information group acquiring portion, based on the color information of each point that has been determined by the color information determining portion, thereby acquiring a second slice information group; and a deformed object output portion that outputs the second slice information group.

With this configuration, it is possible to easily understand shape deformation of a three-dimensional object.

Furthermore, a third aspect of the present invention is directed to the information processing apparatus according to the second aspect, wherein the slice information is constituted by information of multiple points having positional information, color information, and elasticity information, and the information processing apparatus further comprises: a positional information acquiring portion that acquirers at least one piece of positional information of the point, or a point constituting the region, corresponding to the instruction; an elasticity information acquiring portion that acquires at least one piece of elasticity information paired with the at least one piece of positional information that has been acquired by the positional information acquiring portion; and an elasticity information output portion that performs output based on the at least one piece of elasticity information that has been acquired by the elasticity information acquiring portion.

With this configuration, it is possible to handle information relating to the elasticity of a three-dimensional object, and to understand shape deformation.

Furthermore, a fourth aspect of the present invention is directed to the information processing apparatus according to the first aspect, further comprising: an object information storage portion in which 3D voxel information, which is volume texture of a three-dimensional object, is stored; and a slice information group acquiring portion that extracts multiple pieces of slice information perpendicular to a line of sight and sliced at constant intervals, from the 3D voxel information stored in the object information storage portion, thereby acquiring a slice information group, wherein the slice information group in the slice information group storage portion is the slice information group that has been acquired by the slice information group acquiring portion.

With this configuration, it is possible to handle information relating to the elasticity of a three-dimensional object, and it is not necessary to prepare a slice information group in advance.

Furthermore, a fifth aspect of the present invention is directed to an information processing apparatus, comprising: an object information storage portion in which 3D voxel information, which is volume texture of a three-dimensional object, is stored; a slice information group storage portion in which a slice information group having multiple pieces of slice information is stored, the slice information being information constituted based on two-dimensional image data obtained as a result of extraction with multiple planes from the 3D voxel information, and being constituted by information of multiple points having positional information, which is information indicating position, and color information, which is information of color; a first mesh information storage portion in which first mesh information, which is three-dimensional mesh information of the three-dimensional object, is stored; a slice information group output portion that outputs the slice information group; an instruction receiving portion that receives an instruction for a given region in the slice information group that has been output; a second mesh information acquiring portion that deforms the first mesh information based on the instruction, thereby acquiring second mesh information constituting the deformed shape; a first slice information group acquiring portion that acquires a first slice information group, which is multiple pieces of slice information that do not have color information, based on the second mesh information; a color information determining portion that determines color information of each point that is contained in the multiple pieces of slice information constituting the first slice information group, and that corresponds to a point in the 3D voxel information; a second slice information group acquiring portion that sets new color information for each point in the first slice information group that has been acquired by the first slice information group acquiring portion, using the color information of each point that has been determined by the color information determining portion, thereby acquiring a second slice information group; and a deformed object output portion that outputs the second slice information group.

With this configuration, it is possible to receive an instruction for a region in an organ, to receive information regarding movement of the region, and to output the deformation result. Accordingly, it is possible to assist surgical planning.

Furthermore, a sixth aspect of the present invention is directed to the information processing apparatus according to the fifth aspect, wherein the first mesh information has a manipulation node, which is a point that is displaced according to the instruction that has been received by the instruction receiving portion, a free node, which is a point that is displaceable according to the displacement of the manipulation node, and a fixed node, which is a point that is not displaced, and the second mesh information acquiring portion acquires second mesh information by displacing the manipulation node according to the instruction, displacing the free node according to the displacement of the manipulation node, and not displacing the fixed node.

With this configuration, it is possible for the user to input an instruction to deform a given region, and to understand shape deformation of the three-dimensional object corresponding to the instruction.

Furthermore, a seventh aspect of the present invention is directed to the information processing apparatus according to the sixth aspect, wherein the second mesh information acquiring portion comprises a manipulation node determining unit that determines a manipulation node according to the instruction.

With this configuration, in a case where an instruction is given for a given region, it is possible to easily specify points (nodes) corresponding to the region.

Furthermore, an eighth aspect of the present invention is directed to the information processing apparatus according to the sixth aspect, wherein the instruction that has been received by the instruction receiving portion is an instruction to rotate and/or translate the region, and the second mesh information acquiring portion comprises a displacement determining unit that determines the displacement of the manipulation node according to the instruction.

With this configuration, it is possible to understand shape deformation of a three-dimensional object in the case of pinching or twisting the three-dimensional object.

Furthermore, a ninth aspect of the present invention is directed to the information processing apparatus according to the fifth aspect, further comprising: a surgical instrument metaphor storage portion in which a surgical instrument metaphor, which is a metaphor of a surgical instrument, is stored; and a surgical instrument metaphor output portion that outputs the surgical instrument metaphor, wherein the instruction receiving portion receives an instruction regarding movement or manipulation of the surgical instrument metaphor, and the instruction serves as an instruction for a given region in the slice information group that has been output.

With this configuration, it is possible to simulate deformation of an organ using a surgical instrument, on the information processing apparatus.

Furthermore, a tenth aspect of the present invention is directed to the information processing apparatus according to the fifth aspect, further comprising: a positional information acquiring portion that acquires multiple pieces of positional information of points constituting a region corresponding to the instruction; an elasticity information acquiring portion that acquires multiple pieces of elasticity information paired with the multiple pieces of positional information that have been acquired by the positional information acquiring portion; and an elasticity information output portion that performs output using the multiple pieces of elasticity information that have been acquired by the elasticity information acquiring portion.

With this configuration, it is possible for the user to understand shape deformation of a three-dimensional object in the case of pinching or twisting the three-dimensional object, while feeling the elasticity of the three-dimensional object.

Furthermore, an eleventh aspect of the present invention is directed to the information processing apparatus according to the first aspect, further comprising an input/output portion that inputs an instruction for a given point or region in the slice information group that has been output, and receives output of the elasticity information output portion and outputs a force corresponding to the output.

With this configuration, it is possible for the user to feel the elasticity of a three-dimensional object, using excellent input means such as PHANToM.

Furthermore, a twelfth aspect of the present invention is directed to an information processing apparatus, comprising: a slice information group storage portion in which a slice information group having multiple pieces of slice information is stored, the slice information being information constituted based on image data on a plane obtained as a result of extraction from 3D voxel information, which is volume texture of a three-dimensional object, and being constituted by information of multiple points having positional information, which is information indicating position; an input receiving portion that receives input regarding a three-dimensional region mask having a three-dimensional geometric shape, and input regarding elasticity information, which is information of elasticity; a mesh information acquiring portion that acquires mesh information, which is three-dimensional mesh information constituting the three-dimensional region mask; and an elasticity information setting portion that sets elasticity information based on the input that has been received by the input receiving portion, for each point that is contained in each slice information of the slice information group, and that is contained in an internal region, which is a region inside the mesh information, based on the mesh information.

With this configuration, it is possible to easily set elasticity information.

Furthermore, a thirteenth aspect of the present invention is directed to the information processing apparatus according to the first aspect, wherein the information of the points contained in the slice information has color information, which is information of color.

With this configuration, it is possible to further handle color information. Thus, in a case where the information processing apparatus is used as a simulation apparatus, it is possible to simulate deformation and the like of a three-dimensional object that is similar to the real material.

Furthermore, a fourteenth aspect of the present invention is directed to the information processing apparatus according to the twelfth aspect, wherein the shape of the three-dimensional region mask is generally in the shape of an organ.

With this configuration, for example, it is possible to easily set elasticity information for each organ.

A fifteenth aspect of the present invention is directed to an information processing apparatus, comprising: an object information storage portion in which 3D voxel information, which is volume texture of a three-dimensional object, is stored; a first slice information group storage portion in which a first slice information group is stored, the first slice information group being multiple pieces of slice information obtained as a result of extraction from the 3D voxel information using a first three-dimensional region mask, which is a three-dimensional region mask extracting the 3D voxel information and having a three-dimensional geometric shape; an input receiving portion that receives input regarding a second three-dimensional region mask, which is a three-dimensional region mask at the second order; a second mesh information acquiring portion that acquires second mesh information, which is three-dimensional mesh information constituting the second three-dimensional region mask; and an object output portion that determines an internal region, which is a region inside the second mesh information, and an external region, which is a region outside the second mesh information, for each slice information in the first slice information group, based on the second mesh information, acquires a second slice information group in which the internal region and the external region are visually distinguished from each other, and outputs the second slice information group.

With this configuration, for example, it is possible to extract and observe a three-dimensional region of interest such that the three-dimensional region of interest is distinguished from the other regions in 3D voxel data, which is volume texture of a three-dimensional object acquired by MRI, CT, or the like.

Furthermore, a sixteenth aspect of the present invention is directed to the information processing apparatus according to the fifteenth aspect, wherein the object output portion comprises: a second slice information group constituting unit that sets a transparent color for points in the external region in each slice information in the first slice information group, thereby constituting a second slice information group; an output unit that outputs the second slice information group that has been constituted by the second slice information group constituting unit.

With this configuration, for example, it is possible to extract and observe only a three-dimensional region of interest from 3D voxel data, which is volume texture of a three-dimensional object acquired by MRI, CT, or the like.

Furthermore, a seventeenth aspect of the present invention is directed to the information processing apparatus according to the fifteenth aspect, wherein the object output portion comprises: a second slice information group constituting unit that sets different color tones for the color of points in the internal region in each slice information in the first slice information group and the color of points in the external region in each slice information in the first slice information group, thereby constituting a second slice information group; and an output unit that outputs the second slice information group that has been constituted by the second slice information group constituting unit.

With this configuration, for example, it is possible to extract and observe a three-dimensional region of interest such that the three-dimensional region of interest is distinguished from the other regions in 3D voxel data, which is volume texture of a three-dimensional object acquired by MRI, CT, or the like.

Furthermore, an eighteenth aspect of the present invention is directed to the information processing apparatus according to the seventeenth aspect, wherein the second slice information group constituting unit sets the brightness of the points in the internal region in each slice information in the first slice information group to be greater than the brightness of the points in the external region in each slice information in the first slice information group, thereby constituting a second slice information group.

With this configuration, for example, it is possible to easily observe a three-dimensional region of interest, by focusing the region of interest in 3D voxel data, which is volume texture of a three-dimensional object acquired by MRI, CT, or the like.

Furthermore, a nineteenth aspect of the present invention is directed to the information processing apparatus according to the fifteenth aspect, wherein the object output portion comprises: a second slice information group constituting unit that sets a transparent color for points in the internal region in each slice information in the first slice information group, thereby constituting a second slice information group; and an output unit that outputs the second slice information group that has been constituted by the second slice information group constituting unit.

With this configuration, for example, it is possible to extract and observe the remaining portions from which a three-dimensional figure has been removed in 3D voxel data, which is volume texture of a three-dimensional object acquired by MRI, CT, or the like. Accordingly, for example, it is possible to confirm in advance a state in which a hole has been made with a drill or the like in surgeries. Thus, this information processing apparatus is effective for surgical simulation, preoperative planning, and the like.

Furthermore, a twentieth aspect of the present invention is directed to the information processing apparatus according to the fifteenth aspect, wherein the input receiving portion receives input regarding at least two second three-dimensional region masks, the second mesh information acquiring portion acquires at least two pieces of second mesh information constituting the at least two second three-dimensional region masks, and the object output portion divides each slice information in the first slice information group into multiple regions according to the at least two pieces of second mesh information, and outputs the first slice information group such that the multiple regions are visually distinguished from each other.

With this configuration, for example, it is possible to extract and observe multiple three-dimensional regions of interest such that the three-dimensional regions of interest are distinguished from the other regions in 3D voxel data, which is volume texture of a three-dimensional object acquired by MRI, CT, or the like.

Furthermore, a twenty-first aspect of the present invention is directed to the information processing apparatus according to the twentieth aspect, wherein colors corresponding to the at least two second three-dimensional region masks are present, and the object output portion comprises: a second slice information group constituting unit that determines color of points in each of the regions, based on the color corresponding to the at least one second three-dimensional region mask constituting each of the regions, constitutes multiple pieces of slice information, which is a collection of points having the color, and acquires a second slice information group, which is the multiple pieces of slice information; and an output unit that outputs the second slice information group that has been constituted by the second slice information group constituting unit.

With this configuration, for example, it is possible to easily extract and observe multiple three-dimensional regions of interest such that the three-dimensional regions of interest are distinguished from the other regions in 3D voxel data, which is volume texture of a three-dimensional object acquired by MRI, CT, or the like.

Furthermore, a twenty-second aspect of the present invention is directed to the information processing apparatus according to any one of the fifteenth to twenty-first aspects, wherein the shape of a three-dimensional object corresponding to an instruction received by the input receiving portion is generally in the shape of an organ.

With this configuration, it is possible to extract and observe only an organ of interest.

Furthermore, a twenty-third aspect of the present invention is directed to the information processing apparatus according to any one of the fifteenth to twenty-second aspects, wherein the input receiving portion receives a shape change instruction, which is an instruction to change the shape of the second three-dimensional region mask, and the information processing apparatus further comprises a three-dimensional region mask shape changing portion that changes the shape of the second three-dimensional region mask based on the shape change instruction.

With this configuration, for example, it is possible to interactively change the shape of a three-dimensional region of interest, and to extract and observe the three-dimensional region of interest such that the three-dimensional region of interest is distinguished from the other regions, in 3D voxel data, which is volume texture of a three-dimensional object acquired by MRI, CT, or the like.

Furthermore, a twenty-fourth aspect of the present invention is directed to the information processing apparatus according to any one of the fifteenth to twenty-third aspects, wherein the input receiving portion receives a position change instruction, which is an instruction to change the position of the second three-dimensional region mask, and the information processing apparatus further comprises a three-dimensional region mask position changing portion that changes the position of the second three-dimensional region mask based on the position change instruction.

With this configuration, for example, it is possible to interactively change the position of a three-dimensional region of interest, and to extract and observe the three-dimensional region of interest such that the three-dimensional region of interest is distinguished from the other regions, in 3D voxel data, which is volume texture of a three-dimensional object acquired by MRI, CT, or the like.

Furthermore, a twenty-fifth aspect of the present invention is directed to the information processing apparatus according to any one of the fifteenth to twenty-fourth aspects, further comprising a first slice information group acquiring portion that extracts multiple pieces of slice information perpendicular to a line of sight and sliced at constant intervals, from the 3D voxel information stored in the object information storage portion, thereby acquiring a first slice information group, and the first slice information group in the first slice information group storage portion is the first slice information group that has been acquired by the first slice information group acquiring portion.

With this configuration, it is possible to allow even thinned slice information to be viewed in three dimensions by the user viewing a collection of the slice information. Moreover, it is possible to increase the speed of display processing, because slice information that has been thinned out at predetermined intervals is acquired. Moreover, it is possible to display a high-quality three-dimensional object, because slice information is acquired at constant intervals.

A twenty-sixth aspect of the present invention is directed to an information processing apparatus, comprising: a first slice information group storage portion in which at least two pieces of first slice information are stored, the first slice information being slice information, and having arrangement information, which is information relating to arrangement; an origin information storage portion in which origin information, which is information indicating the position of an origin of X-ray irradiation, is stored; a second slice information group acquiring portion that performs extraction from each of the at least two pieces of first slice information, perpendicularly to each of the multiple pieces of slice information and radially from the position indicated by the origin information, using arrangement information of each of the multiple pieces of slice information, thereby acquiring multiple pieces of second slice information; a magnification calculating portion that calculates, for each of the multiple pieces of second slice information, a magnification that is an enlargement ratio or reduction ratio of each second slice information, using arrangement information of the second slice information; a third slice information group acquiring portion that enlarges or reduces each of the multiple pieces of second slice information according to the magnification that has been calculated by the magnification calculating portion, thereby acquiring multiple pieces of third slice information; and an output portion that outputs the multiple pieces of third slice information in a superimposed manner.

With this configuration, it is possible to generate a DRR (digitally reconstructed radiograph).

Furthermore, a twenty-seventh aspect of the present invention is directed to the information processing apparatus according to the twenty-sixth aspect, further comprising: an object information storage portion in which 3D voxel information, which is volume texture of a three-dimensional object, is stored; and a first slice information group acquiring portion extracts and acquires multiple pieces of first slice information perpendicular to a line of sight and sliced at constant intervals, from the 3D voxel information stored in the object information storage portion, wherein the at least two pieces of first slice information in the first slice information group storage portion are the first slice information that has been acquired by the first slice information group acquiring portion.

With this configuration, for example, it is possible to generate a DRR from CT data or the like.

Furthermore, a twenty-eighth aspect of the present invention is directed to the information processing apparatus according to the twenty-seventh aspect, further comprising a receiving portion that receives a line-of-sight vector specifying the line of sight, and the first slice information group acquiring portion extracts and acquires multiple pieces of first slice information perpendicular to the line of sight indicated by the line-of-sight vector and sliced at constant intervals, from the 3D voxel information stored in the object information storage portion.

With this configuration, it is possible to generate DRRs at various angles.

Furthermore, a twenty-ninth aspect of the present invention is directed to the information processing apparatus according to the twenty-sixth aspect, wherein the first slice information, the second slice information, and the third slice information have transparency information, which is information of the transparency of a point constituting each slice information, the information processing apparatus further comprises a receiving portion that receives the transparency information, and the transparency of the multiple pieces of third slice information that are output in a superimposed manner changes according to the transparency information that has been received by the receiving portion.

With this configuration, it is possible to generate DRRs with various transparencies.

Furthermore, a thirtieth aspect of the present invention is directed to the information processing apparatus according to the twenty-sixth aspect, wherein each of the at least two pieces of first slice information is an image including the chest.

With this configuration, it is possible to acquire a DRR of the chest.

Effect of the Invention

With an information processing apparatus according to the present invention, it is possible to output a three-dimensional object and to manipulate a three-dimensional object.

Furthermore, with another information processing apparatus according to the present invention, for example, it is possible to easily extract and output a three-dimensional region of interest from 3D voxel data, which is volume texture of a three-dimensional object acquired by MRI, CT, or the like.

Furthermore, with another information processing apparatus according to the present invention, for example, it is possible to acquire a DRR from volume texture of a three-dimensional object acquired by MRI, CT, or the like.

BEST MODE FOR CARRYING OUT THE INVENTION

Hereinafter, embodiments of an information processing apparatus and the like will be described with reference to the drawings. It should be noted that components denoted by the same reference numerals in the embodiments perform similar operations, and thus a description thereof may not be repeated.

Embodiment 1

FIG. 1 is a block diagram of an information processing apparatus in this embodiment.

The information processing apparatus includes an input/output device 101, an instruction receiving portion 102, an object information storage portion 103, a first mesh information storage portion 104, a slice information group acquiring portion 105, a slice information group storage portion 106, a slice information group output portion 107, a second mesh information acquiring portion 108, a first slice information group acquiring portion 109, a color information determining portion 110, a second slice information group acquiring portion 111, a deformed object output portion 112, a positional information acquiring portion 113, an elasticity information acquiring portion 114, and an elasticity information output portion 115. The color information determining portion 110 includes a corresponding point determining unit 1101 and a color information determining unit 1102.

The input/output device 101 inputs an instruction for a given point or region in a slice information group that has been output, and receives output of the elasticity information output portion 115 and outputs a force vector corresponding to the output. It is possible "to output a corresponding force vector", for example, by driving a motor. The input/output device 101 is, for example, PHANToM, vibrating an input device, or the like. Herein, if output is output on a screen, the input/output device 101 is a mouse and a display, for example. The input/output device 101 may be constituted by two or more devices. Furthermore, the input/output device 101 may be considered to be included, or not to be included, in the information processing apparatus. In the block diagram in FIG. 1, the information processing apparatus includes the input/output device 101. The instruction for a region is, for example, an instruction for a region including multiple points (nodes), using a surgical instrument metaphor representing an image of a surgical instrument, which is an instrument for surgeries. The surgical instrument metaphor may be image data having a pattern of scissors or tweezers used in surgeries, or may be graphic data or three-dimensional image data having the shape of a rectangular parallelepiped or sphere, for example.

The instruction receiving portion 102 receives an instruction for a given point or region in the slice information group that has been output. Furthermore, the instruction receiving portion 102 receives an instruction to output the slice information group, or a rotation instruction, which is an instruction to rotate the slice information group (three-dimensional object) that has been output, for example. Means for inputting an instruction and the like for a given point or region may be any means, such as PHANTOM, a mouse, a keyboard, or a menu screen. An instruction for a point or region and an output instruction may be input from different input means. The instruction receiving portion 102 can be implemented, for example, as a device driver for input means such as PHANToM or a keyboard, or control software for a menu screen. Herein, an instruction for a point or region is typically an instruction using PHANToM and is an instruction to press a point or region. In response to such a pressing instruction, the PHANToM outputs a force corresponding to the elasticity, and a user can feel the elasticity by feeling this force.

In the object information storage portion 103, 3D voxel information, which is volume texture of a three-dimensional object, is stored. The 3D voxel information is, for example, a collection of two-dimensional images acquired by CT, MRI, PET, or other medical devices. The 3D voxel information is, for example, a collection of two-dimensional images of the inside of the human brain or body captured by CT or MRI. The 3D voxel information is, for example, information of a point constituted by (x, y, z, col, modulus of elasticity). Herein, (x, y, z) of (x, y, z, col, modulus of elasticity) represents coordinate information in a three-dimensional space, "col" represents color information of this point, and "modulus of elasticity" represents a value indicating the elasticity of this point and is an example of elasticity information. The information of the point may contain transparency information, which is information of transparency such as an alpha value. The 3D voxel information herein is preferably information of points packed without spacing therebetween, but also may be information of discrete points. Herein, the 3D voxel information may be (x, y, z, col), and the elasticity information may be held as additional information to the 3D voxel information. Also in this case, the 3D voxel information may be considered to have the elasticity information. The object information storage portion 103 is preferably a non-volatile storage medium, but can be implemented also as a volatile storage medium. Furthermore, examples of the elasticity information include Young's modulus, Poisson's ratio, break value, and coefficient of friction.

In the first mesh information storage portion 104, first mesh information, which is three-dimensional mesh information of a three-dimensional object, is stored. The first mesh information is three-dimensional mesh information. The three-dimensional mesh information is a collection of information of points constituting a three-dimensional object. The three-dimensional mesh information is a collection of information of discrete points. The information of the points herein is typically information having the data structure (x, y, z, col, elasticity information). Note that the information of the points may contain only the coordinate information (x, y, z). The first mesh information storage portion 104 is preferably a non-volatile storage medium, but can be implemented also as a volatile storage medium.

The slice information group acquiring portion 105 extracts multiple pieces of slice information perpendicular to a line of sight and sliced at constant intervals, from the 3D voxel information stored in the object information storage portion 103, thereby acquiring a slice information group, and at least temporarily stores the slice information group in the slice information group storage portion 106. The phrase "perpendicular to a line of sight" refers to a state of being perpendicular to a line-of-sight vector, which is a vector perpendicular to a screen on which a three-dimensional object is displayed. Herein, the slice information is a collection of information of points constituting a plane, and, typically, the points are packed without spacing therebetween. Typically, the slice information group acquiring portion 105 can be implemented, for example, as an MPU or a memory. Typically, the processing procedure of the slice information group acquiring portion 105 is implemented by software, and the software is stored in a storage medium such as a ROM. Note that the processing procedure also may be implemented by hardware (dedicated circuit).

In the slice information group storage portion 106, a slice information group having multiple pieces of slice information is stored, the slice information being information constituted based on two-dimensional image data obtained as a result of extraction with multiple planes from 3D voxel information, which is volume texture of a three-dimensional object, and being constituted by information of multiple points having positional information, which is information indicating position. Herein, the slice information group in the slice information group storage portion 106 may be prepared in advance. In this case, in the information processing apparatus, the slice information group acquiring portion 105 is not necessary. Furthermore, the points constituting the slice information may have elasticity information, which is information of elasticity, and color information. The slice information group storage portion 106 may be a non-volatile storage medium, or may be a volatile storage medium.

The slice information group output portion 107 outputs the slice information group in the slice information group storage portion 106. Herein, the term "output" has a concept that includes, for example, displaying on a display screen, printing in a printer, and transmission to an external apparatus (typically, an apparatus having a display device). The slice information group output portion 107 may be considered to include, or not to include, an output device such as a display.

The slice information group output portion 107 can be implemented, for example, as driver software for an output device, or a combination of driver software for an output device and the output device. Herein, in a case where the slice information group is output to a display screen, usually, a user can recognize a three-dimensional object.

The second mesh information acquiring portion 108 deforms the first mesh information in the first mesh information storage portion 104 according to the instruction that has been received by the instruction receiving portion 102, thereby acquiring second mesh information constituting the deformed shape. The data structure of the second mesh information is typically the same as that of the first mesh information. Herein, the second mesh information acquiring portion 108 deforms the first mesh information, thereby acquiring second mesh information constituting the deformed shape. The processing in which the second mesh information acquiring portion 108 deforms the first mesh information, thereby acquiring second mesh information constituting the deformed shape is typically processing using the finite element method. Typically, the second mesh information acquiring portion 108 can be implemented, for example, as an MPU or a memory. Typically, the processing procedure of the second mesh information acquiring portion 108 is implemented by software, and the software is stored in a storage medium such as a ROM. Note that the processing procedure also may be implemented by hardware (dedicated circuit).

The first slice information group acquiring portion 109 acquires a first slice information group, which is multiple pieces of slice information that do not have color information, based on the second mesh information that has been acquired by the second mesh information acquiring portion 108. The first slice information group acquiring portion 109 acquires multiple pieces of slice information, which is information acquired by slicing a three-dimensional object constituted by the second mesh information, which is mesh information obtained by deforming the first mesh information. The intervals between the pieces of slice information are preferably constant. Furthermore, multiple pieces of slice information are preferably perpendicular to the line-of-sight vector. Furthermore, the phrase "slice information constituting the first slice information group does not have color information" also refers to a state in which the slice information has color information of a dummy color, which is not displayed in a final state. Typically, the first slice information group acquiring portion 109 can be implemented, for example, as an MPU or a memory. Typically, the processing procedure of the first slice information group acquiring portion 109 is implemented by software, and the software is stored in a storage medium such as a ROM. Note that the processing procedure also may be implemented by hardware (dedicated circuit).

The color information determining portion 110 determines color information of each point that is contained in the multiple pieces of slice information constituting the first slice information group, and that corresponds to a point in the 3D voxel information stored in the object information storage portion 103. Each point corresponding to a point in the 3D voxel information is a point contained in the 3D voxel information, and is a point before deformation. Typically, the color information determining portion 110 can be implemented, for example, as an MPU or a memory. Typically, the processing procedure of the color information determining portion 110 is implemented by software, and the software is stored in a storage medium such as a ROM. Note that the processing procedure also may be implemented by hardware (dedicated circuit).

The corresponding point determining unit 1101 determines each point that corresponds to each point in multiple pieces of slice information constituting the first slice information group, and that is contained in the 3D voxel information. Herein, each point contained in the 3D voxel information is a point before deformation. Typically, the corresponding point determining unit 1101 can be implemented, for example, as an MPU or a memory. Typically, the processing procedure of the corresponding point determining unit 1101 is implemented by software, and the software is stored in a storage medium such as a ROM. Note that the processing procedure also may be implemented by hardware (dedicated circuit).

The color information determining unit 1102 acquires color information of each point in the 3D voxel information determined by the corresponding point determining unit 1101. Typically, the color information determining unit 1102 can be implemented, for example, as an MPU or a memory. Typically, the processing procedure of the color information determining unit 1102 is implemented by software, and the software is stored in a storage medium such as a ROM. Note that the processing procedure also may be implemented by hardware (dedicated circuit).

The second slice information group acquiring portion 111 sets new color information for each point in the first slice information group that has been acquired by the first slice information group acquiring portion 109, based on the color information of each point that has been determined by the color information determining portion 110, thereby acquiring a second slice information group. More specifically, the second slice information group acquiring portion 111 sets, as new color information, the color information of each point that has been determined by the color information determining portion 110, for each point in the first slice information group that has been acquired by the first slice information group acquiring portion 109. Multiple pieces of slice information for which such color information is set is the second slice information group. Typically, the second slice information group acquiring portion 111 can be implemented, for example, as an MPU or a memory. Typically, the processing procedure of the second slice information group acquiring portion 111 is implemented by software, and the software is stored in a storage medium such as a ROM. Note that the processing procedure also may be implemented by hardware (dedicated circuit).

The deformed object output portion 112 outputs the second slice information group that has been acquired by the second slice information group acquiring portion 111. The term "output" has a concept that includes, for example, displaying on a display screen, printing in a printer, transmission to an external apparatus (such as an apparatus provided with a display device), and accumulation in a storage medium. The term "display" refers to output, for example, to a display screen or a projector. The second slice information group may be displayed in any form. The deformed object output portion 112 preferably outputs multiple slices constituting the second slice information group, sequentially from a slice positioned deeper with respect to the depth of the display screen. The deformed object output portion 112 may be considered to include, or not to include, an output device such as a display. The deformed object output portion 112 can be implemented, for example, as driver software for an output device, or a combination of driver software for an output device and the output device.

The positional information acquiring portion 113 acquires one or more pieces of positional information of the point, or a point constituting the region, corresponding to the instruction. The positional information is typically a collection of the coordinate information (x, y, z). The positional information acquiring portion 113 may acquire the one or more pieces of positional information, from the slice information group, from the first slice information group, or from the second slice information group. Typically, the positional information acquiring portion 113 can be implemented, for example, as an MPU or a memory. Typically, the processing procedure of the positional information acquiring portion 113 is implemented by software, and the software is stored in a storage medium such as a ROM. Note that the processing procedure also may be implemented by hardware (dedicated circuit).

The elasticity information acquiring portion 114 acquires one or more pieces of elasticity information paired with the one or more pieces of positional information that have been acquired by the positional information acquiring portion 113. It is necessary that a point whose elasticity information is acquired by the elasticity information acquiring portion 114 is the same as a point whose positional information is acquired by the positional information acquiring portion 113. Typically, the elasticity information acquiring portion 114 can be implemented, for example, as an MPU or a memory. Typically, the processing procedure of the elasticity information acquiring portion 114 is implemented by software, and the software is stored in a storage medium such as a ROM. Note that the processing procedure also may be implemented by hardware (dedicated circuit).

The elasticity information output portion 115 outputs information of a force (such as a force vector), based on the one or more pieces of elasticity information that have been acquired by the elasticity information acquiring portion 114. The term "output" has a concept that includes, for example, transmission of a signal to the input/output device 101 such as PHANToM, displaying on a display screen, printing in a printer, outputting a sound, and transmission to an external apparatus. The phrase "outputting a sound" herein is, for example, output expressing a force as the strength of a sound. The elasticity information output portion 115 can be implemented, for example, as software, driver software for an output device such as a display or a loudspeaker, or a combination of driver software for an output device and the output device.

Next, the operation of the information processing apparatus will be described with reference to the flowcharts in FIGS. 2 to 4.

(Step S201) The instruction receiving portion 102 judges whether or not an instruction from the input/output device 101 (may be a keyboard, a mouse, or the like) has been received. If the instruction has been received, the procedure proceeds to step S202. If the instruction has not been received, the procedure returns to step S201.

(Step S202) The instruction receiving portion 102 judges whether or not the instruction that has been received in step S201 is an instruction to output a slice information group. If it is the output instruction, the procedure proceeds to step S203. If it is not the output instruction, the procedure proceeds to step S205.

(Step S203) The slice information group output portion 107 reads a slice information group from the slice information group storage portion 106. Each slice information constituting the slice information group is typically perpendicular to a line-of-sight vector.

(Step S204) The slice information group output portion 107 outputs the slice information group that has been read in step S203. The procedure returns to step S201. Herein, with the output of the slice information group, a three-dimensional object is displayed.

(Step S205) The instruction receiving portion 102 judges whether or not the instruction that has been received in step S201 is an instruction to rotate a three-dimensional object. If it is the rotation instruction, the procedure proceeds to step S206. If it is not the rotation instruction, the procedure proceeds to step S209.

(Step S206) The slice information group acquiring portion 105 acquires a line-of-sight vector, based on the rotation instruction that has been received in step S201. The line-of-sight vector is a vector that is perpendicular to a display screen of a display. The rotation instruction is input from the input/output device 101 such as a mouse. The processing of rotating a three-dimensional object with a mouse is a well known technique, and thus a detailed description thereof has been omitted.

(Step S207) The slice information group acquiring portion 105 extracts multiple pieces of slice information perpendicular to the line-of-sight vector and sliced at constant intervals, from the 3D voxel information stored in the object information storage portion 103, thereby acquiring a slice information group. It is assumed that the interval value is stored in advance.

(Step S208) The slice information group acquiring portion 105 at least temporarily accumulates the slice information group that has been acquired in step S207, in the slice information group storage portion 106. The procedure proceeds to step S204.

(Step S209) The instruction receiving portion 102 judges whether or not the instruction that has been received in step S201 is an instruction for a point or region. If it is the instruction for a point or region, the procedure proceeds to step S210. If it is not the instruction for a point or region, the procedure returns to step S201. Herein, a method for giving the instruction for a point or region may be any method, such as a method using a mouse.

(Step S210) The positional information acquiring portion 113 acquires one or more pieces of positional information of the point, or a point constituting the region, corresponding to the instruction that has been received in step S201.

(Step S211) The elasticity information acquiring portion 114 acquires one or more pieces of elasticity information paired with the one or more pieces of positional information that have been acquired by the positional information acquiring portion 113, from each slice information in the slice information group storage portion 106 or the 3D voxel information in the object information storage portion 103. First, the elasticity information acquiring portion 114 searches for a point having the one or more pieces of positional information, from each slice information or the 3D voxel information. Next, the elasticity information of the point obtained by the search is acquired.

(Step S212) The elasticity information output portion 115 arithmetically calculates elasticity information that is to be output, from the one or more pieces of elasticity information that have been acquired by the elasticity information acquiring portion 114. The elasticity information that is acquired by the elasticity information output portion 115 may be different from the elasticity information that is to be output thereby. For example, the elasticity information that is acquired may be modulus of elasticity, and the elasticity information that is to be output may be a force. Furthermore, the elasticity information is, for example, modulus of elasticity. The modulus of elasticity may be Young's modulus, volume modulus of elasticity, modulus of rigidity, or Poisson's ratio. In this case, the elasticity information output portion 115 may calculates the average value of the one or more pieces of elasticity information, and take the obtained value as the elasticity information that is to be output. Furthermore, for example, the elasticity information output portion 115 may take the maximum value of the one or more pieces of elasticity information, as the elasticity information that is to be output. Furthermore, for example, the elasticity information output portion 115 may take the minimum value of the one or more pieces of elasticity information, as the elasticity information that is to be output. Alternatively, the elasticity information output portion 115 may calculate the elasticity information that is to be output, with a predetermined function $f(f(e_1, e_2, \ldots, e_n))$ using one or more pieces of elasticity information $(e_1, e_2, \ldots, e_n)$ as parameters.

(Step S213) The elasticity information output portion 115 outputs the one or more pieces of elasticity information that have been acquired in step S212, to the input/output device 101 (typically, PHANToM).

(Step S214) The input/output device 101 vibrates with drive of a motor. With this processing, the elasticity is transmitted to the user.

(Step S215) The deformed object output portion 112 outputs a deformed slice information group (three-dimensional object). This processing is referred to as deformation processing, and will be described with reference to the flowcharts in FIGS. 3 and 4. The deformation processing of the three-dimensional object corresponds to the instruction in step S201. More specifically, if the user presses a given point or region with PHANToM, the three-dimensional object is deformed according to the pressing strength (or time, etc.). The procedure proceeds to step S204.

Herein, in the flowchart in FIG. 2, the deformation processing in step S215 may be performed before step S210.

Note that the processing is ended by powering off or interruption for aborting the processing in the flowchart in FIG. 2.

Next, the deformation processing in step S215 will be described with reference to the flowchart in FIGS. 3 and 4.

(Step S301) The second mesh information acquiring portion 108 reads first mesh information, from the first mesh information storage portion 104.

(Step S302) The second mesh information acquiring portion 108 deforms the first mesh information that has been read in step S301, based on the instruction that has been received in step S201, thereby acquiring second mesh information constituting the deformed shape. The processing of deforming the mesh information based on a deformation instruction is a well known technique (technique according to the finite element method), and thus a detailed description thereof has been omitted.

(Step S303) The first slice information group acquiring portion 109 acquires a first slice information group, which is multiple pieces of slice information, based on the second mesh information that has been acquired in step S302. The three-dimensional object constituted by the second mesh information is sliced, and thus information of multiple planes is obtained. This plane information is the slice information. The slice information is a collection of points represented by the coordinate information (x, y, z), and does not have color information. In this case, the first slice information group acquiring portion 109 acquires a first slice information group, which is multiple pieces of slice information perpendicular to the line-of-sight vector and sliced at predetermined intervals. Herein, the slice information constituting the first slice information group does not have color information.

(Step S304) The second slice information group acquiring portion 111 acquires a second slice information group. This processing will be described in detail with reference to the flowchart in FIG. 4.

(Step S305) The deformed object output portion 112 outputs the second slice information group that has been acquired in step S304. The procedure returns to an upper-level function.

Next, the processing of acquiring the second slice information group in step S304 will be described with reference to the flowchart in FIG. 4.

(Step S401) The second slice information group acquiring portion 111 substitutes 1 for a counter i.

(Step S402) The second slice information group acquiring portion 111 judges whether or not the $i^{th}$ slice information (unprocessed slice information) is present in the first slice information group. If the $i^{th}$ slice information is present, the procedure proceeds to step S403. If the $i^{th}$ slice information is not present, the procedure returns to an upper-level function.

(Step S403) The second slice information group acquiring portion 111 substitutes 1 for a counter j.

(Step S404) The second slice information group acquiring portion 111 judges whether or not the unprocessed $j^{th}$ point is present in the $i^{th}$ slice information. If the $j^{th}$ point is present, the procedure proceeds to step S405. If the $j^{th}$ point is not present, the procedure jumps to step S409. Herein, the term "unprocessed" refers to a state in which no color information has been set.

(Step S405) The corresponding point determining unit 1101 determines a point that corresponds to the $j^{th}$ point in the $i^{th}$ slice information, and that is contained in the 3D voxel information. The point contained in the 3D voxel information is a point before deformation. Herein, the $j^{th}$ point is a point after deformation. An example of the algorithm for determining the point in the 3D voxel information will be described later in detail.

(Step S406) The color information determining unit 1102 acquires color information of the point in the 3D voxel information that has been determined in step S405.

(Step S407) The color information determining unit 1102 sets the color information that has been acquired in step S406, as the color information of the $j^{th}$ point in the $i^{th}$ slice information.

(Step S408) The second slice information group acquiring portion 111 increments, the counter j by 1. The procedure returns to step S404.

(Step S409) The second slice information group acquiring portion 111 increments the counter i by 1. The procedure returns to step S402.

Hereinafter, a specific operation of the information processing apparatus in this embodiment will be described. In this information processing apparatus, for example, the three-dimensional object is an organ such as the heart or the lung. Note that such a three-dimensional object can be approximated by a collection of tetrahedrons. Herein, for the sake of simplicity of illustration, a case will be described in which the tetrahedron shown in FIG. 5A is deformed. In FIG. 5A, the four points A, B, C, and O are provided. The point P is a given point inside the tetrahedron.

In the object information storage portion 103, the 3D voxel information shown in FIG. 6 is stored. In the first mesh information storage portion 104, for example, the first mesh information shown in FIG. 7 is stored. The 3D voxel information is a collection of point information that is information of all points constituting the tetrahedron shown in FIG. 5A. The point information herein has the positional information (x, y, z), the color information (such as "$col_1$" in FIG. 6), and the elasticity information (such as "$e_1$" in FIG. 6). Furthermore, the first mesh information is, for example, a collection of information of points outside and inside the tetrahedron (the points are spaced away from each other).

Furthermore, the slice information group acquiring portion 105 acquires a slice information group, which is multiple pieces of slice information perpendicular to the line-of-sight vector and sliced at predetermined intervals as shown in FIG. 8, from the 3D voxel information. The slice information group acquiring portion 105 obtains the positions "minD" and "maxD" of the three-dimensional object that is to be displayed, and slices the three-dimensional object at a predetermined interval "D", thereby acquiring multiple pieces of slice information. The slice information is a collection of point information. Furthermore, there is no spacing between the points constituting the slice information. More specifically, a plane represented by the slice information is packed with information of the points. The point information has the positional information (x, y, z), and does not have color information. As a result, the slice information group acquiring portion 105 acquires the slice information group shown in FIG. 9. The slice information group has slice information $S_1$, slice information $S_2$, slice information $S_3$, and the like. Herein, the slice information is acquired perpendicularly to the line-of-sight vector, in order to allow even thinned slice information to be viewed in three dimensions by the user viewing a collection of the slice information. Furthermore, slice information that has been thinned out at predetermined intervals is acquired, in order to increase the speed of display processing. The slice information is acquired at constant intervals, in order to display a high-quality three-dimensional object. Herein, the line-of-sight vector is a vector perpendicular to the screen, and if the instruction receiving portion 102 receives a rotation instruction, the line-of-sight vector changes according to the rotation instruction.

Then, the slice information group acquiring portion 105 at least temporarily stores the acquired slice information group in FIG. 9, in the slice information group storage portion 106.

Next, the slice information group output portion 107 outputs the slice information group in the slice information group storage portion 106. Herein, with the slice information group that has been output, the user can recognize a three-dimensional tetrahedron. Herein, a trigger for the slice information group output portion 107 to output the slice information group may be an instruction from the user, or may be reception of a command from an external apparatus, for example. Any trigger may be used.

Next, it is assumed that the user tries to deform the displayed three-dimensional tetrahedron, by inputting an instruction for a given point or region in the slice information group that has been output. This instruction is referred to as a deformation instruction. Herein, the deformation instruction is input, for example, with PHANToM included in the information processing apparatus. The input with PHANToM is, for example, input of pressing the point O in the tetrahedron shown in FIG. 5A leftward with a predetermined force. Then, the instruction receiving portion 102 receives the deformation instruction. With this input, the tetrahedron shown in FIG. 5A is changed into the tetrahedron as shown in FIG. 5B. Then, based on this deformation instruction, the second mesh information acquiring portion 108 deforms the first mesh information in FIG. 7, thereby acquiring second mesh information constituting the deformed shape. FIG. 10 shows the second mesh information. More specifically, the second mesh information is information indicating the tetrahedron in FIG. 5B. Herein, the processing of acquiring second mesh information by deforming the first mesh information is a well known technique according to the finite element method, and thus a detailed description thereof has been omitted.

Next, the processing of acquiring the color information will be described. As shown in FIGS. 5A and 5B, if a given point P inside a mesh element is displaced to P' by input of a deformation instruction, it is necessary to assign the color information at the position of P in the 3D voxel information, to the color information of P'. If the relative position of arbitrary points inside the mesh from each of the vertices does not change before and after deformation, then the positions of the internal points P and P' before and after deformation can be represented as a linear combination of the edges, using common parameters s, t and u as follows.

$$OP = sOA + tOB + uOC \quad \text{Equation (1)}$$

$$O'P' = sO'A' + tO'B' + uO'C' \quad \text{Equation (2)}$$

Herein, the corresponding point determining unit 1101 solves Equation (2), obtains the parameters s, t, and u defining the internal point P' from the mesh after deformation, and obtains the position P before deformation from Equation (1). Then, the color information corresponding to the position P is acquired from the 3D voxel information shown in FIG. 6. Then, the color information determining unit 1102 acquires and sets the color information of each point that is determined by the corresponding point determining unit 1101 and that is in the multiple pieces of slice information constituting the first slice information group. As a result, each point constituting each of the slice information in FIG. 11 after deformation has color information.

In the above-described processing, even if a node (point) constituting the mesh information is displaced, or the mesh information is reconstructed, the color information at an arbitrary internal point can be reproduced, as long as the relative position of the points in the element from the nodes can be obtained before and after a simulation.

Next, the deformed object output portion 112 outputs the second slice information group. With this processing, the three-dimensional object after reception of the deformation instruction can be displayed in real time. By repeating reception of the deformation instruction and output of the three-dimensional object after deformation, it is possible to realize, for example, biological function analysis, real-time surgical simulations and the like in the medical field.

Next, the positional information acquiring portion 113 acquires one or more pieces of positional information of the point, or a point constituting the region, corresponding to the received instruction (deformation instruction). Herein, for example, the positional information of the point O is acquired. Next, the elasticity information acquiring portion 114 acquires one or more pieces of elasticity information (e) paired with the positional information of the point O that has been acquired by the positional information acquiring portion 113, from each slice information in the slice information group storage portion 106 or the 3D voxel information in the object information storage portion 103.

Next, the elasticity information output portion 115 arithmetically calculates a force vector that is to be output, from the one or more pieces of elasticity information that have been acquired by the elasticity information acquiring portion 114. In the case of one piece of elasticity information acquired by the elasticity information acquiring portion 114, the elasticity information output portion 115 typically outputs the elasticity information without any processing.

Next, the elasticity information output portion 115 outputs the acquired force vector to PHANToM. Then, the PHANToM drives a motor according to the force vector. Then, the user using the PHANToM can feel a reaction force obtained in response to the performed pressing.

As described above, according to this embodiment, it is possible to render deformation and destruction in a mesh in real time, together with the color information of its surface and interior. Furthermore, it is possible to handle information relating to the elasticity of a three-dimensional object. More specifically, in a case where a three-dimensional object that has been output is pressed or grasped using an input/output device such as PHANToM, it is possible to change the shape of the three-dimensional object while feeling the hardness of the pressed or grasped section. Furthermore, according to this embodiment, it is possible to simulate deformation of a three-dimensional object in real time while feeling the hardness, using the slice information group acquired from 3D voxel information and the mesh information. That is to say, it is possible to perform high-precision rendering of the surface and internal structure of an object by expressing the mesh elements after deformation by overlapping texture-mapped cross sections, using both the voxel data (3D voxel information) of the original image and the mesh data (mesh information) of the target region. Further, since each point constituting the three-dimensional object and/or each point constituting the slice information group has the elasticity information, it is possible for the user to simulate deformation of the three-dimensional object while feeling the hardness of the three-dimensional object. Furthermore, according to this embodiment, it is possible to generate a smooth deformation animation on a general-purpose PC, for example, for volume data of 256×256×256 voxels, in accordance with dynamic computational algorithms typified by the finite element method without requiring a dedicated graphics card.

Herein, the processing of the information processing apparatus according to this embodiment was evaluated. In order to examine the calculation time required for rendering, two patterns of volume textures, namely 256×256×256 and 128×128×128 corresponding to four patterns of meshes having the same shape but different levels of detail (the cube in FIG. 12A, having numbers of meshes E of 589, 1104, 4463, and 8468, respectively) were prepared. Considering cases where each of these has a slice interval D of 1.0 and 2.0, the number of frames rendered per second was measured for all 16 patterns. FIG. 13 shows the number of frames for each of the cases. It will be appreciated that each of the image data in FIG. 12 also contains the color information.

Furthermore, according to this embodiment, as the number of elements increases, the number of base polygons generated increases, and the number of frames decreases. The number of frames is substantially proportional to the slice interval D. In the case of using the volume texture of 256×256×256 voxels, if the slice interval D was 2, the meshes having about up to 2000 elements could realize a number of frames of at least 10 Hz, and it was possible to present interactively smooth animation for a manipulation on the object.

Furthermore, the information processing apparatus according to this embodiment is useful for visualization of the surface and internal structures of a three-dimensional object such as a human organ, acquired by CT or MRI, at the time of performing a deformation simulation on the shape of the object. In this respect, the results of applying the information processing apparatus to the shape of a three-dimensional object such as a human organ are described below. For example, FIG. 14A shows a result of volume rendering of a myocardial region extracted from a collection of two-dimensional images acquired by CT. FIG. 14B shows a result of creating a tetrahedral mesh model having the same shape and performing a deformation simulation. Since the gray values are reflected, the properties of the microstructure of a coronary artery or the like, or the object surface after deformation are rendered with high definition. Furthermore, deformation of the internal structure (cardiac lumen) can be observed by changing the α value. The same is applied to other embodiments. It will be appreciated that, each of the image data in FIG. 14 also contains the color information. Furthermore, at the time of deformation, it is possible for the user to feel the hardness of that section.

Furthermore, the information processing apparatus according to this embodiment is useful not only for the simulation of deformation of three-dimensional objects such as organs, but also for a wide range of computer graphics-related applications including creating animations for entertainment purposes, making is possible to greatly extend the applicable range of volume visualization.

Furthermore, in this embodiment, if the processing is performed in which the point X is pressed using PHANToM with respect to a three-dimensional object as shown in FIG. 15A, the three-dimensional object is deformed as shown in FIG. 15B, and a force required for the deformation returns to the PHANToM, and the user can feel that force. This three-dimensional object is an engine of a car. FIGS. 15A and 15B illustrate the manner in which dynamic structural analysis is performed. Herein, in a case where the three-dimensional object is a human organ, and this mechanism is used in simulations of human surgeries, it is possible to simulate surgeries of the human body, through not only sight but also feel of touch.

The processing in this embodiment may be implemented by software. The software may be distributed by software downloading or the like. The software may be distributed in the form where the software is stored in a storage medium such as a CD-ROM. Note that the same is applied to the other embodiments described in this specification. The software that implements the information processing apparatus in this embodiment may be a following program. Specifically, this program is a program for causing a computer to execute: a slice information group output step of outputting a slice information group having multiple pieces of slice information, the slice information being information constituted based on two-dimensional image data obtained as a result of extraction with multiple planes from 3D voxel information, which is volume texture of a three-dimensional object, and being constituted by information of multiple points having positional information, which is information indicating position, and elasticity information, which is information of elasticity; an instruction receiving step of receiving an instruction for a given point or region in the slice information group that has been output; a positional information acquiring step of acquiring at least one piece of positional information of the point, or a point constituting the region, corresponding to the instruction; an elasticity information acquiring step of acquiring at least one piece of elasticity information paired with the at least one piece of positional information that has been acquired in the positional information acquiring step; and an elasticity information output step of performing output based on the at least one piece of elasticity information that has been acquired in the elasticity information acquiring step.

Also, this program may be a program for causing a computer to execute: a slice information group output step of outputting a slice information group having multiple pieces of slice information, the slice information being information constituted based on two-dimensional image data obtained as a result of extraction with multiple planes from 3D voxel information, which is volume texture of a three-dimensional object, and being constituted by information of multiple points having positional information, which is information indicating position, color information, which is information of color, and elasticity information, which is information of elasticity; an instruction receiving step of receiving an instruction for a given point or region in the slice information group that has been output; a second mesh information acquiring step of deforming stored first mesh information based on the instruction, thereby acquiring second mesh information constituting the deformed shape; a first slice information group acquiring step of acquiring a first slice information group, which is multiple pieces of slice information that do not have color information, based on the second mesh information; a color information determining step of determining color information of each point that is contained in the multiple pieces of slice information constituting the first slice information group, and that corresponds to a point in the 3D voxel information; a second slice information group acquiring step of setting new color information for each point in the first slice information group that has been acquired in the first slice information group acquiring step, based on the color information of each point that has been determined in the color information determining step, thereby acquiring a second slice information group; a deformed object output step of outputting the second slice information group; a positional information acquiring step of acquiring at least one piece of positional information of the point, or a point constituting the region, corresponding to the instruction; an elasticity information acquiring step of acquiring at least one piece of elasticity information paired with the at least one piece of positional information that has been acquired in the positional information acquiring step; and an elasticity information output step of performing output based on the at least one piece of elasticity information that has been acquired in the elasticity information acquiring step.

Embodiment 2

In this embodiment, an information processing apparatus will be described that has an authoring function with which the elasticity information described in Embodiment 1 can be easily set. In this embodiment, in the information processing apparatus, desired elasticity information can be freely set for a partial three-dimensional region specified by the user in a three-dimensional object.

FIG. 16 is a block diagram of the information processing apparatus in this embodiment.

The information processing apparatus includes an input receiving portion 1601, the object information storage portion 103, the first mesh information storage portion 104, the slice information group acquiring portion 105, the slice information group storage portion 106, the slice information group output portion 107, a three-dimensional region mask shape changing portion 1602, a three-dimensional region mask position changing portion 1603, a mesh information acquiring portion 1604, and an elasticity information setting portion 1605.

The input receiving portion 1601 receives, for example, input regarding a three-dimensional region mask having a three-dimensional geometric shape, input regarding elasticity information, which is information of elasticity, and an output instruction to output a slice information group. The three-dimensional region mask is information for extracting (defining a region of) 3D voxel information or a slice information group having one or more pieces of slice information, and is information having a three-dimensional geometric shape. The three-dimensional region mask is three-dimensional mesh information. The three-dimensional mesh information is a collection of information of points constituting a three-dimensional object. The three-dimensional mesh information is a collection of information of discrete points. The information of the points is typically the coordinate information (x, y, z). The elasticity information is, for example, modulus of elasticity. Herein, the elasticity information that is received by the input receiving portion 1601 is elasticity information set for a collection of points in a three-dimensional region specified with the three-dimensional region mask. Furthermore, examples of the input regarding the three-dimensional region mask include a generation instruction, which is an instruction to generate the three-dimensional region mask, a shape change instruction, which is an instruction to change the shape of the three-dimensional region mask, and a position change instruction, which is an instruction to change the position of the three-dimensional region mask. Herein, the generation instruction may be, for example, an instruction to arrange the three-dimensional region mask in the 3D voxel information. In a case where multiple shapes of three-dimensional region masks are present, the generation instruction may be, for example, an instruction to select a shape from among these shapes, and to arrange a three-dimensional region mask with this shape, in the 3D voxel information. Also, the generation instruction may be, for example, an instruction to construct a three-dimensional region mask in three dimensions, the instruction being input by tracing the profile of a displayed image in three dimensions with input means such as a mouse. Furthermore, with the output instruction, a slice information group is output. Means for inputting these instructions or elasticity information may be any means, such as a numeric keypad, a keyboard, a mouse, or a menu screen. The input receiving portion 1601 can be implemented, for example, as a device driver for input means such as a numeric keypad or a keyboard, or control software for a menu screen. Herein, the three-dimensional region mask is typically a collection of tetrahedrons. Each vertex of the tetrahedrons constituting the three-dimensional region mask that has been output may have not only coordinate information but also elasticity information, or may have elasticity information in association with each vertex of the tetrahedrons.

If the input receiving portion 1601 receives the shape change instruction, the three-dimensional region mask shape changing portion 1602 changes the shape of the three-dimensional region mask based on the shape change instruction, and outputs the three-dimensional region mask. The three-dimensional region mask shape changing portion 1602, for example, reduces the size of the three-dimensional region mask to 90% without changing its centroid, each time the input receiving portion 1601 receives a click of the right button of a mouse serving as the input means. Furthermore, the three-dimensional region mask shape changing portion 1602, for example, enlarges the size of the three-dimensional region mask to 110% without changing its centroid, each time the input receiving portion 1601 receives a click of the left button of a mouse serving as the input means. Furthermore, if the input receiving portion 1601 receives a signal generated by dragging a mouse serving as the input means, then according to the signal, the three-dimensional region mask shape changing portion 1602 changes the shape of a section (point) for which the instruction with the mouse has been given. The processing performed by the three-dimensional region mask shape changing portion 1602 is well known processing of deforming three-dimensional mesh information, and thus a detailed description thereof has been omitted. Typically, the three-dimensional region mask shape changing portion 1602 can be implemented, for example, as an MPU or a memory. Typically, the processing procedure of the three-dimensional region mask shape changing portion 1602 is implemented by software, and the software is stored in a storage medium such as a ROM. Note that the processing procedure also may be implemented by hardware (dedicated circuit).

If the input receiving portion 1601 receives the position change instruction, the three-dimensional region mask position changing portion 1603 changes the position of the three-dimensional region mask based on the position change instruction, and outputs the three-dimensional region mask. The phrase "to change the position of the three-dimensional region mask" refers to an operation of changing the relative position with respect to the slice information group. In a case where the input means is PHANToM, for example, if the PHANToM is pressed, then the three-dimensional region mask position changing portion 1603 performs processing of moving the three-dimensional region mask in the deeper direction with respect to the depth of the slice information group. The processing performed by the three-dimensional region mask position changing portion 1603 is well known processing of changing the position of a three-dimensional mesh, and thus a detailed description thereof has been omitted. Typically, the three-dimensional region mask position changing portion 1603 can be implemented, for example, as an MPU or a memory. Typically, the processing procedure of the three-dimensional region mask position changing portion 1603 is implemented by software, and the software is stored in a storage medium such as a ROM. Note that the processing procedure also may be implemented by hardware (dedicated circuit).

The mesh information acquiring portion 1604 acquires and outputs mesh information, which is three-dimensional mesh information constituting the three-dimensional region mask. As the mesh information, mesh information (mesh information constituting the three-dimensional region mask) acquired based on the instruction that has been received by the input receiving portion 1601 may be used without any processing. Furthermore, the mesh information may be mesh information of the three-dimensional region mask obtained as a result of processing performed by the three-dimensional region mask shape changing portion 1602 and/or the three-dimensional region mask position changing portion 1603. It is assumed that if the input receiving portion 1601 receives selection of the shape of the three-dimensional region mask, mesh information with shapes that can be selected is held in advance in the mesh information acquiring portion 1604. Typically, the mesh information acquiring portion 1604 can be implemented, for example, as an MPU or a memory. Typically, the processing procedure of the mesh information acquiring portion 1604 is implemented by software, and the software is stored in a storage medium such as a ROM. Note that the processing procedure also may be implemented by hardware (dedicated circuit).

The elasticity information setting portion 1605 sets elasticity information for each point that is contained in each slice information of the slice information group, and that is contained in an internal region, which is a region inside the mesh information, based on the mesh information. This elasticity information is elasticity information based on the input that has been received by the input receiving portion 1601. Also, the elasticity information setting portion 1605 may set elasticity information for each point that constitutes the 3D voxel data in the object information storage portion 103, and that is contained in an internal region, which is a region inside the mesh information, based on the mesh information. Typically, the elasticity information setting portion 1605 can be implemented, for example, as an MPU or a memory. Typically, the processing procedure of the elasticity information setting portion 1605 is implemented by software, and the software is stored in a storage medium such as a ROM. Note that the processing procedure also may be implemented by hardware (dedicated circuit).

Next, the operation of the information processing apparatus will be described with reference to the flowchart in FIG. 17.

(Step S1701) The input receiving portion 1601 judges whether or not input has been received. If the input has been received, the procedure proceeds to step S1702. If the input has not been received, the procedure returns to step S1701.

(Step S1702) The input receiving portion 1601 judges whether or not the input that has been received in step S1701 is an output instruction. If it is the output instruction, the procedure proceeds to step S1703. If it is not the output instruction, the procedure proceeds to step S1705. Herein, the output instruction is, for example, an instruction to start the information processing apparatus or applications.

(Step S1703) The slice information group output portion 107 reads a slice information group from the slice information group storage portion 106.

(Step S1704) The slice information group output portion 107 outputs the slice information group that has been acquired in step S1703. The procedure returns to step S1701.

(Step S1705) The input receiving portion 1601 judges whether or not the input that has been received in step S1701 is a generation instruction. If it is the generation instruction, the procedure proceeds to step S1706. If it is not the generation instruction, the procedure proceeds to step S1708.

(Step S1706) The mesh information acquiring portion 1604 reads and outputs mesh information that is stored in advance. In the mesh information acquiring portion 1604, two or more pieces of mesh information (in the shape of spheres, columns, or the like) may be held in advance.

(Step S1707) The mesh information acquiring portion 1604 temporarily stores the mesh information that has been acquired in step S1706. The procedure returns to step S1701.

(Step S1708) The input receiving portion 1601 judges whether or not the input that has been received in step S1701 is a shape change instruction. If it is the shape change instruction, the procedure proceeds to step S1709. If it is not the shape change instruction, the procedure proceeds to step S1711.

(Step S1709) The three-dimensional region mask shape changing portion 1602 changes the shape of the temporarily stored mesh information, and outputs the changed mesh information.

(Step S1710) The three-dimensional region mask shape changing portion 1602 temporarily stores the mesh information whose shape has been changed in step S1709. The procedure returns to step S1701.

(Step S1711) The input receiving portion 1601 judges whether or not the input that has been received in step S1701 is a position change instruction. If it is the position change instruction, the procedure proceeds to step S1712. If it is not the position change instruction, the procedure proceeds to step S1714.

(Step S1712) The three-dimensional region mask position changing portion 1603 changes the position of the temporarily stored mesh information, and outputs the mesh information. This position is a position in a three-dimensional space.

(Step S1713) The three-dimensional region mask position changing portion 1603 temporarily stores the mesh information whose position has been changed in step S1712. The procedure returns to step S1701.

(Step S1714) The input receiving portion 1601 judges whether or not the input that has been received in step S1701 is elasticity information. If it is the elasticity information, the procedure proceeds to step S1715. If it is not the elasticity information, the procedure returns to step S1701.

(Step S1715) The elasticity information setting portion 1605 sets the elasticity information that has been received in step S1701, as elasticity information of a given point. The processing of setting the elasticity information will be described in detail with reference to the flowchart in FIG. 18.

Note that the processing is ended by powering off or interruption for aborting the processing in the flowchart in FIG. 17.

Next, the processing of setting the elasticity information in step S1715 will be described with reference to the flowchart in FIG. 18.

(Step S1801) The elasticity information setting portion 1605 substitutes 1 for a counter i.

(Step S1802) The elasticity information setting portion 1605 judges whether or not the $i^{th}$ slice information (unprocessed slice information) is present in the first slice information group. If the $i^{th}$ slice information is present, the procedure proceeds to step S1803. If the $i^{th}$ slice information is not present, the procedure returns to an upper-level function.

(Step S1803) The elasticity information setting portion 1605 substitutes 1 for a counter j.

(Step S1804) The elasticity information setting portion 1605 judges whether or not the $j^{th}$ point (unprocessed point) in the $i^{th}$ slice information is present. If the $j^{th}$ point is present, the procedure proceeds to step S305. If the $j^{th}$ point is not present, the procedure jumps to step S313. Herein, the term "unprocessed" refers to a state in which it has not been judged whether or not to set the elasticity information.

(Step S1805) The elasticity information setting portion 1605 acquires the positional information (x, y, z) of the $j^{th}$ point in the $i^{th}$ slice information.

(Step S1806) The elasticity information setting portion 1605 judges whether the $j^{th}$ point is a point in the internal region or a point in the external region. This processing is performed, for example, in the following manner. That is to say, the elasticity information setting portion 1605 calculates all points of intersection between the $i^{th}$ slice information and the first mesh information, in a three-dimensional space (this processing is well known processing). In a case where no such a point of intersection is present, the elasticity information setting portion 1605 judges that all points in the $i^{th}$ slice information are points in the external region. In a case where only one point of intersection is present, the elasticity information setting portion 1605 judges that only that one point is a point in the internal region and the other points are points in the external region. In a case where multiple points of intersection are present, the multiple points of intersection constitute a closed plane. If the $j^{th}$ point is a point in this closed plane, the elasticity information setting portion 1605 judges that this point is a point in the internal region. If the $j^{th}$ point is not a point in this closed plane, the elasticity information setting portion 1605 judges that this point is a point in the external region. Herein, in a case where all points constituting the boundary of a closed plane are given, the processing of judging whether or not an arbitrary point j is a point in this plane is well known processing, and thus a detailed description thereof has been omitted.

(Step S1807) If it is judged in step S1806 that the point is a point in the internal region, the procedure of the elasticity information setting portion 1605 proceeds to step S1808. If it is judged that the point is a point in the external region, the procedure proceeds to step S1809.

(Step S1808) The elasticity information setting portion 1605 sets the received elasticity information, as the elasticity information of the $j^{th}$ point.

(Step S1809) The elasticity information setting portion 1605 increments the counter j by 1: The procedure proceeds to step S1804.

(Step S1810) The elasticity information setting portion 1605 increments the counter i by 1. The procedure proceeds to step S1802.

Hereinafter, a specific operation of the information processing apparatus in this embodiment will be described.

In this information processing apparatus, a three-dimensional object that is to be output is, for example, the human trunk.

It is assumed that in the object information storage portion 103, 3D voxel information having a structure as shown in FIG. 6 is stored. Furthermore, it is assumed that in the first mesh information storage portion 104, for example, first mesh information having a structure as shown in FIG. 7 is stored.

Furthermore, the slice information group acquiring portion 105 acquires a slice information group, which is multiple pieces of slice information perpendicular to the line-of-sight vector and sliced at predetermined intervals as shown in FIG. 8, from the 3D voxel information.

Then, the slice information group acquiring portion 105 at least temporarily stores the acquired slice information group, in the slice information group storage portion 106.

Next, the slice information group output portion 107 displays the slice information group in the slice information group storage portion 106. FIG. 19 is an example of this display. FIG. 19 shows an example in which the slice information group acquiring portion 105 extracts multiple pieces of slice information from the 3D voxel information in FIG. 6, using the three-dimensional region mask, acquires, for each point in each slice information, the color information of a point in the 3D voxel information corresponding thereto, and constitutes multiple pieces of slice information having the color information that are to be output, and the slice information group output portion 107 displays the multiple pieces of slice information. The method for extracting multiple pieces of slice information from the 3D voxel information is similar to the method for extracting the multiple pieces of slice information in FIG. 9, from the tetrahedron in FIG. 5. The technique for extracting multiple pieces of slice information from 3D voxel information is a well known technique, and thus a detailed description thereof has been omitted.

Next, it is assumed that the user has input an instruction to generate a spherical three-dimensional mask. Next, the input receiving portion 1601 receives the generation instruction. Then, the mesh information acquiring portion 1604 reads mesh information (stored in advance) constituting the spherical three-dimensional mask. The spherical mesh information is information constituted by a collection of points in a part of the surface of the sphere. Then, the mesh information acquiring portion 1604 temporarily stores the acquired mesh information. Then, the mesh information is displayed (see FIG. 20). The mesh information is spherical mesh information of the trunk viewed from front.

Then, the user inputs an instruction to change the position and the shape of the displayed mesh information (shape change instruction, position change instruction), with input means such as a mouse. This instruction is given by manipulating, for example, dragging a mouse. Then, the three-dimensional region mask position changing portion 1603 changes the position of the temporarily stored mesh information, and the three-dimensional region mask shape changing portion 1602 changes the shape of the temporarily stored mesh information. It is assumed that as a result, the mesh information in FIG. 20 has been changed to the mesh information as shown in FIG. 21. Herein, the processing of changing the shape or the position of three-dimensional mesh information based on an instruction from the user (instruction from a mouse or the like) is a well known technique.

Next, it is assumed that the user inputs an instruction to display a menu via which elasticity information is input. Then, the information processing apparatus displays a menu via which elasticity information is input. It is then assumed that the user inputs, for example, the elasticity information (modulus of elasticity) "53". Then, if an unshown "OK" button is pressed, the elasticity information setting portion 1605 sets "53", as the elasticity information of dots in the internal region of the three-dimensional region mask constituted by the mesh information. More specifically, the dots in the internal region of the three-dimensional region mask constituted by the mesh information are "(x, y, z, col, 53)". Herein, (x, y, z, col) may be different between the dots.

As described above, according to this embodiment, it is possible to easily set the elasticity information for a partial three-dimensional region constituting the three-dimensional object. More specifically, according to this embodiment, it is possible to set, at a time, the elasticity information of organs, predetermined sections of the three-dimensional object having similar hardness, or the like.

Herein, according to this embodiment, it will be appreciated that any interface may be used for inputting the elasticity information. In FIG. 22, a numerical value was input, but the elasticity information may be input, for example, by sliding a bar.

Software that implements the information processing apparatus in this embodiment may be a following program. Specifically, this program is a program for causing a computer to execute: a slice information group output step of outputting a slice information group having multiple pieces of slice information, the slice information being information constituted based on two-dimensional image data obtained as a result of extraction with multiple planes from 3D voxel information, which is volume texture of a three-dimensional object, and being constituted by information of multiple points having positional information, which is information indicating position, and elasticity information, which is information of elasticity; an input receiving step of receiving input regarding a three-dimensional region mask having a three-dimensional geometric shape, and input regarding elasticity information, which is information of elasticity; a mesh information acquiring step of acquiring mesh information, which is three-dimensional mesh information constituting the three-dimensional region mask; and an elasticity information setting step of setting elasticity information based on the input that has been received in the input receiving step, for each point that is contained in each slice information of the slice information group, and that is contained in an internal region, which is a region inside the mesh information, based on the mesh information.

Embodiment 3

In this embodiment, an information processing apparatus will be described that specifies a region that is to be deformed, and simulates deformation of a three-dimensional object, using a surgical instrument metaphor, which is a metaphor of a surgical instrument, which is a tool used for surgeries. This information processing apparatus can assist, for example, surgical planning.

FIG. 23 is a block diagram of the information processing apparatus in this embodiment.

This information processing apparatus includes the input/output device 101, the instruction receiving portion 102, the object information storage portion 103, the first mesh information storage portion 104, the slice information group acquiring portion 105, the slice information group storage portion 106, the slice information group output portion 107, a second mesh information acquiring portion 2308, the first slice information group acquiring portion 109, the color information determining portion 110, the second slice information group acquiring portion 111, the deformed object output portion 112, the positional information acquiring portion 113, the elasticity information acquiring portion 114, and the elasticity information output portion 115. The color information determining portion 110 includes the corresponding point determining unit 1101, the color information determining unit 1102, a surgical instrument metaphor storage portion 2301, and a surgical instrument metaphor output portion 2302.

Furthermore, the second mesh information acquiring portion 2308 includes a manipulation node determining unit 23081, a displacement determining unit 23082, and a second mesh information acquiring unit 23083.

In the surgical instrument metaphor storage portion 2301, a surgical instrument metaphor, which is a metaphor of a surgical instrument, is stored. The surgical instrument metaphor is bitmap data or graph data of scissors, tweezers, or the like. The surgical instrument metaphor preferably has the shape of the surgical instrument, but also may have the shape of a rectangular parallelepiped, sphere, or the like. The surgical instrument metaphor storage portion 2301 is preferably a non-volatile storage medium such as a hard disk or a ROM, but can be implemented also as a volatile storage medium such as a RAM.

The surgical instrument metaphor output portion 2302 reads a surgical instrument metaphor from the surgical instrument metaphor storage portion 2301, and outputs the surgical instrument metaphor. The term "output" herein refers to displaying on a display screen and transmission to an external apparatus (display apparatus). The surgical instrument metaphor output portion 2302 may be considered to include, or not to include, an output device such as a display. The surgical instrument metaphor output portion 2302 can be implemented, for example, as driver software for an output device, or a combination of driver software for an output device and the output device.

Furthermore, the instruction receiving portion 102 herein receives an instruction for a given region in the slice information group that has been output. This instruction is, for example, an instruction to rotate and/or translate the region. Also, this instruction is preferably an instruction regarding movement or manipulation of the surgical instrument metaphor.

The second mesh information acquiring portion 2308 specifies the region for which an instruction has been received by the instruction receiving portion 102, and deforms the first mesh information in the first mesh information storage portion 104 according to the deformation instruction (pinching or twisting instruction, etc.), thereby acquiring second mesh information constituting the deformed shape. More specifically, the region for which an instruction has been received by the instruction receiving portion 102 is specified, information for displacing multiple points (manipulation nodes described later) according to the deformation instruction is given to the second mesh information acquiring portion 2308, displacement of displaceable points (free nodes described later) is calculated from the information for displacing the multiple points, and thus second mesh information constituting the deformed shape is acquired. The processing of calculating displacement of displaceable points (free nodes described later) from the information for displacing the multiple points is typically well known processing according to the finite element method, and thus a detailed description thereof has been omitted.

The manipulation node determining unit 23081 determines manipulation nodes, according to the instruction (instruction for a given region in the slice information group that has been output) that has been received by the instruction receiving portion 102. The manipulation nodes are nodes (points) that are forcibly displaced at the time of expression of face manipulation (manipulation for a region having multiple points).

Hereinafter, a specific algorithm will be described in which the manipulation node determining unit 23081 determines manipulation nodes. It is herein assumed that the instruction that has been received by the instruction receiving portion 102 is an instruction for a region using a surgical instrument metaphor. It is assumed that the surgical instrument metaphor is, for example, a rectangular parallelepiped as shown in FIG. 24. Furthermore, it is assumed that the surgical instrument metaphor is also referred to as a "manipulator", and is constituted by tetrahedron meshes, each of which is a collection of four points. FIG. 24 shows a concept in which a three-dimensional object having the shape of an organ is deformed by manipulating a surgical instrument metaphor (the rectangular parallelepiped in FIG. 24).

In this case, the manipulation node determining unit 23081 determines the manipulation nodes, for example, in the following conditions. The manipulation node determining unit 23081 places the surgical instrument metaphor onto a region specified with a three-dimensional object (such as an organ object having the shape of an organ), and groups of points on the surface of a portion where the surgical instrument metaphor and the three-dimensional object are overlapped are taken as manipulation nodes. Whether or not to be the manipulation nodes is judged by checking each node of the three-dimensional object, in each tetrahedron constituting the surgical instrument metaphor. More specifically, for example, the manipulation node determining unit 23081 uses Numerical Expression 1 representing the relationship between the vertices (o, a, b, c) and the centroid (P) of the tetrahedron mesh of the surgical instrument metaphor in FIG. 25. Furthermore, the manipulation node determining unit 23081 calculates s, t, and u, according to Numerical Expression 2. Next, the manipulation node determining unit 23081 checks all points in the tetrahedron meshes constituting the three-dimensional object. If a given point satisfies the logical expression in Numerical Expression 3 (if it is true), then this point is a manipulation node. If a given point does not satisfy the logical expression in Numerical Expression 3 (if it is false), then this point is not a manipulation node.

$$\overline{p} = s\overline{a} + t\overline{b} + u\overline{c} \quad \text{Numerical Expression 1}$$

$$\begin{pmatrix} s \\ t \\ u \end{pmatrix} = \begin{pmatrix} a_x & b_x & c_x \\ a_y & b_y & c_y \\ a_z & b_z & c_z \end{pmatrix}^{-1} \begin{pmatrix} p_x \\ p_y \\ p_z \end{pmatrix} \quad \text{Numerical Expression 2}$$

$$\begin{pmatrix} s+t+ \\ u \leq 1 \end{pmatrix} t \begin{pmatrix} 0 \leq \\ s \leq 1 \end{pmatrix} t \begin{pmatrix} 0 \leq \\ t \leq 1 \end{pmatrix} t \begin{pmatrix} 0 \leq \\ u \leq 1 \end{pmatrix} \quad \text{Numerical Expression 3}$$

FIG. 26 shows a concept of the processing of the manipulation node determining unit 23081. In FIG. 26, points in the shape of circles represent free nodes, points in the shape of crosses represent manipulation nodes, and points in the shape of triangles represent fixed nodes. Herein, information of the fixed nodes is typically stored in advance in the information processing apparatus.

The displacement determining unit 23082 determines displacement of the manipulation nodes according to an instruction. For example, the displacement determining unit 23082 determines displacement of the manipulation nodes in the following manner. FIG. 27 shows a concept of displacement of the manipulation nodes. It is assumed that the user has performed manipulation of pinching the organ object using the surgical instrument metaphor. Next, the instruction receiving portion 102 receives the instruction "pinch". Then, the displacement determining unit 23082 calculates displacement of the manipulation nodes (the points in the shape of crosses in FIG. 27(*a*)) according to Numerical Expression 4 below. Numerical Expression 4 is an expression in a case where the point P is displaced to the point P'. Numerical Expression 5 shows the matrix M in Numerical Expression 4. Herein, M is a rotation matrix. Numerical Expression 6 shows the matrix T in Numerical Expression 4. Herein, T is a translation matrix. The displacement determining unit 23082 calculates the node P' after movement, by multiplying the element matrix P of the manipulation nodes, with the rotation matrix M and the translation matrix T.

$$P' = MTP$$

Numerical Expression 4

$$M = \begin{pmatrix} \Delta x^2 + (1 - \Delta x^2)\cos\alpha & -\Delta z\sin\alpha & \Delta y\sin\alpha & 0 \\ \Delta z\sin\alpha & \Delta y^2 + (1 - \Delta y^2)\cos\alpha & -\Delta x\sin\alpha & 0 \\ -\Delta y\sin\alpha & \Delta x\sin\alpha & \Delta z^2 + (1 - \Delta z^2)\cos\alpha & 0 \\ 0 & 0 & 0 & 1 \end{pmatrix}$$

Numerical Expression 5

$$T = \begin{pmatrix} 1 & 0 & 0 & \Delta x \\ 0 & 1 & 0 & \Delta y \\ 0 & 0 & 1 & \Delta z \\ 0 & 0 & 0 & 1 \end{pmatrix}$$

Numerical Expression 6

$$\alpha = \sqrt{\Delta x^2 + \Delta y^2 + \Delta z^2}$$

Numerical Expression 7

In the description above, α represents the rotation amount. Furthermore, T and M are determined by Δx, Δy, and Δz values, and these values are received as input values. The input values are typically values received by the instruction receiving portion 102. Furthermore, Δx, Δy, and Δz respectively represent displacement in the x direction, the y direction, and the z direction. Moreover, Δx, Δy, and Δz are, for example, regularly input one after another, and the displacement determining unit 23082 updates the manipulation node P' after displacement one after another successively according to the input (pinching or pulling manipulation, etc.) from the user.

Herein, in the displacement determining unit 23082, information of Numerical Expressions 4 to 7 above is stored. The displacement determining unit 23082 reads the information of these numerical expressions, and substitutes acquired information for the read numerical expressions, thereby acquiring the manipulation node P' after displacement. Herein, the acquired information is information of, for example, Δx, Δy, and Δz.

The second mesh information acquiring unit 23083 displaces the free nodes according to the multiple manipulation nodes after displacement that have been acquired by the displacement determining unit 23082, and does not displace the fixed nodes, thereby acquiring second mesh information. FIGS. 27(*b*) to 27(*c*) show a concept of this processing of the second mesh information acquiring unit 23083. This arithmetic processing is performed according to the finite element method. Herein, it is assumed that information for identifying the fixed nodes is, for example, held in advance.

Next, the operation of the information processing apparatus will be described with reference to the flowcharts in FIGS. 28 to 31. In FIG. 28, a description of steps in which the same operation as in FIG. 2 is performed has been omitted.

(Step S2801) The instruction receiving portion 102 judges whether or not the instruction that has been received in step S201 is an instruction for a region. If it is the instruction for a region, the procedure proceeds to step S2802. If it is not the instruction for a region, the procedure returns to step S201. Herein, the instruction for a region is preferably given using the surgical instrument metaphor.

(Step S2802) The positional information acquiring portion 113 acquires two or more pieces of positional information of points constituting the region corresponding to the instruction that has been received in step S201.

(Step S2803) The elasticity information acquiring portion 114 acquires two or more pieces of elasticity information paired with the two or more pieces of positional information that have been acquired by the positional information acquiring portion 113, from each slice information in the slice information group storage portion 106 or the 3D voxel information in the object information storage portion 103. First, the elasticity information acquiring portion 114 searches for the points having the two or more pieces of positional information, from each slice information or the 3D voxel information. Next, the elasticity information acquiring portion 114 acquires each elasticity information of the two or more points obtained by the search.

(Step S2804) The elasticity information output portion 115 arithmetically calculates elasticity information that is to be output, from the two or more pieces of elasticity information that have been acquired by the elasticity information acquiring portion 114. The elasticity information that is acquired by the elasticity information output portion 115 may be different from the elasticity information that is to be output thereby. For example, the elasticity information that is acquired may be modulus of elasticity, and the elasticity information that is to be output may be a force. Furthermore, the elasticity information is, for example, modulus of elasticity. The modulus of elasticity may be Young's modulus, volume modulus of elasticity, modulus of rigidity, or Poisson's ratio. In this case, the elasticity information output portion 115 calculates the average value of the two or more pieces of elasticity information, and takes the obtained value as the elasticity information that is to be output. Furthermore, for example, the elasticity information output portion 115 may take the maximum value of the two or more pieces of elasticity information, as the elasticity information that is to be output. Alternatively, the elasticity information output portion 115 may calculate the elasticity information that is to be output, with a predetermined function $f(f(e_1, e_2, \ldots, e_n))$ using two or more pieces of elasticity information $(e_1, e_2, \ldots, e_n)$ as parameters.

(Step S2805) The deformed object output portion 112 outputs a deformed slice information group (three-dimensional object). This processing is referred to as deformation processing, and will be described with reference to the flowchart in FIG. 29. The deformation processing of the three-dimensional object corresponds to the instruction in step S201. The procedure proceeds to step S204.

Herein, in the flowchart in FIG. 28, the deformation processing in step S2805 may be performed before the processing in step S2802.

Next, the deformation processing in the information processing apparatus will be described with reference to the flowcharts in FIGS. 29 to 31 and FIG. 4. In the flowchart in FIG. 29, a description of the same operation as in the flowchart in FIG. 3 has been omitted.

(Step S2901) The second mesh information acquiring portion 2308 reads first mesh information, from the first mesh information storage portion 104.

(Step S2902) The manipulation node determining unit 23081 determines manipulation nodes. The processing of determining the manipulation nodes will be described with reference to the flowchart in FIG. 30.

(Step S2903) The displacement determining unit 23082 determines displacement of the two or more manipulation nodes that have been determined in step S2902, according to an received instruction. The processing of determining displacement of the manipulation nodes will be described with reference to the flowchart in FIG. 31.

(Step S2904) The second mesh information acquiring unit 23083 reads information for identifying the fixed nodes that is held in advance, determines nodes other than the manipulation nodes and the fixed nodes, as the free nodes, and temporarily stores information for identifying the free nodes in a memory.

(Step S2905) The second mesh information acquiring unit 23083 displaces the free nodes, according to the multiple manipulation nodes after displacement that have been acquired by the displacement determining unit 23082, thereby acquiring second mesh information. Herein, displacement of the free nodes is calculated according to the finite element method, using information of displacement of the surrounding multiple nodes (the information of displacement of the manipulation nodes acquired in step S2903). This processing is well known processing according to the finite element method, and thus a detailed description thereof has been omitted. The procedure proceeds to step S303.

Next, the manipulation node determination processing in the information processing apparatus will be described with reference to the flowchart in FIG. 30.

(Step S3001) The manipulation node determining unit 23081 reads the coordinate values $(p_x, p_y, p_z)$ of all nodes (points) P and the coordinate values of the vertices a, b, and c of the tetrahedrons constituting the surgical instrument metaphor.

(Step S3002) The manipulation node determining unit 23081 reads stored information of Numerical Expressions 2 and 3.

(Step S3003) The manipulation node determining unit 23081 substitutes 1 for a counter i.

(Step S3004) The manipulation node determining unit 23081 judges whether or not the $i^{th}$ tetrahedron is present. If the $i^{th}$ tetrahedron is present, the procedure proceeds to step S3005. If the $i^{th}$ tetrahedron is not present, the procedure returns to an upper-level function.

(Step S3005) The manipulation node determining unit 23081 acquires the coordinate values of the nodes (points) P and the vertices a, b, and c of the $i^{th}$ tetrahedron.

(Step S3006) The manipulation node determining unit 23081 substitutes the coordinate values of P, a, b, and c that have been acquired in step S3005, for the read Numerical Expression 2, thereby acquiring s, t, and u.

(Step S3007) The manipulation node determining unit 23081 substitutes s, t, and u that have been acquired in step S3006, for the read Numerical Expression 3.

(Step S3008) The manipulation node determining unit 23081 judges whether the arithmetic result in step S3007 is true or false. If it is true, the procedure proceeds to step S3009. If it is false, the procedure proceeds to step S3010.

(Step S3009) The manipulation node determining unit 23081 stores the coordinate values of the nodes (points) P and the vertices a, b, and c of the $i^{th}$ tetrahedron, on a memory. This processing is an example of the processing of registering the nodes of the $i^{th}$ tetrahedron as the manipulation nodes.

(Step S3010) The manipulation node determining unit 23081 increments the counter i by 1. The procedure returns to step S3004.

Next, the manipulation node displacement processing in the information processing apparatus will be described with reference to the flowchart in FIG. 31.

(Step S3101) The displacement determining unit 23082 reads stored information of Numerical Expressions 4 to 7.

(Step S3102) The displacement determining unit 23082 acquires $\Delta x$, $\Delta y$, and $\Delta z$ obtained as a result of manipulation using the surgical instrument metaphor.

(Step S3103) The displacement determining unit 23082 substitutes 1 for a counter i.

(Step S3104) The displacement determining unit 23082 judges whether or not the $i^{th}$ manipulation node is present. If the $i^{th}$ manipulation node is present, the procedure proceeds to step S3105. If the $i^{th}$ manipulation node is not present, the procedure returns to an upper-level function.

(Step S3105) The displacement determining unit 23082 acquires p(x, y, z) of the $i^{th}$ manipulation node.

(Step S3106) The displacement determining unit 23082 calculates M, T, and a, using Numerical Expressions 5, 6, and 7, and $\Delta x$, $\Delta y$, and $\Delta z$ that have been acquired in step S3102, and temporarily stores the information on a memory.

(Step S3107) The displacement determining unit 23082 calculates P' (P'(x, y, z)) by substituting M, T, and P for Numerical Expression 4, and temporarily stores the information on a memory.

(Step S3108) The displacement determining unit 23082 increments the counter i by 1. The procedure returns to step S3104.

Hereinafter, a specific operation of the information processing apparatus in this embodiment will be described with respect to experimental results. In this information processing apparatus, for example, the three-dimensional object is an organ such as the liver. Herein, in the object information storage portion 103, 256×256×256 CT data of the trunk is held. Furthermore, in the surgical instrument metaphor storage portion 2301, a manipulation object (surgical instrument metaphor) constituted by tetrahedron meshes in the shape of rectangular parallelepipeds is stored. Furthermore, in the first mesh information storage portion 104, information of tetrahedron meshes in the shape of the liver is stored as an organ object. The meshes of the organ object are created using Amira3.1 (Mercury Computer Systems) by extracting the liver region from CT data of the trunk. The created organ object had the number of nodes 787, the number of elements (the number of tetrahedrons) 2999, the Young's modulus 1.0, and the Poisson's ratio 0.4.

Furthermore, the deformation calculation performed by the second mesh information acquiring unit 23083 was based on the equation used in Non-Patent Document 8. Furthermore, a simulation image was generated by rendering each element after deformation. As the algorithm for this rendering, the method used in Non-Patent Document 9 was used.

Furthermore, in this specific example, input means used by the user is a combination of a mouse, a keyboard, and a GUI on a screen.

Herein, the user moves the surgical instrument metaphor, pinches the organ, and rotates the organ using the input means. Herein, the direction of the body axis of the volume image is taken as the z-axis, and the system of coordinates is constituted to be right-handed. Furthermore, at the input interface, the surgical instrument metaphor and the manipulation nodes are translated with right dragging, and the rotation amount and the direction of the rotational axis are determined with left dragging. Furthermore, the rotational center is set to be the center of the surgical instrument metaphor. The manipulation region is determined with a keyboard. Moreover, regarding the displacement amount at the time of performing a pinching manipulation, a slider bar (not shown) on the GUI was used.

In this status, the deformation processing is performed in the following manner. First, the second mesh information acquiring portion 2308 reads first mesh information, from the first mesh information storage portion 104. Then, the manipulation node determining unit 23081 determines manipulation nodes. In order to determine manipulation nodes, the manipulation node determining unit 23081 uses Numerical Expressions 2 and 3 above.

FIG. 32A shows the manner in which a manipulation region is specified in the organ object. The manipulation node determining unit 23081 determines points in the region in which the manipulation object and the organ object are overlapped, as the manipulation nodes. In FIG. 32A, these manipulation nodes are represented as comparatively large gray points (3201, for example). The other points are the fixed nodes or the free nodes. It is assumed that information of the fixed nodes is stored in advance. Herein, FIG. 32B shows a volume image of the liver in which the manipulation nodes have not been displaced.

Next, the user performed a pinching manipulation using the slider bar on the GUI. Next, the displacement determining unit 23082 determines displacement of the manipulation nodes by the above-described processing. Then, the second mesh information acquiring unit 23083 displaces the free nodes, according to the multiple manipulation nodes after displacement that have been acquired by the displacement determining unit 23082, thereby acquiring second mesh information. Next, the first slice information group acquiring portion 109 acquires a first slice information group, which is multiple pieces of slice information, based on the acquired second mesh information. Next, the second slice information group acquiring portion 111 acquires a second slice information group by the above-described processing. Then, the deformed object output portion 112 outputs the acquired second slice information group.

With the processing described above, volume images of the liver in the pinching expression as shown in FIGS. 33A and 33B are displayed. FIG. 33A shows the case in which the displacement amount is small, and the number of manipulation nodes is 18. FIG. 33B shows the case in which the displacement amount is large, and the number of manipulation nodes is 31. FIGS. 33A and 33B both show pinching expression.

Next, it is assumed that the user has input the rotation amount and the direction of the rotational axis by dragging the left button of a mouse. Next, the displacement determining unit 23082 determines displacement of the manipulation nodes by the above-described processing. Then, the second mesh information acquiring unit 23083 displaces the free nodes, according to the multiple manipulation nodes after displacement that have been acquired by the displacement determining unit 23082, thereby acquiring second mesh information. Next, the first slice information group acquiring portion 109 acquires a first slice information group, which is multiple pieces of slice information, based on the acquired second mesh information. Next, the second slice information group acquiring portion 111 acquires a second slice information group by the above-described processing. Then, the deformed object output portion 112 outputs the acquired second slice information group.

With the processing described above, volume images of the liver to which a rotation manipulation has been performed are displayed as shown in FIGS. 34A and 34B. FIG. 34A shows the case in which the rotation amount is small, and FIG. 34B shows the case in which the rotation amount is large. The rotational center is at (40, 80, 100), and the rotational axis is parallel to the x-axis. The output in FIG. 34B shows that the blood vessel structure that was hidden in the initial state has appeared with this manipulation.

Herein, in the above-described experiment, the refresh rate during the manipulation was 8 Hz.

As described above, according to this embodiment, it is possible to assist surgical planning. More specifically, for example, it is possible to perform preoperative simulation of a volume operation in which deformation of an organ caused by a surgical instrument, assumed at the time of endoscopic surgeries, is simulated, and the deformation is rendered on a volume image. Moreover, according to this embodiment, it is possible to construct an environment in which interaction between three-dimensional objects, namely a surgical instrument and an organ, is described, and an interactive manipulation is realized.

Herein, as the experiment in this embodiment, a simulation experiment was performed in which a face manipulation on a volume image was described taking the liver as a model. However, it will be appreciated that the model is not limited to the liver, and the stomach, the heart, or other organs also may be used as the model.

Software that implements the information processing apparatus in this embodiment may be a following program. Specifically, this program is a program for causing a computer to execute the following steps, wherein in the computer, a slice information group having multiple pieces of slice information, and first mesh information, which is three-dimensional mesh information of a three-dimensional object, are stored, the slice information being information constituted based on two-dimensional image data obtained as a result of extraction with multiple planes from 3D voxel information, and being constituted by information of multiple points having positional information, which is information indicating position, and color information, which is information of color, the steps including: a slice information group output step of outputting the slice information group; an instruction receiving step of receiving an instruction for a given region in the slice information group that has been output; a second mesh information acquiring step of deforming the first mesh information based on the instruction, thereby acquiring second mesh information constituting the deformed shape; a first slice information group acquiring step of acquiring a first slice information group, which is multiple pieces of slice information that do not have color information, based on the second mesh information; a color information determining step of determining color information of each point that is contained in the multiple pieces of slice information constituting the first slice information group, and that corresponds to a point in the 3D voxel information; a second slice information group acquiring step of setting new color information for each point in the first slice information group that has been acquired in the first slice information group acquiring step, using the color information of each point that has been determined in the color information determining step, thereby acquiring a second slice information group; and a deformed object output step of outputting the second slice information group.

Furthermore, in this program, it is preferable that the first mesh information has a manipulation node, which is a point that is displaced according to the instruction that has been received in the instruction receiving step, a free node, which is a point that is displaceable according to the displacement of the manipulation node, and a fixed node, which is a point that is not displaced, and in the second mesh information acquiring step, second mesh information is acquired by displacing the manipulation node according to the instruction, displacing the free node according to the displacement of the manipulation node, and not displacing the fixed node.

Furthermore, in this program, it is preferable that the second mesh information acquiring step further comprises a manipulation node determining step of determining a manipulation node according to the instruction.

Furthermore, in this program, it is preferable that the instruction that has been received in the instruction receiving step is an instruction to rotate and/or translate the region, and the second mesh information acquiring step comprises a displacement determining step of determining the displacement of the manipulation node according to the instruction.

Furthermore, in this program, it is preferable that the computer further executes a surgical instrument metaphor output step of reading and outputting a surgical instrument metaphor, which is a metaphor of a surgical instrument, an instruction regarding movement or manipulation of the surgical instrument metaphor is received in the instruction receiving step, and the instruction serves as an instruction for a given region in the slice information group that has been output.

Furthermore, in this program, it is preferable that the computer further executes: a positional information acquiring step of acquiring multiple pieces of positional information of points constituting a region corresponding to the instruction; an elasticity information acquiring step of acquiring multiple pieces of elasticity information paired with the multiple pieces of positional information that have been acquired in the positional information acquiring step; and an elasticity information output step of performing output using the multiple pieces of elasticity information that have been acquired in the elasticity information acquiring step.

Embodiment 4

FIG. 35 is a block diagram of the information processing apparatus in this embodiment.

The information processing apparatus includes an object information storage portion 3501, an input receiving portion 3502, a three-dimensional region mask shape changing portion 3503, a three-dimensional region mask position changing portion 3504, a first slice information group acquiring portion 3505, a first slice information group storage portion 3506, a second mesh information acquiring portion 3507, and an object output portion 3508.

The object output portion 3508 includes a second slice information group constituting unit 35081 and an output unit 35082.

In the object information storage portion 3501, 3D voxel information, which is volume texture of a three-dimensional object, is stored. The 3D voxel information is, for example, a collection of two-dimensional images acquired by CT, MRI, PET, or other medical devices. The 3D voxel information is, for example, a collection of two-dimensional images of the inside of the human brain or body captured by CT or MRI. The object information storage portion 3501 is preferably a non-volatile storage medium, but can be implemented also as a volatile storage medium.

The input receiving portion 3502 receives input regarding a second three-dimensional region mask, which is a three-dimensional region mask at the second order. The three-dimensional region mask is information for extracting 3D voxel information, and is information having a three-dimensional geometric shape. The second three-dimensional region mask is three-dimensional mesh information. The three-dimensional mesh information constituting the second three-dimensional region mask is referred to as second mesh information. The three-dimensional mesh information (such as the second mesh information) is a collection of information of points constituting a three-dimensional object. The three-dimensional mesh information is a collection of information of discrete points. The information of the points is typically the coordinate information (x, y, z). The 3D voxel information is, for example, information of a point constituted by (x, y, z, col). Herein, (x, y, z) of (x, y, z, col) represents coordinate information, and "col" represents color information. The 3D voxel information herein is preferably information of points packed without spacing therebetween, but also may be information of discrete points. Furthermore, the input regarding the second three-dimensional region mask is, for example, an instruction to arrange the second three-dimensional region mask in the 3D voxel information. In a case where multiple shapes of second three-dimensional region masks are present, the input regarding the second three-dimensional region mask is, for example, an instruction to select a shape from among these shapes, and to arrange a second three-dimensional region mask with this shape, in the 3D voxel information. Also, the input regarding the second three-dimensional region mask is, for example, an instruction to construct a second three-dimensional region mask in three dimensions, the instruction being input by tracing the profile of a displayed image in three dimensions with input means such as a mouse. Moreover, the input regarding the second three-dimensional region mask is, for example, a shape change instruction or a position change instruction described below. Herein, the input receiving portion 3502 may also receive a shape change instruction, which is an instruction to change the shape of the second three-dimensional region mask. Furthermore, the input receiving portion 3502 may also receive a position change instruction, which is an instruction to change the position of the second three-dimensional region mask. Herein, this information processing apparatus does not have to be capable of specifying the shape or the position of the second three-dimensional region mask. Moreover, the input receiving portion 3502 may receive input of a line-of-sight vector, which is information indicating the direction of a line of sight. The line-of-sight vector is a vector perpendicular to a display screen, and thus the input of the line-of-sight vector is, for example, an instruction to rotate a displayed image in three dimensions. Input means may be any means, such as a keyboard, a mouse (including a 3D mouse), PHANToM, or a menu screen. The input receiving portion 3502 can be implemented, for example, as a device driver for input means such as a mouse, or control software for a menu screen.

If the input receiving portion 3502 receives the shape change instruction, the three-dimensional region mask shape changing portion 3503 changes the shape of the second three-dimensional region mask based on the shape change instruction. The three-dimensional region mask shape changing portion 3503, for example, reduces the size of the second three-dimensional region mask to 90% without changing its centroid, each time the input receiving portion 3502 receives a click of the right button of a mouse serving as the input means. Furthermore, the three-dimensional region mask shape changing portion 3503, for example, enlarges the size of the second three-dimensional region mask to 110% without changing its centroid, each time the input receiving portion 3502 receives a click of the left button of a mouse serving as the input means. Furthermore, if the input receiving portion 3502 receives a signal generated by dragging a mouse serving as the input means, then according to the signal, the three-dimensional region mask shape changing portion 3503 changes the shape of a section (point) for which the instruction with the mouse has been given. The processing performed by the three-dimensional region mask shape changing portion 3503 is well known processing of deforming three-dimensional mesh information, and thus a detailed description thereof has been omitted. Typically, the three-dimensional region mask shape changing portion 3503 can be implemented, for example, as an MPU or a memory. Typically, the processing procedure of the three-dimensional region mask shape changing portion 3503 is implemented by software, and the software is stored in a storage medium such as a ROM. Note that the processing procedure also may be implemented by hardware (dedicated circuit).

If the input receiving portion 3502 receives the position change instruction, the three-dimensional region mask position changing portion 3504 changes the position of the second three-dimensional region mask based on the position change instruction. The phrase "to change the position of the second three-dimensional region mask" refers to an operation of changing the relative position with respect to the first slice information group. In a case where the input means is PHANToM, for example, if the PHANToM is pressed, then the three-dimensional region mask position changing portion 3504 performs processing of moving the second three-dimensional region mask in the deeper direction with respect to the depth of the first slice information group. The processing performed by the three-dimensional region mask position changing portion 3504 is well known processing of changing the position a three-dimensional mesh, and thus a detailed description thereof has been omitted. Typically, the three-dimensional region mask position changing portion 3504 can be implemented, for example, as an MPU or a memory. Typically, the processing procedure of the three-dimensional region mask position changing portion 3504 is implemented by software, and the software is stored in a storage medium such as a ROM. Note that the processing procedure also may be implemented by hardware (dedicated circuit).

The first slice information group acquiring portion 3505 extracts multiple pieces of slice information perpendicular to the line of sight (the line-of-sight vector) and sliced at constant intervals, from the 3D voxel information stored in the object information storage portion 3501, thereby acquiring a first slice information group. The line of sight is, for example, a line that is perpendicular to a display screen on which the object output portion 3508 outputs the first slice information group (the line of sight of a person viewing the display screen). The slice information is a collection of information of points constituting a plane, and the points are packed without spacing therebetween. The first slice information group acquiring portion 3505 does not necessarily have to extract multiple pieces of slice information perpendicular to a line of sight and sliced at constant intervals. However, note that multiple pieces of slice information are preferably perpendicular to the line-of-sight vector. Furthermore, intervals between the pieces of slice information are preferably constant. A smaller interval between the pieces of slice information provides a more precise three-dimensional object to the user. However, note that a smaller interval between the pieces of slice information takes more time in output processing described later. The processing of extracting multiple pieces of slice information in the shape of planes from the 3D voxel information is a well known technique, and thus a detailed description thereof has been omitted. Typically, the first slice information group acquiring portion 3505 can be implemented, for example, as an MPU or a memory. Typically, the processing procedure of the first slice information group acquiring portion 3505 is implemented by software, and the software is stored in a storage medium such as a ROM. Note that the processing procedure also may be implemented by hardware (dedicated circuit).

In the first slice information group storage portion 3506, a first slice information group is stored. The first slice information group is multiple pieces of slice information extracted from the 3D voxel information in the object information storage portion 3501, using a first three-dimensional region mask. The first three-dimensional region mask is a three-dimensional region mask at the first order extracting a three-dimensional object and having a three-dimensional geometric shape. The shape or the position of the first three-dimensional region mask can be changed as in the case of the second three-dimensional region mask, or may be fixed. If the shape or the position can be changed, it is assumed that in order to change the shape or the position of the first three-dimensional region mask, the input receiving portion 3502 receives a change instruction, and the three-dimensional region mask shape changing portion 3503 or the three-dimensional region mask position changing portion 3504 performs the processing, as in the case of the second three-dimensional region mask. The first slice information group in the first slice information group storage portion 3506 is the first slice information group that has been acquired by the first slice information group acquiring portion 3505. Note that the first slice information group may be stored in advance in the first slice information group storage portion 3506. In this case, the first slice information group acquiring portion 3505 is not necessary. The first slice information group storage portion 3506 is preferably a non-volatile storage medium, but can be implemented also as a volatile storage medium.

The second mesh information acquiring portion 3507 acquires second mesh information, which is three-dimensional mesh information constituting the second three-dimensional region mask. As the second mesh information, second mesh information constituting the second three-dimensional region mask regarding which an instruction has been received by the input receiving portion 3502 may be used without any processing. Furthermore, the second mesh information may be second mesh information of the second three-dimensional region mask obtained as a result of processing performed by the three-dimensional region mask shape changing portion 3503 and/or the three-dimensional region mask position changing portion 3504, on second mesh information constituting the second three-dimensional region mask regarding which an instruction has been received by the input receiving portion 3502. It is assumed that if the input receiving portion 3502 receives selection of the shape of the second three-dimensional region mask, mesh information with shapes that can be selected is held in advance in the second mesh information acquiring portion 3507. Typically, the second mesh information acquiring portion 3507 can be implemented, for example, as an MPU or a memory. Typically, the processing procedure of the second mesh information acquiring portion 3507 is implemented by software, and the software is stored in a storage medium such as a ROM. Note that the processing procedure also may be implemented by hardware (dedicated circuit).

The object output portion 3508 determines, for each slice information in the first slice information group, an internal region, which is a region inside the second mesh information, and an external region, which is a region outside the second mesh information, constitutes each slice information such that the internal region and the external region are visually distinguished from each other, acquires a second slice information group in which the internal region and the external region are visually distinguished from each other, and outputs the second slice information group. Herein, the second slice information group is a collection of slice information in which the color information has been corrected such that the internal region and the external region are visually distinguished from each other, for each slice information in the first slice information group. First, the object output portion 3508 typically acquires color information of each point that is contained in the multiple pieces of slice information constituting the first slice information group, and that corresponds to a point in the 3D voxel information stored in the object information storage portion 3501, from the 3D voxel information. Then, the object output portion 3508 processes the color information of a point in the 3D voxel information, in a manner that varies depending on whether this point is a point in the internal region or a point in the external region, and acquires and sets the color information of each point in the multiple pieces of slice information. As a result, the output is performed such that the internal region and the external region are visually distinguished from each other. More specifically, for example, each slice information disposed in a three-dimensional space is extracted by the three-dimensional second mesh information, and the object output portion 3508 typically performs the following processing sequentially on each slice information. The object output portion 3508 calculates a collection of points at the boundary at which the slice information is extracted by the three-dimensional second mesh information (the collection of the points constitutes a closed plane). Then, the object output portion 3508 determines a region inside the closed plane constituted by the collection of the points, as the internal region, and determines a region outside the closed plane, as the external region. Next, the object output portion 3508 determines color information of all the points in the internal region in the slice information. Next, the object output portion 3508 determines color information of all the points in the external region in the slice information. In this case, the object output portion 3508 determines the color information of points in each region such that the internal region and the external region are visually distinguished from each other.

The object output portion 3508 may set, for example, a transparent color for the points in the external region. In this case, only the points in the internal region are displayed, and the user can see only a three-dimensional image in a region defined by the second three-dimensional region mask. Furthermore, in this case, the object output portion 3508 takes, as the color information of the points in the internal region, the color information of points in the 3D voxel information corresponding thereto.

Furthermore, the object output portion 3508 may set, for example, a transparent color for the points in the internal region. In this case, only the points in the external region are displayed, and the user can see only a three-dimensional image from which a region defined by the second three-dimensional region mask has been removed. More specifically, for example, the user can confirm the body portion remaining after extraction in surgeries. In this case, the object output portion 3508 takes, as the color information of the points in the external region, the color information of points in the 3D voxel information corresponding thereto.

Furthermore, the object output portion 3508 may set, for example, the brightness of the points in the internal region to be greater than the brightness of the points in the external region. In this case, the internal region is displayed in a focused manner. In this case, the object output portion 3508 takes, as the color information of all points, the color information of points in the 3D voxel information (having the same positional information) corresponding to these points, and corrects the brightness of the color information. The correction of the brightness is, for example, processing of increasing the brightness of the points in the internal region by 30% and reducing the brightness of the points in the external region by 30%. The processing of correcting the brightness is a well known technique, and thus a detailed description thereof has been omitted. Herein, the term "output" has a concept that includes, for example, displaying on a display screen, printing in a printer, transmission to an external apparatus (such as an apparatus having a display device), and accumulation in a storage medium. The object output portion 3508 may be considered to include, or not to include, an output device such as a display or a loudspeaker. The object output portion 3508 can be implemented, for example, as driver software for an output device, or a combination of driver software for an output device and the output device.

The second slice information group constituting unit 35081 determines color information of the points in each region such that the internal region and the external region are visually distinguished from each other, thereby constituting a second slice information group. The second slice information group constituting unit 35081 typically searches for points in the 3D voxel information having the same positional information as the points in the internal region, and acquires the color information of these points. Next, the second slice information group constituting unit 35081 performs a process on the color information of the points in the internal region and/or the color information of the points in the external region, and determines the color of the points in each region such that the internal region and the external region are visually distinguished from each other. Then, the second slice information group constituting unit 35081 takes the determined color information as the color information of each point, and obtains a second slice information group. Herein, the process is for example, processing of setting a transparent color or changing the brightness described below.

More specifically, for example, the second slice information group constituting unit 35081 sets a transparent color for the points in the external region in each slice information in the first slice information group, thereby constituting a second slice information group. In this case, the second slice information group constituting unit 35081, for example, searches for points in the 3D voxel information having the same positional information as the points in the internal region, and takes the color information of the points obtained by the search, as the color information of the points in the internal region.

Furthermore, for example, the second slice information group constituting unit 35081 sets different color tones for the color of the points in the internal region in each slice information in the first slice information group and the color of the points in the external region in each slice information in the first slice information group, thereby constituting a second slice information group.

Furthermore, for example, the second slice information group constituting unit 35081 sets the brightness of the points in the internal region in each slice information in the first slice information group to be greater than the brightness of the points in the external region in each slice information in the first slice information group, thereby constituting a second slice information group. In this case, typically, the second slice information group constituting unit 35081 obtains the color information other than the brightness of each point, from the color information of a point in the 3D voxel information corresponding thereto.

Furthermore, for example, the second slice information group constituting unit 35081 sets a transparent color for the points in the internal region in each slice information in the first slice information group, thereby constituting a second slice information group. In this case, the second slice information group constituting unit 35081, for example, searches for points in the 3D voxel information having the same positional information as the points in the external region, and takes the color information of the points obtained by the search, as the color information of the points in the external region.

Typically, the second slice information group constituting unit 35081 can be implemented, for example, as an MPU or a memory. Typically, the processing procedure of the second slice information group constituting unit 35081 is implemented by software, and the software is stored in a storage medium such as a ROM. Note that the processing procedure also may be implemented by hardware (dedicated circuit).

The output unit 35082 outputs the second slice information group that has been constituted by the second slice information group constituting unit 35081. The term "output" has a concept that includes, for example, displaying on a display screen, printing in a printer, and transmission to an external apparatus. The output unit 35082 may be considered to include, or not to include, an output device such as a display. The output unit 35082 can be implemented, for example, as driver software for an output device, or a combination of driver software for an output device and the output device.

Next, the operation of the information processing apparatus will be described with reference to the flowchart in FIG. 36.

(Step S3601) The input receiving portion 3502 judges whether or not input has been received. If the input has been received, the procedure proceeds to step S3602. If the input has not been received, the procedure returns to step S3601.

(Step S3602) The input receiving portion 3502 judges whether or not the input that has been received in step S3601 is an instruction to start output. If it is the start instruction, the procedure proceeds to step S3603. If it is not the start instruction, the procedure proceeds to step S3607. Herein, the instruction to start output is, for example, an instruction to start the information processing apparatus.

(Step S3603) The first slice information group acquiring portion 3505 acquires the line-of-sight vector. For example, the line-of-sight vector is stored in advance in the information processing apparatus. The line-of-sight vector is a vector perpendicular to the front face of a three-dimensional object constituted by the 3D voxel information. Herein, the line-of-sight vector may be changed by an instruction from the user. The instruction from the user is, for example, received by the input receiving portion 3502. The line-of-sight vector is changed by rotation of the three-dimensional object that is to be output.

(Step S3604) The first slice information group acquiring portion 3505 reads the 3D voxel information stored in the object information storage portion 3501, and extracts multiple pieces of slice information perpendicular to the line-of-sight vector acquired in step S3603 and sliced at constant intervals, from the 3D voxel information, thereby acquiring a first slice information group. It is assumed that information regarding the intervals at which the slice information is extracted is stored in advance in the first slice information group acquiring portion 3505. The first slice information group acquiring portion 3505, for example, extracts multiple pieces of slice information, from the 3D voxel information in the object information storage portion 3501, using the first three-dimensional region mask that is stored in advance. Herein, the processing of extracting multiple pieces of slice information at predetermined intervals from the 3D voxel information is processing according to a well known technique, and thus a detailed description thereof has been omitted.

(Step S3605) The first slice information group acquiring portion 3505 temporarily accumulates the first slice information group that has been acquired in step S3604, in the first slice information group storage portion 3506.

(Step S3606) The object output portion 3508 outputs the first slice information group that has been acquired in step S3604. With this output, the user can user can see a three-dimensional object. The procedure returns to step S3601.

(Step S3607) The input receiving portion 3502 judges whether or not the input that has been received in step S3601 is input regarding the second three-dimensional mask. If it is the input regarding the second three-dimensional mask, the procedure proceeds to step S3608. If it is not the input regarding the second three-dimensional mask, the procedure proceeds to step S3612.

(Step S3608) The second mesh information acquiring portion 3507 acquires second mesh information, which is three-dimensional mesh information constituting the second three-dimensional mask corresponding to the input.

(Step S3609) The second slice information group constituting unit 35081 acquires the position of the second mesh information. The position of the second mesh information acquired herein is a default position. Herein, information regarding the default position is, for example, stored in advance. The information of the position may be received by the input receiving portion 3502.

(Step S3610) The second slice information group constituting unit 35081 acquires a second slice information group, using the second mesh information that has been acquired in or before step S3609. The processing of acquiring the second slice information group will be described in detail with reference to the flowchart in FIG. 37.

(Step S3611) The output unit 35082 outputs the second slice information group that has been constituted in step S3609. The procedure returns to step S3601.

(Step S3612) The input receiving portion 3502 judges whether or not the input that has been received in step S3601 is a shape change instruction. If it is the shape change instruction, the procedure proceeds to step S3613. If it is not the shape change instruction, the procedure proceeds to step S3614.

(Step S3613) The three-dimensional region mask shape changing portion 3503 changes the shape of the second mesh information, based on the shape change instruction that has been received in step S3612. The processing of changing the shape of the second mesh information is a well known technique (technique according to the finite element method), and thus a detailed description thereof has been omitted. The procedure proceeds to step S3610.

(Step S3614) The input receiving portion 3502 judges whether or not the input that has been received in step S3601 is a position change instruction. If it is the position change instruction, the procedure proceeds to step S3615. If it is not the position change instruction, the procedure returns to step S3601.

(Step S3615) The three-dimensional region mask position changing portion 3504 changes the position of the second mesh information, based on the position change instruction that has been received in step S3614. The processing of changing the position of the second mesh information is a well known technique, and thus a detailed description thereof has been omitted. The procedure proceeds to step S3610.

Note that the processing is ended by powering off or interruption for aborting the processing in the flowchart in FIG. 36.

Next, the processing of acquiring the second slice information group will be described with reference to the flowchart in FIG. 37.

(Step S3701) The second slice information group constituting unit 35081 substitutes 1 for a counter i.

(Step S3702) The second slice information group constituting unit 35081 judges whether or not the $i^{th}$ slice information (unprocessed slice information) is present in the first slice information group. If the $i^{th}$ slice information is present, the procedure proceeds to step S3703. If the $i^{th}$ slice information is not present, the procedure returns to an upper-level function.

(Step S3703) The second slice information group constituting unit 35081 substitutes 1 for a counter j.

(Step S3704) The second slice information group constituting unit 35081 judges whether or not the $j^{th}$ point (unprocessed point) in the $i^{th}$ slice information is present. If the $j^{th}$ point is present, the procedure proceeds to step S3705. If the $j^{th}$ point is not present, the procedure jumps to step S3713. Herein, the term "unprocessed" refers to a state in which no color information has been set.

(Step S3705) The second slice information group constituting unit 35081 acquires the positional information (x, y, z) of the $j^{th}$ point in the $i^{th}$ slice information.

(Step S3706) The second slice information group constituting unit 35081 acquires color information of a point in the 3D voxel information having the positional information that matches the positional information that has been acquired in step S3705.

(Step S3707) The second slice information group constituting unit 35081 judges whether the $j^{th}$ point is a point in the internal region or a point in the external region. This processing is performed, for example, in the following manner. That is to say, the second slice information group constituting unit 35081 calculates all points of intersection between the $i^{th}$ slice information and the second mesh information, in a three-dimensional space (this processing is well known processing). In a case where no such a point of intersection is present, the second slice information group constituting unit 35081 judges that all points in the $i^{th}$ slice information are points in the external region. In a case where only one point of intersection is present, the second slice information group constituting unit 35081 judges that only that one point is a point in the internal region and the other points are points in the external region. In a case where multiple points of intersection are present, the multiple points of intersection constitute a closed plane. If the $j^{th}$ point is a point in this closed plane, the second slice information group constituting unit 35081 judges that this point is a point in the internal region. If the $j^{th}$ point is not a point in this closed plane, the second slice information group constituting unit 35081 judges that this point is a point in the external region. Herein, in a case where all points constituting the boundary of a closed plane are given, the processing of judging whether or not an arbitrary point j is a point in this plane is well known processing, and thus a detailed description thereof has been omitted.

(Step S3708) The second slice information group constituting unit 35081 judges whether or not the $j^{th}$ point is a point in the internal region. If it is a point in the internal region, the procedure proceeds to step S3709. If it is a point in the external region, the procedure proceeds to step S3710.

(Step S3709) The second slice information group constituting unit 35081 performs a process of setting the color information of the $j^{th}$ point, to the color information corresponding to the internal region. Herein, this process also includes processing in which no change is made from the color information that has been acquired in step S3706. Also, the process is, for example, processing of setting a transparent color as the color information. Also, the process is, for example, processing of increasing the brightness of the color information that has been acquired in step S3706. The procedure proceeds to step S3711.

(Step S3710) The second slice information group constituting unit 35081 performs a process of setting the color information of the $j^{th}$ point, to the color information corresponding to the external region. Herein, this process also includes processing in which no change is made from the color information that has been acquired in step S3706. Also, the process is, for example, processing of setting a transparent color as the color information. Also, the process is, for example, processing of reducing the brightness of the color information that has been acquired in step S3706. Herein, the processing in step S3709 is different from the processing in step S3710 (including a case in which no processing is performed "NOP" in one of these steps). The procedure proceeds to step S3711.

(Step S3711) The second slice information group constituting unit 35081 sets the color information after the process, as the color information of the $j^{th}$ point.

(Step S3712) The second slice information group constituting unit 35081 increments the counter j by 1. The procedure proceeds to step S3704.

(Step S3713) The second slice information group constituting unit 35081 increments the counter i by 1. The procedure proceeds to step S3702.

Hereinafter, a specific operation of the information processing apparatus in this embodiment will be described. In this information processing apparatus, a three-dimensional object that is to be output is, for example, the human trunk or head. Such a three-dimensional object can be approximated by a collection of tetrahedrons. Herein, for the sake of simplicity of illustration, first, various data structures will be described using the tetrahedron shown in FIG. 38. In FIG. 38, the four points A, B, C, and O are provided. The point P is a given point inside the tetrahedron.

FIG. 39 shows an example of the data structure of the second mesh information. FIG. 40 shows an example of the data structure of the 3D voxel information. The second mesh information is, for example, a collection of information of points outside and inside the tetrahedron (the points are spaced away from each other). The 3D voxel information is a collection of point information that is information of all points constituting the tetrahedron shown in FIG. 38. The point information at least has the positional information (x, y, z) and the color information (such as "$col_1$" in FIG. 40).

In this status, it is assumed that the user has input a start instruction using input means. The start instruction is input, for example, by turning on the power of this information processing apparatus. Also, in a case where the processing portion of this information processing apparatus is implemented as software, the start instruction is input, for example, by double clicking an iron of this software. Also, the start instruction is input, for example, by selecting the start instruction field on a menu.

Next, the input receiving portion 3502 receives the start instruction.

Next, the first slice information group acquiring portion 3505 acquires a line-of-sight vector that is stored in advance. The line-of-sight vector is a vector perpendicular to a display screen on which a three-dimensional object is displayed.

Next, the first slice information group acquiring portion 3505 reads the 3D voxel information stored in the object information storage portion 3501, and extracts multiple pieces of slice information perpendicular to the line-of-sight vector and sliced at constant intervals, from the 3D voxel information, thereby acquiring a first slice information group. The concept of this processing will be described below. The first slice information group acquiring portion 3505 acquires a first slice information group, which is multiple pieces of slice information that do not have color information, from the 3D voxel information, using the first three-dimensional region mask (mesh information). The first slice information group acquiring portion 3505 acquires a first slice information group, which is multiple pieces of slice information perpendicular to the line-of-sight vector and sliced at predetermined intervals as shown in FIG. 41. The first slice information group acquiring portion 3505 obtains the positions "minD" and "maxD" of the three-dimensional object that is to be displayed, and slices the three-dimensional object at a predetermined interval "D", thereby acquiring multiple pieces of slice information. The slice information is a collection of point information. Furthermore, there is no spacing between the points constituting the slice information. More specifically, a plane represented by the slice information is packed with information of the points. The point information has the positional information (x, y, z), and does not have color information. As a result, the first slice information group acquiring portion 3505 acquires, for example, the first slice information group shown in FIG. 42. The first slice information group has slice information $S_1$, slice information $S_2$, slice information $S_3$, and the like. Herein, the slice information is acquired perpendicularly to the line-of-sight vector, in order to allow even thinned slice information to be viewed in three dimensions by the user viewing a collection of the slice information. Furthermore, slice information that has been thinned out at predetermined intervals is acquired, in order to increase the speed of display processing. The slice information is acquired at constant intervals, in order to display a high-quality three-dimensional object. Next, the first slice information group acquiring portion 3505 acquires the color information of a point in the 3D voxel information having the same positional information as each point. Then, the first slice information group acquiring portion 3505 sets the acquired color information, as the color information of the corresponding point in a slice in the first slice information group. Herein, each point in the slices constituting the first slice information group has the color information.

Next, the first slice information group acquiring portion 3505 temporarily accumulates the acquired first slice information group, in the first slice information group storage portion 3506. Then, the object output portion 3508 outputs the acquired first slice information group.

This processing will be described with a first example using specific medical images. In the first example, the internal region of the second three-dimensional region mask is output in a focused manner. FIG. 43 shows CT images of the human trunk serving as the 3D voxel information. In FIG. 43, there is spacing between the multiple planes (image data), but it is herein assumed that the 3D voxel information is a collection of information of multiple planes packed without spacing therebetween. FIG. 44 shows an example in which the first slice information group acquiring portion 3505 extracts multiple pieces of slice information from the 3D voxel information in FIG. 43, using the first three-dimensional region mask, acquires, for each point in each slice information, the color information of a point in the 3D voxel information corresponding thereto, and constitutes multiple pieces of slice information having the color information that are to be output, and the object output portion 3508 displays the multiple pieces of slice information (first slice information group). Herein, the first three-dimensional region mask is columnar three-dimensional mesh information that is generally in the shape of the trunk. The method for extracting the multiple pieces of slice information from the 3D voxel information is similar to the method for extracting the multiple pieces of slice information in FIG. 42 from the tetrahedron in FIG. 38. The technique for extracting the multiple pieces of slice information from the 3D voxel information is a well known technique, and thus a detailed description thereof has been omitted.

Herein, information processing apparatus can also perform processing of increasing the transmission from the displayed state in FIG. 44 to the displayed state as in FIG. 45. In order to increase the transmission, the input receiving portion 3502 receives an instruction to increase the transmission, and an unshown transmission changing unit changes the color information of each point in each first slice information so as to increase the transmission. Herein, processing of changing the color information so as to increase the transmission is a well known technique, and thus a detailed description thereof has been omitted. With increased transmission of each point, the user can more easily recognize an organ (such as the heart) inside the trunk.

Next, it is assumed that the user has given an instruction to input a spherical second three-dimensional mask.

Then, the input receiving portion 3502 receives the input. Then, the second mesh information acquiring portion 3507 acquires second mesh information constituting the spherical second three-dimensional mask. The spherical second mesh information is information constituted by a collection of points in a part of the surface of the sphere. It is assumed that this second mesh information is, for example, held in advance in the information processing apparatus.

Next, the second slice information group constituting unit 35081 acquires the position of the second mesh information. Herein, the position of the second mesh information is, for example, determined in the following manner. That is to say, it is assumed that the center of the sphere of the second mesh information matches the position of the centroid of the three-dimensional object constituted by the displayed first slice information group in FIG. 44. Then, the second slice information group constituting unit 35081 calculates the position of the centroid, takes the position as the position of the center of the sphere, and determines the position of the second mesh information.

Next, in the following manner, the second slice information group constituting unit 35081 acquires a second slice information group. That is to say, the second slice information group constituting unit 35081 performs the following processing sequentially from the slice information at the first order. The second slice information group constituting unit 35081 acquires the positional information of each point constituting each slice information. Then, the color information of a point that matches the positional information and that is contained in the 3D voxel information is acquired (if the slice information constituting the first slice information group has color information, the color information also may be used). Next, the second slice information group constituting unit 35081 judges whether a point that is to be processed is inside (internal region) or outside (external region) the three-dimensional shape of the second mesh information. The concept of this processing will be described with reference to FIG. 46. In FIG. 46A, one piece of slice information in a first slice information group, from a hexahedron that is a collection of CT images, is denoted by 4601. Then, the user, for example, inputs an instruction to input a columnar second three-dimensional mask, and an instruction of its position. Then, the second slice information group constituting unit 35081 acquires the columnar second mesh information, and arranges a columnar three-dimensional object at a position according to the instruction from the user (FIG. 46A). Then, the second slice information group constituting unit 35081 determines whether each point in the slice information is a point in the internal region or a point in the external region of the column, based on the columnar second mesh information, as shown in FIG. 46B. In FIG. 46, the second slice information group constituting unit 35081 extracts the internal region of the column.

Herein, if points are present in the internal region, the second slice information group constituting unit 35081, for example, increases the brightness of the points by 50%. On the other hand, if points are present in the external region, the second slice information group constituting unit 35081, for example, reduces the brightness of the points by 30%.

Then, the second slice information group constituting unit 35081 performs this processing on all slice information constituting the second slice information group, namely all points therein, and sets the color information of all points. With the above-described processing, the second slice information group constituting unit 35081 can acquire a second slice information group.

Next, the output unit 35082 displays the second slice information group that has been constituted by the second slice information group constituting unit 35081. FIG. 47 shows an example of this display. In FIG. 47, a central three-dimensional region (in the shape of a sphere) in which there are many organs is focused.

Next, it is assumed that the user has input an instruction to deform and an instruction to move the spherical second three-dimensional mask, using input means. Next, the input receiving portion 3502 receives the shape change instruction and the position change instruction. The shape change instruction and the position change instruction are, for example, instructions to perform fine control on the shape (size) and the position of the spherical second three-dimensional mask, using a mouse and a slider bar (the slider bar is a component used on a GUI, and is a bar for setting a value in a range). Furthermore, it is preferable that based on the shape change instruction, the spherical shape is changed into a shape that is close to an organ and that is generally in the shape of the organ. Herein, it is not necessary that based on this instruction, the spherical shape is changed to completely match the shape of the organ.

Next, the three-dimensional region mask shape changing portion 3503 and the three-dimensional region mask position changing portion 3504 change the shape and the position of the second mesh information, based on the shape change instruction and the position change instruction. Herein, the processing of changing the shape or the position of three-dimensional mesh information based on an instruction from the user (instruction from a mouse or the like) is a well known technique (the finite element method).

Next, as in the above-described manner, the second slice information group constituting unit 35081 acquires a second slice information group, using the deformed second mesh information. The method for determining the color information of each point in each slice information constituting the second slice information group is similar to the above (processing in the case of outputting the image in FIG. 47).

Next, the output unit 35082 displays the constituted second slice information group. FIG. 48 shows an example of this display. In FIG. 48, the positional relationship, shape, and surface properties of the main artery, myocardium, and pulmonary artery that are regions of interest are rendered.

Next, a second example using medical images will be described. In the second example, only the internal region of the second three-dimensional region mask is output. FIG. 49 shows results obtained by processing 3D voxel information of the human head captured by MRI or other medical devices, with this information processing apparatus.

First, it is assumed that the input receiving portion 3502 in this information processing apparatus receives an instruction from the user to perform profile extraction of the outline of the head. The user gives this instruction, for example, by tracing the profile of the displayed head with a mouse.

Next, the input receiving portion 3502 receives the instruction to extract the profile given with the mouse. Next, the information processing apparatus constructs second mesh information (number of elements: 1263) from multiple pieces of coordinate information through which the mouse cursor passed. The processing of constructing the second mesh information from the multiple pieces of coordinate information through which the mouse cursor passed is a well known technique, and thus a detailed description thereof has been omitted. Next, the second slice information group constituting unit 35081 acquires a second slice information group, based on the constructed second mesh information, by processing similar to the above-described processing. Then, the output unit 35082 outputs the second slice information group. FIG. 49A shows the output result. FIG. 49A shows the output of the shape of the head without any processing.

Next, it is assumed that the user, for example, inputs an instruction to reduce the size of the second mesh information while keeping its shape. This input is performed, for example, by pressing "reduction" button (not shown) on a control panel. Then, the three-dimensional region mask shape changing portion 3503 makes the second mesh information smaller by a predetermined ratio, thereby obtaining new second mesh information. Next, the second slice information group constituting unit 35081 acquires a second slice information group, using the new second mesh information, by the above-described processing. At that time, each slice information constituting the second slice information group, a transparent color is set for the points in the external region, and thus only the points in the internal region are output. FIG. 49B shows an example of this output.

Next, it is assumed that the user again inputs an instruction to reduce the size of the second mesh information while keeping its shape. Then, the three-dimensional region mask shape changing portion 3503 makes the second mesh information further smaller by a predetermined ratio, thereby obtaining new second mesh information. Next, the second slice information group constituting unit 35081 acquires a new second slice information group, using the new second mesh information. At that time, in each slice information constituting the second slice information group, a transparent color is set for the points in the external region, and thus only the points in the internal region are output. FIG. 49C shows an example of this output. As shown in FIGS. 49A to 49C, as the size of the second mesh information is smaller, the visible region is changed not to include the scalp/skull, and thus wrinkles in the brain included in the internal structure appear.

FIG. 49D shows an example of output viewing the head from above. The user changes the line-of-sight vector by inputting an instruction to rotate the head, and thus the image in FIG. 49D is output. The output algorithm in FIG. 49D is the same as the output algorithm in FIG. 49A and the like. According to the description above, if the shape of the second three-dimensional region mask is controlled according to the purpose, the interior of the human body, the surface of an organ, and the like can be effectively visualized with a simple manipulation. According to this information processing apparatus, results of a change in the visible region are rendered in real-time, and thus an interactive manipulation is possible.

Next, a third example using medical images will be described. In the third example, only the external region of the second three-dimensional region mask is output. In a case where only the external region is output, a three-dimensional image from which a predetermined section has been removed can be confirmed according to the manner in which the internal region is specified (the shape or the position of the second three-dimensional region mask), and the user can see the state in which a scalpel has been put or a hole has been made with a drill or the like in surgeries.

FIG. 50 shows an example in which a first slice information group is acquired using a first three-dimensional region mask, from the 3D voxel information of the human trunk, and the first slice information group is output. Herein, the first three-dimensional region mask is three-dimensional mesh information that is generally in the shape of the trunk.

It is then assumed that the user inputs, for example, a spherical second three-dimensional region mask. It is then assumed that the user gives an instruction to change the shape and the position of the second three-dimensional region mask.

Next, the input receiving portion 3502 receives the input from the user. Then, the three-dimensional region mask shape changing portion 3503 and the three-dimensional region mask position changing portion 3504 change the default shape and position of the sphere, based on the shape change instruction and the position change instruction from the user. Then, the second mesh information acquiring portion 3507 acquires second mesh information of a new second three-dimensional region mask.

Next, the second slice information group constituting unit 35081 sets the color information of each slice information constituting the second slice information group, based on the new second mesh information, such that the internal region is transparent and the external region has the color of the 3D voxel information. Then, the second slice information group constituting unit 35081 constitutes a second slice information group constituted by multiple pieces of slice information in which only the external regions are visible.

Next, the output unit 35082 outputs the second slice information group that has been constituted by the second slice information group constituting unit 35081. FIG. 51 shows an example of this output. In FIG. 51, a hole can be confirmed at a part (in the vicinity of the center of the trunk) of the trunk in FIG. 50. With this display, the user (such as a surgeon) can perform surgical simulation and preoperative planning before the surgery.

Herein, FIG. 52 shows an example of a user interface (input screen) in this information processing apparatus. In FIG. 52, the "Total" field represents a field of the number of all three-dimensional region masks (including the first three-dimensional region mask and the second three-dimensional region mask). In this embodiment, a case was described in which one first three-dimensional region mask and one second three-dimensional region mask are provided, but multiple second three-dimensional region masks may be provided. The processing in this case will be described in Embodiment 5. In FIG. 52, "Select" field represents the ID of a three-dimensional region mask that is to be processed. The term "processing" used with respect to a three-dimensional region mask that is to be processed refers to processing described below, such as setting the color (RGB) of the three-dimensional region mask, changing the shape and the position of the three-dimensional region mask, and changing the transparency of an output image. In FIG. 52, the bars "R", "G", and "B" are slider bars for setting the color of the three-dimensional region mask (including the first three-dimensional region mask and the second three-dimensional region mask). In FIG. 52, "Alpha" represents a slider bar for setting the transparency of an output image. Furthermore, "Scale" represents a slider bar for setting the size of the three-dimensional region mask (for inputting a shape change instruction). Moreover, "Zoom" represents a slider bar for setting the position of the three-dimensional region mask (for inputting a position change instruction).

As described above, according to this embodiment, it is possible to flexibly and interactively refer to a three-dimensional region of interest on an image such as a medical image. Accordingly, for example, this information processing apparatus can assist surgical simulation, preoperative planning, and the like.

Herein, according to this embodiment, the operation of the information processing apparatus was described mainly using medical images, but it will be appreciated that the information processing apparatus can be used for other images. The same is applied to other embodiments.

Furthermore, according to this embodiment, the 3D voxel information was a collection of images acquired by a medical device (such as CT or MRI), but it will be appreciated that the 3D voxel information also may be information acquired by other means. The same is applied to other embodiments.

Furthermore, in this embodiment, the information processing apparatus does not have to include the first slice information group acquiring portion. In this case, in the information processing apparatus, the first slice information group is stored in advance. Herein, it is preferable that each time the information processing apparatus receives a change of the line-of-sight vector such as rotation of the displayed three-dimensional object, the first slice information group acquiring portion dynamically acquires a first slice information group having slice information perpendicular to the line-of-sight vector.

The processing in this embodiment may be implemented by software. The software may be distributed by software downloading or the like. The software may be distributed in the form where the software is stored in a storage medium such as a CD-ROM. Note that the same is applied to the other embodiments described in this specification. The software that implements the information processing apparatus in this embodiment may be a following program. Specifically, this program is a program for causing a computer to execute the following steps, wherein in the computer, 3D voxel information and a first slice information group are stored, the first slice information group being multiple pieces of slice information obtained as a result of extraction from the 3D voxel information using a first three-dimensional region mask, which is a three-dimensional region mask extracting the 3D voxel information and having a three-dimensional geometric shape, the steps including: an input receiving step of receiving input regarding a second three-dimensional region mask, which is a three-dimensional region mask at the second order, a second mesh information acquiring step of acquiring second mesh information, which is three-dimensional mesh information constituting the second three-dimensional region mask, and an object output step of determining an internal region, which is a region inside the second mesh information, and an external region, which is a region outside the second mesh information, for each slice information in the first slice information group, based on the second mesh information, and outputting the first slice information group such that the internal region and the external region are visually distinguished from each other. Herein, the 3D voxel information is typically information acquired by capturing with a medical device.

Furthermore, in this program, the object output step may comprise: a second slice information group constituting step of setting a transparent color for points in the external region in each slice information in the first slice information group, thereby constituting a second slice information group; and an output step of outputting the second slice information group that has been constituted in the second slice information group constituting step.

Furthermore, in this program, the object output step may comprise: a second slice information group constituting step of setting different color tones for the color of points in the internal region in each slice information in the first slice information group and the color of points in the external region in each slice information in the first slice information group, thereby constituting a second slice information group; and an output step of outputting the second slice information group that has been constituted in the second slice information group constituting step. Herein, the phrase "color tones are different" also refers to states in which colors are different, brightnesses are different, and the like.

Furthermore, in this program, the object output step may comprise: a second slice information group constituting step of setting a transparent color for points in the internal region in each slice information in the first slice information group, thereby constituting a second slice information group; and an output step of outputting the second slice information group that has been constituted in the second slice information group constituting step.

Furthermore, in this program, it is preferable that the shape of a three-dimensional object corresponding to an instruction received in the input receiving step is generally in the shape of an organ.

Furthermore, in this program, it is preferable that in the input receiving step, a shape change instruction, which is an instruction to change the shape of the second three-dimensional region mask is received, and the computer is caused to further execute a three-dimensional region mask shape changing step of changing the shape of the second three-dimensional region mask based on the shape change instruction.

Furthermore, in this program, it is preferable that in the input receiving step, a position change instruction, which is an instruction to change the position of the second three-dimensional region mask is received, and the computer is caused to further execute a three-dimensional region mask position changing step of changing the position of the second three-dimensional region mask based on the position change instruction.

Furthermore, in this program, it is preferable that the computer is caused to further execute a first slice information group acquiring step of extracting multiple pieces of slice information perpendicular to a line of sight and sliced at constant intervals, from the 3D voxel information, thereby acquiring a first slice information group.

Embodiment 5

FIG. 53 is a block diagram of the information processing apparatus in this embodiment.

The information processing apparatus includes the object information storage portion 3501, an input receiving portion 5302, the three-dimensional region mask shape changing portion 3503, the three-dimensional region mask position changing portion 3504, the first slice information group acquiring portion 3505, the first slice information group storage portion 3506, a second mesh information acquiring portion 5307, and an object output portion 5308.

The object output portion 5308 includes a second slice information group constituting unit 53081 and an output unit 53082.

The input receiving portion 5302 receives input regarding two or more second three-dimensional region masks. Furthermore, the input receiving portion 5302 also receives a shape change instruction, which is an instruction to change the shape of the second three-dimensional region mask. Furthermore, the input receiving portion 5302 also receives a position change instruction, which is an instruction to change the position of the second three-dimensional region mask. Moreover, the input receiving portion 5302 may receive input of a line-of-sight vector, which is information indicating the direction of a line of sight. Input means may be any means, such as a keyboard, a mouse (including a 3D mouse), PHANToM, or a menu screen. The input receiving portion 5302 can be implemented, for example, as a device driver for input means such as a mouse, or control software for a menu screen.

The second mesh information acquiring portion 5307 acquires two or more pieces of second mesh information constituting the two or more second three-dimensional region masks. Typically, the second mesh information acquiring portion 5307 can be implemented, for example, as an MPU or a memory. Typically, the processing procedure of the second mesh information acquiring portion 5307 is implemented by software, and the software is stored in a storage medium such as a ROM. Note that the processing procedure also may be implemented by hardware (dedicated circuit).

The object output portion 5308 divides each slice information in the first slice information group into multiple regions, according to the two or more pieces of second mesh information, and outputs the first slice information group such that the multiple regions are visually distinguished from each other. Herein, the term "output" has a concept that includes, for example, displaying on a display screen, printing in a printer, and transmission to an external apparatus. The object output portion 5308 may be considered to include, or not to include, an output device such as a display. The object output portion 5308 can be implemented, for example, as driver software for an output device, or a combination of driver software for an output device and the output device.

The second slice information group constituting unit 53081 determines the color of points in each region, based on the color corresponding to the one or more second three-dimensional region masks constituting each region, constitutes multiple pieces of slice information, which is a collection of points having the color, and acquires a second slice information group, which is the multiple pieces of slice information. Typically, the second slice information group constituting unit 53081 can be implemented, for example, as an MPU or a memory. Typically, the processing procedure of the second slice information group constituting unit 53081 is implemented by software, and the software is stored in a storage medium such as a ROM. Note that the processing procedure also may be implemented by hardware (dedicated circuit).

Next, the operation of the information processing apparatus will be described. The operation of this information processing apparatus is different from the operation of the information processing apparatus in the flowchart in FIG. 36, in the processing of acquiring a second slice information group in step S3610. Except for that, the operations are the same. Herein, this information processing apparatus receives input regarding the second three-dimensional mask twice or more. More specifically, in this information processing apparatus, the processing in step S3607 is performed twice or more.

Next, the processing of acquiring a second slice information group in this information processing apparatus will be described with reference to the flowchart in FIG. 54.

(Step S5401) The second slice information group constituting unit 53081 judges the region of the $j^{th}$ point. The phrase "to judge the region" refers to processing of judging which region includes the $j^{th}$ point, among the regions that have been divided by the two or more second three-dimensional region masks. The processing of judging the region of the $j^{th}$ point will be described in detail with reference to the flowchart in FIG. 55.

(Step S5402) The second slice information group constituting unit 53081 processes the color information that has been acquired in step S3706, to the color information corresponding to the region that has been determined in step S5401.

Next, the processing of judging the region of the $j^{th}$ point in this information processing apparatus will be described with reference to the flowchart in FIG. 55.

(Step S5501) The second slice information group constituting unit 53081 substitutes 1 for a counter i.

(Step S5502) The second slice information group constituting unit 53081 judges whether or not the $i^{th}$ second three-dimensional mask is present. If the $i^{th}$ second three-dimensional mask is present, the procedure proceeds to step S5503. If the $i^{th}$ second three-dimensional mask is not present, the procedure returns to an upper-level function.

(Step S5503) The second slice information group constituting unit 53081 acquires second mesh information of the $i^{th}$ second three-dimensional mask. The second mesh information of the second three-dimensional mask is held in the information processing apparatus after the user performed input regarding the second three-dimensional mask, and thus this second mesh information is read.

(Step S5504) The second slice information group constituting unit 53081 judges whether the $j^{th}$ point is a point in the internal region or a point in the external region of the second mesh information that has been acquired in step S5503. This processing is similar to the processing in step S3707.

(Step S5505) The second slice information group constituting unit 53081 stores the result of the judgment in step S5504. The result is stored, not by overwriting the result on a result of judgment regarding whether the $j^{th}$ point is a point in the internal region or a point in the external region of the second mesh information corresponding to a second three-dimensional mask that is not at the $i^{th}$ order, but by additionally writing the result thereto. FIG. 56 shows an example of a data structure diagram of region information, which is information in which such a judgment result is stored. In FIG. 56, if the bit of the region information of the $j^{th}$ point is "1", the $j^{th}$ point is in the internal region of the corresponding second three-dimensional mask. Furthermore, if the bit is 0", the $j^{th}$ point is in the external region of the corresponding second three-dimensional mask. The region information in FIG. 56 is "1, 0, 1, 1, . . . ", and thus the $j^{th}$ point is in the internal region of the second mask region at the first order, in the external region of the second mask region at the second order, in the internal region of the second mask region at the third order, and in the internal region of the second mask region at the fourth order. The color information of the $j^{th}$ point is determined based on this region information. Furthermore, it will be appreciated that the color information of the $j^{th}$ point is determined also using the color information that has been acquired in step S3706.

(Step S5506) The second slice information group constituting unit 53081 increments the counter i by 1. The procedure returns to step S5502.

Hereinafter, a specific operation of the information processing apparatus in this embodiment will be described.

It is herein assumed that in this information processing apparatus, 3D voxel information of the trunk is stored in the object information storage portion 3501. It is then assumed that the information processing apparatus has displayed the first slice information group shown in FIG. 44, by the processing described in Embodiment 4. Next, it is assumed that the user has changed the transmission (adjusted the "Alpha" slider bar in FIG. 52), and the information processing apparatus has displayed the first slice information group in FIG. 45.

Next, it is assumed that the user has given an instruction to input three spherical second three-dimensional region masks having three primary colors, namely red, green, and blue. Then, this information processing apparatus receives this instruction, and determines each point in each slice information constituting the first slice information group is in the internal region or in the external region of each of the three second three-dimensional region masks. Then, for points in the internal region of the red second three-dimensional region mask, R color information is increased by a predetermined amount (information of the "predetermined amount" is stored in advance). Furthermore, for points in the internal region of the green second three-dimensional region mask, G color information is increased by a predetermined amount (stored in advance). Moreover, for points in the internal region of the blue second three-dimensional region mask, B color information is increased by a predetermined amount (stored in advance). Then, for example, points in both of the internal regions of the two second three-dimensional region masks having red and blue colors are displayed in a purple-tinged color.

FIG. 57 shows an example of this output. In FIG. 57, the three spherical second three-dimensional region masks having red, green, and blue colors have been input, and the regions that have been divided by the three second three-dimensional region masks are displayed such that they are visually distinguished from each other. Herein, the processing in this embodiment is similar processing except for the manner in which the color of each point in the slice information is determined.

As described above, according to this embodiment, it is possible to flexibly and interactively refer to multiple three-dimensional regions of interest on an image such as a medical image. Accordingly, for example, this information processing apparatus can more easily assist surgical simulation, preoperative planning, and the like.

The processing in this embodiment may be implemented by software. The software may be distributed by software downloading or the like. The software may be distributed in the form where the software is stored in a storage medium such as a CD-ROM. Note that the same is applied to the other embodiments described in this specification. The software that implements the information processing apparatus in this embodiment may be a following program. Specifically, this program is a program for causing a computer to execute the following steps, wherein in the computer, 3D voxel information acquired by capturing with a medical device and a first slice information group are stored, the first slice information group being multiple pieces of slice information obtained as a result of extraction from the 3D voxel information using a first three-dimensional region mask, which is a three-dimensional region mask extracting the 3D voxel information and having a three-dimensional geometric shape, the steps including: an input receiving step of receiving input regarding a second three-dimensional region mask, which is a three-dimensional region mask at the second order; a second mesh information acquiring step of acquiring second mesh information, which is three-dimensional mesh information constituting the second three-dimensional region mask; and an object output step of determining an internal region, which is a region inside the second mesh information, and an external region, which is a region outside the second mesh information, for each slice information in the first slice information group, based on the second mesh information, and outputting the first slice information group such that the internal region and the external region are visually distinguished from each other.

Furthermore, in this program, in the input receiving step, input regarding at least two second three-dimensional region masks may be received, in the second mesh information acquiring step, at least two pieces of second mesh information constituting the at least two second three-dimensional region masks may be acquired, and in the object output step, each slice information in the first slice information group may be divided into multiple regions according to the at least two pieces of second mesh information, and the first slice information group may be output such that the multiple regions are visually distinguished from each other.

Furthermore, in this program, colors corresponding to the at least two second three-dimensional region masks may be present, and the object output step may comprise: a second slice information group constituting step of determining color of points in each of the regions, based on the color corresponding to the at least one second three-dimensional region mask constituting each of the regions, constituting multiple pieces of slice information, which is a collection of points having the color, and acquiring a second slice information group, which is the multiple pieces of slice information; and an output step of outputting the second slice information group that has been constituted in the second slice information group constituting step.

Embodiment 6

In this embodiment, an information processing apparatus and the like for generating a DRR (digitally reconstructed radiograph) from CT data or the like will be described.

FIG. 58 is a block diagram of the information processing apparatus in this embodiment.

The information processing apparatus includes a receiving portion 5801, an object information storage portion 5802, a first slice information group storage portion 5803, an origin information storage portion 5804, a first slice information group acquiring portion 5805, a second slice information group acquiring portion 5806, a magnification calculating portion 5807, a third slice information group acquiring portion 5808, an output portion 5809, and a setting portion 5810. Furthermore, the output portion 5809 includes a synthesizing unit 58091 and an output unit 58092.

The receiving portion 5801 receives input from the user. Herein, for example, a line-of-sight vector specifying a line of sight, transparency information, a command to start the information processing apparatus, an instruction to move origin information, and other various instructions and data are input. The transparency information is information of the transparency of a point constituting slice information, and typically referred to as an alpha value. Input means may be any means, such as a keyboard, a mouse, or a menu screen. The receiving portion 5801 can be implemented, for example, as a device driver for input means such as a keyboard, or control software for a menu screen.

In the object information storage portion 5802, 3D voxel information, which is volume texture of a three-dimensional object, is stored. The 3D voxel information is, for example, collection of two-dimensional images acquired by CT, MRI, PET, or other medical devices. The 3D voxel information is, for example, information of a point constituted by (x, y, z, col, α value). The object information storage portion 5802 is preferably a non-volatile storage medium, but can be implemented also as a volatile storage medium.

In the first slice information group storage portion 5803, a first slice information group having multiple pieces of first slice information is stored, the first slice information being slice information that is information constituted based on two-dimensional image data obtained as a result of extraction with multiple planes from 3D voxel information, which is volume texture of a three-dimensional object, and being constituted by information of multiple points having positional information, which is information indicating position. Herein, the first slice information group in the first slice information group storage portion 5803 may be prepared in advance. In this case, in the information processing apparatus, the first slice information group acquiring portion 5805 is not necessary. Furthermore, the points constituting the slice information may have elasticity information, which is information of elasticity, color information, and transparency information. The first slice information group storage portion 5803 may be a non-volatile storage medium, or may be a volatile storage medium.

In the origin information storage portion 5804, origin information, which is information indicating the position of an origin of X-ray irradiation, is stored. The origin information is, for example, the coordinate values (x, y, z) in a three-dimensional space. The origin information storage portion 5804 may be a non-volatile storage medium, or may be a volatile storage medium. The origin information may be fixed, or may be customizable.

The first slice information group acquiring portion 5805 extracts multiple pieces of first slice information perpendicular to a line of sight and sliced at constant intervals, from the 3D voxel information stored in the object information storage portion 5802, thereby acquiring a first slice information group, and at least temporarily stores the first slice information group in the first slice information group storage portion 5803. The phrase "perpendicular to a line of sight" refers to a state of being perpendicular to a line-of-sight vector, which is a vector perpendicular to a screen on which a three-dimensional object is displayed. Herein, the slice information is a collection of information of points constituting a plane, and, typically, the points are packed without spacing therebetween. Typically, the first slice information group acquiring portion 5805 can be implemented, for example, as an MPU or a memory. Typically, the processing procedure of the first slice information group acquiring portion 5805 is implemented by software, and the software is stored in a storage medium such as a ROM. Note that the processing procedure also may be implemented by hardware (dedicated circuit).

The second slice information group acquiring portion 5806 performs extraction from each of two or more pieces of first slice information, perpendicularly to each of the multiple pieces of first slice information and radially from the position indicated by the origin information, using arrangement information of each of the multiple pieces of first slice information, thereby acquiring multiple pieces of second slice information. The arrangement information of each first slice information may be information obtained from the coordinate information contained in the information of a point on the first slice information, or may be the order in which the first slice information is stored in the first slice information group storage portion 5803. More specifically, any arrangement information may be used that indicates the distance between each of the multiple pieces of first slice information and the position indicated by the origin information. Typically, the second slice information group acquiring portion 5806 can be implemented, for example, as an MPU or a memory. Typically, the processing procedure of the second slice information group acquiring portion 5806 is implemented by software, and the software is stored in a storage medium such as a ROM. Note that the processing procedure also may be implemented by hardware (dedicated circuit). Herein, each of the two or more pieces of first slice information is preferably an image including the chest. In this case, a DRR of the chest that is highly useful can be easily obtained.

The magnification calculating portion 5807 calculates, for each of the multiple pieces of second slice information, a magnification that is an enlargement ratio or reduction ratio of the second slice information, using arrangement information of the second slice information. Herein, the magnification calculating portion 5807 may use the magnification "1" in which neither enlargement nor reduction is performed. An example of a specific method of calculation performed by the magnification calculating portion 5807 will be described later. Typically, the magnification calculating portion 5807 can be implemented, for example, as an MPU or a memory. Typically, the processing procedure of the magnification calculating portion 5807 is implemented by software, and the software is stored in a storage medium such as a ROM. Note that the processing procedure also may be implemented by hardware (dedicated circuit).

The third slice information group acquiring portion 5808 enlarges or reduces each of the multiple pieces of second slice information according to the magnification that has been calculated by the magnification calculating portion 5807, thereby acquiring multiple pieces of third slice information. The processing of enlarging or reducing an image is a well known technique. Typically, the third slice information group acquiring portion 5808 can be implemented, for example, as an MPU or a memory. Typically, the processing procedure of the third slice information group acquiring portion 5808 is implemented by software, and the software is stored in a storage medium such as a ROM. Note that the processing procedure also may be implemented by hardware (dedicated circuit).

The output portion 5809 outputs the multiple pieces of third slice information in a superimposed manner. Herein, the term "output" has a concept that includes, for example, displaying on a display screen, printing in a printer, transmission to an external apparatus, and accumulation in a storage medium. The output portion 5809 may be considered to include, or not to include, an output device such as a display. The output portion 5809 can be implemented, for example, as driver software for an output device, or a combination of driver software for an output device and the output device.

The synthesizing unit 58091 superimposes the multiple pieces of third slice information on a two-dimensional plane, thereby obtaining one image. Herein, the processing of superimposing multiple images, thereby acquiring one image is a well known technique, and thus a detailed description thereof has been omitted. Typically, the synthesizing unit 58091 can be implemented, for example, as an MPU or a memory. Typically, the processing procedure of the synthesizing unit 58091 is implemented by software, and the software is stored in a storage medium such as a ROM. Note that the processing procedure also may be implemented by hardware (dedicated circuit).

The output unit 58092 outputs the images on the two-dimensional plane that have been superimposed by the synthesizing unit 58091. The output unit 58092 may be considered to include, or not to include, an output device such as a display. The output unit 58092 can be implemented, for example, as driver software for an output device, or a combination of driver software for an output device and the output device.

The setting portion 5810 stores the origin information that has been received by the receiving portion 5801, in the origin information storage portion 5804, and updates the transparency information that has been received by the receiving portion 5801, as the transparency information of points constituting the first slice information, the second slice information, or the third slice information, for example. Typically, the setting portion 5810 can be implemented, for example, as an MPU or a memory. Typically, the processing procedure of the setting portion 5810 is implemented by software, and the software is stored in a storage medium such as a ROM. Note that the processing procedure also may be implemented by hardware (dedicated circuit).

Next, the operation of the information processing apparatus will be described with reference to the flowcharts in FIGS. 59 and 60.

(Step S5901) The receiving portion 5801 judges whether or not input from the user has been received. If the input has been received, the procedure proceeds to step S5902. If the input has not been received, the procedure returns to step S5901.

(Step S5902) The receiving portion 5801 judges whether or not an instruction to output a DRR has been received. The instruction to output a DRR is, for example, input by the user pressing a button on the GUI with a mouse. If the instruction to output a DRR has been received, the procedure proceeds to step S5903. If the instruction to output a DRR has not been received, the procedure proceeds to step S5904.

(Step S5903) The second slice information group acquiring portion 5806, the output portion 5809, and the like perform processing of outputting a DRR. The processing of outputting a DRR will be described in detail with reference to the flowchart in FIG. 60. The procedure returns to step S5901.

(Step S5904) The receiving portion 5801 judges whether or not input of origin information has been received. If the input of origin information has been received, the procedure proceeds to step S5905. If the input of origin information has not been received, the procedure proceeds to step S5906.

(Step S5905) The setting portion 5810 accumulates the received origin information, in the origin information storage portion 5804.

(Step S5906) The receiving portion 5801 judges whether or not input of transparency information has been received. If the input of transparency information has been received, the procedure proceeds to step S5907. If the input of transparency information has not been received, the procedure proceeds to step S5911.

(Step S5907) The setting portion 5810 updates the transparency information of each point in each slice information, in the first slice information group in the first slice information group storage portion 5803, the second slice information group that has been acquired by the second slice information group acquiring portion 5806, and the third slice information group that has been acquired by the third slice information group acquiring portion 5808, to the received transparency information. Herein, neither the second slice information group that has been acquired by the second slice information group acquiring portion 5806 nor the third slice information group that has been acquired by the third slice information group acquiring portion 5808 is present on a memory, only the transparency information of the first slice information group is updated.

(Step S5908) The output portion 5809 judges whether or not a DRR is being output. If a DRR is being output, the procedure proceeds to step S5909. If no DRR is being output, the procedure returns to step S5901.

(Step S5909) The synthesizing unit 58091 superimposes all third slice information, thereby obtaining a two-dimensional image (DRR).

(Step S5910) The output unit 58092 outputs the image (DRR) that has been obtained in step S5909. The procedure returns to step S5901.

(Step S5911) The receiving portion 5801 judges whether or not an instruction to acquire a first slice information group has been received. If the instruction to acquire a first slice information group has been received, the procedure proceeds to step S5912. If the instruction to acquire a first slice information group has not been received, the procedure returns to step S5901.

(Step S5912) The first slice information group acquiring portion 5805 extracts multiple pieces of first slice information perpendicular to a line of sight and sliced at constant intervals, from the 3D voxel information stored in the object information storage portion 5802, thereby acquiring a first slice information group. This processing is a well known technique, and thus a detailed description thereof has been omitted.

(Step S5913) The first slice information group acquiring portion 5805 accumulates the first slice information group that has been acquired in step S5912, in the first slice information group storage portion 5803. The procedure returns to step S5901.

Note that the processing is ended by powering off or interruption for aborting the processing in the flowchart in FIG. 59.

Next, the processing of outputting a DRR will be described with reference to the flowchart in FIG. 60.

(Step S6001) The second slice information group acquiring portion 5806 reads origin information, from the origin information storage portion 5804.

(Step S6002) The second slice information group acquiring portion 5806 substitutes 1 for a counter i.

(Step S6003) The second slice information group acquiring portion 5806 judges whether or not the $i^{th}$ first slice information is stored in the first slice information group storage portion 5803. If the $i^{th}$ first slice information is stored, the procedure proceeds to step S6004. If the $i^{th}$ first slice information is not stored, the procedure proceeds to step S6011.

(Step S6004) The second slice information group acquiring portion 5806 reads the $i^{th}$ first slice information, from the first slice information group storage portion 5803.

(Step S6005) The second slice information group acquiring portion 5806 performs extraction from the $i^{th}$ first slice information that has been read in step S6004, perpendicularly to the $i^{th}$ first slice information and radially from the position indicated by the origin information that has been read in step S6001, using arrangement information of the $i^{th}$ first slice information. Herein, the phrase "radially from the position indicated by the origin information" refers to processing of extracting faces that are irradiated with X-rays from the $i^{th}$ first slice information, assuming that the irradiation source of the X-rays is located at the position indicated by the origin information, and the X-rays travel radially and perpendicularly to the $i^{th}$ first slice information.

(Step S6006) The magnification calculating portion 5807 acquires information for calculating a magnification that is an enlargement ratio or reduction ratio of the $i^{th}$ second slice information. This information indicates, for example, the distance from the X-ray source to a slice indicated by the $i^{th}$ second slice information ("P" described later), the distance from the X-ray source to a screen ("distance" described later), the length of one side of volume data (first slice information) ("psize" described later), and the length of one side of a slice in the space through which the X-rays pass ("X" described later).

(Step S6007) The magnification calculating portion 5807 calculates, for each of the multiple pieces of second slice information, a magnification that is an enlargement ratio or reduction ratio of the second slice information, using arrangement information of the second slice information (Step S6008) The third slice information group acquiring portion 5808 enlarges or reduces the second slice information according to the magnification that has been calculated in step S6008, thereby acquiring third slice information.

(Step S6009) The third slice information group acquiring portion 5808 temporarily stores the acquired third slice information on a memory.

(Step S6010) The second slice information group acquiring portion 5806 increments the counter i by 1. The procedure returns to step S6003.

(Step S6011) The synthesizing unit 58091 superimposes all third slice information that has been temporarily stored on a memory in step S6009, on a two-dimensional plane, thereby obtaining one image.

(Step S6012) The output unit 58092 outputs the images on the two-dimensional plane that have been superimposed in step S6011. The procedure returns to an upper-level function.

Hereinafter, a specific operation of the information processing apparatus in this embodiment will be described.

It is herein assumed that 3D voxel information, which is volume texture of a three-dimensional object that is a collection of CT data obtained by CT scanning the human chest, is stored in the object information storage portion 5802.

It is then assumed that the user has input an instruction to acquire a first slice information group. Then, the first slice information group acquiring portion 5805 extracts multiple pieces of first slice information perpendicular to a line of sight and sliced at constant intervals, from the 3D voxel information stored in the object information storage portion 5802, thereby acquiring a first slice information group. Then, the first slice information group acquiring portion 5805 accumulates the acquired first slice information group, in the first slice information group storage portion 5803.

Next, it is assumed that the user has input an instruction to output a DRR. Then, the receiving portion 5801 receives the instruction to output a DRR.

Next, the second slice information group acquiring portion 5806 reads origin information, from the origin information storage portion 5804. Then, the second slice information group acquiring portion 5806 and the like perform the following processing on all first slice information, sequentially from the first slice information at the first order.

That is to say, first, the processing as shown in FIG. 61 is performed. In FIG. 61, "X-ray source" represents the X-ray source, and its position is indicated by the origin information. Furthermore, "Slice" represents the first slice information, and "Screen" represents the last face that is irradiated with X-rays. As shown in FIG. 61, a region through which X-rays pass varies depending on the distance from the X-ray source (position indicated by the origin information). Accordingly, the second slice information group acquiring portion 5806 reads first slice information from the first slice information group storage portion 5803, and performs extraction from the first slice information, perpendicularly to the first slice information and radially, using the origin information. Then, the second slice information group acquiring portion 5806 obtains second slice information. The extracted second slice information is shown as 6101, 6102, and 6103 in FIG. 61. Herein, 6101, 6102, and 6103 are in the shape of faces that are irradiated with X-rays.

The second slice information 6101, 6102, and 6103 in FIG. 61 have mutually different sizes. Thus, the third slice information group acquiring portion 5808 enlarges or reduces the second slice information (images) having different sizes, thereby realizing perspective projection. It should be noted that second slice information (image) closer to the X-ray source has a larger enlargement ratio. Also, second slice information (image) remote from the X-ray source may be reduced.

Next, the magnification calculating portion 5807 calculates a magnification at which the second slice information (image) is enlarged or reduced, using Numerical Expressions 8 and 9 below. Herein, in Numerical Expressions 8 and 9, "P" represents the distance to each slice, "distance" represents the distance from the X-ray source to the screen, "screensize" represents the size of the screen, "psize" represents the length of one side of volume data (first slice information), and "X" represents the length of one side of a slice in the space through which X-rays pass.

$$X = \frac{P \times screensize}{distance}$$
Numerical Expression 8

$$M = \frac{psize}{X}$$
Numerical Expression 9

Next, a specific method for calculating the magnification performed by the magnification calculating portion 5807 will be described with reference to FIG. 62. First, a point at which the line-of-sight vector perpendicularly intersects a slice is taken as the origin, and the enlargement ratio is taken as M. Then, the magnification calculating portion 5807 reads stored information of Numerical Expressions 8 and 9, and reads stored "screensize", "distance", and "psize". Then, "P" is calculated from the arrangement information of the second slice information (image) and the origin information. Then, the magnification calculating portion 5807 substitutes the obtained "screensize", "distance", and "P" for Numerical Expression 8, thereby obtaining "X". Next, the magnification calculating portion 5807 substitutes "psize" and "X" for Numerical Expression 9, thereby obtaining the magnification "M".

Next, the third slice information group acquiring portion 5808 enlarges or reduces the second slice information according to the calculated magnification "M", thereby acquiring third slice information, and temporarily stores the third slice information on a memory.

This processing is performed on all first slice information. Then, the synthesizing unit 58091 superimposes all third slice information that has been temporarily stored on a memory, on a two-dimensional plane, thereby obtaining one image. Next, the output unit 58092 outputs the superimposed images on the two-dimensional plane. FIG. 63 shows an example of the images on the two-dimensional plane. FIG. 63 is a radiograph (DRR) of the chest. In FIG. 63, the DRR is formed by generating and superimposing images whose enlargement ratio varies depending on the distance between the X-ray source and each slice. The volume data based on which the display in FIG. 63 is obtained is patient's CT data having a voxel size of 256×256×256. FIG. 63 is obtained by setting parameters as appropriate and display the data.

Herein, it will be appreciated that systems of coordinates can be converted by an unshown unit as shown in FIG. 64 in a case where before generation of the DRR, the system of coordinates of the points that are contained in the first slice information is different from the system of coordinates of the points that are contained in the third slice information (system of coordinates of the DRR). FIG. 64 shows a state in which the coordinates (P, Q, R) of the system of coordinates of the points that are contained in the first slice information are converted into (P', Q', R') of the system of coordinates of the DRR. The coordinate conversion is a well known technique, and thus a detailed description thereof has been omitted.

As described above, according to this embodiment, it is possible to generate a DRR at high speed from CT data or the like.

Herein, in this embodiment, a DRR that has been output may be deformable. That is to say, a configuration with which the deformation processing as described in the foregoing embodiments may be added to the information processing apparatus in this embodiment. More specifically, in this configuration, as described in Embodiments 1, 3, and the like, mesh information of a three-dimensional object such as the chest corresponding to a three-dimensional object in the object information storage portion 5802 is held in a storage unit, and mesh information corresponding to a first slice information group, a second slice information group, and a third slice information group are managed, a receiving portion receives an instruction from the user, the mesh information is deformed, multiple pieces of third slice information are deformed according to the deformed mesh information, and a deformed DRR is output. Herein, in a case where a DRR corresponds to tetrahedron meshes, as shown in FIG. 65, if an upward force is applied to the DRR in FIG. 65A from lower left, then the DRR is deformed as shown in FIG. 65B. If a DRR is deformable, for example, it is possible to realize tracking irradiation of a moving object, by performing a simulation to estimate movement of a lung tumor due to breathing, in order to perform a treatment in which a lung tumor is irradiated with radiation while being tracked.

Furthermore, in this embodiment, it is preferable that the origin information indicating the position of the X-ray source is customizable according to an instruction from the user. Furthermore, it is preferable that the line-of-sight vector at the time of outputting a DRR is customizable. In this case, a receiving portion receives a line-of-sight vector specifying a line of sight, and a first slice information group acquiring portion extracts and acquires multiple pieces of first slice information perpendicular to the line of sight indicated by the line-of-sight vector and sliced at constant intervals, from 3D voxel information stored in an object information storage portion. Herein, in a case where first slice information is extracted, the intervals are typically constant, but are not necessarily have to be constant. The same is applied to other examples and other specific examples.

Software that implements the information processing apparatus in this embodiment may be a following program. Specifically, this program is a program for causing a computer to execute: a second slice information group acquiring step of performing extraction from each of at least two pieces of first slice information that are stored, perpendicularly to each of the multiple pieces of slice information and radially from the position indicated by origin information, using arrangement information of each of the multiple pieces of slice information, thereby acquiring multiple pieces of second slice information; a magnification calculating step of calculating, for each of the multiple pieces of second slice information, a magnification that is an enlargement ratio or reduction ratio of each second slice information, using arrangement information of the second slice information; a third slice information group acquiring step of enlarging or reducing each of the multiple pieces of second slice information according to the magnification that has been calculated in the magnification calculating step, thereby acquiring multiple pieces of third slice information; and an output step of outputting the multiple pieces of third slice information in a superimposed manner. Furthermore, in this program, it is preferable that the computer is caused to further execute a first slice information group acquiring step of extracting and acquiring multiple pieces of first slice information perpendicular to a line of sight and sliced at constant intervals, from 3D voxel information, which is volume texture of a three-dimensional object, and the at least two pieces of first slice information are the first slice information that has been acquired in the first slice information group acquiring step.

Furthermore, in this program, it is preferable that the computer is caused to further execute a receiving step of receiving a line-of-sight vector specifying the line of sight, and in the first slice information group acquiring step, multiple pieces of first slice information perpendicular to the line of sight indicated by the line-of-sight vector and sliced at constant intervals are extracted and acquired from the 3D voxel information.

Furthermore, in this program, it is preferable that the first slice information, the second slice information, and the third slice information have transparency information, which is information of the transparency of a point constituting each slice information, the computer is caused to further execute a receiving step of receiving the transparency information, and the transparency of the multiple pieces of third slice information that are output in a superimposed manner changes according to the transparency information that has been received in the receiving step.

FIG. 66 shows the external appearance of a computer for executing the program described in this specification, thereby implementing the information processing apparatus of the foregoing various embodiments. The foregoing embodiments can be implemented by computer hardware and a computer program executed thereon. FIG. 66 is an overall view of a computer system 340. FIG. 67 is a block diagram of the computer system 340.

In FIG. 66, the computer system 340 includes a computer 341 including a FD (flexible disk) drive and a CD-ROM (compact disk read only memory) drive, a keyboard 342, a mouse 343, and a monitor 344.

In FIG. 67, the computer 341 is connected, not only to a FD drive 3411 and a CD-ROM drive 3412, but also to a CPU (central processing unit) 3413, a bus 3414 to which the CPU 3413, the CD-ROM drive 3412, and the FD drive 3411 are connected, a ROM (read-only memory) 3415 in which a program such as a bootup program is to be stored, a RAM (random access memory) 3416 to which the CPU 3413 is connected, in which a command of an application program is temporarily stored, and with which a temporary storage area is to be provided, and a hard disk 3417 in which an application program, a system program, and data are to be stored. Herein, although not shown, the computer 341 may further include a network card for providing a connection to a LAN.

The program for causing the computer system 340 to execute the functions of the information processing apparatus in the foregoing embodiments may be stored in a CD-ROM 3501 or a FD 3502, inserted into the CD-ROM drive 3412 or the FD drive 3411, and transmitted to the hard disk 3417. Alternatively, the program may be transmitted to the computer 341 via an unshown network, and stored in the hard disk 3417. At the time of execution, the program is loaded into the RAM 3416. The program may be loaded from the CD-ROM 3501 or the FD 3502, or directly from a network.

The program does not necessarily have to include, for example, an operating system (OS) or a third party program for causing the computer 341 to execute the functions of the information processing apparatus in the foregoing embodiments. The program may be any program as long as it includes a command portion to call an appropriate function (module) in a controlled manner and obtain desired results. The manner in which the computer system 340 operations is known, and thus a detailed description thereof has been omitted.

It should be noted that in the program, processing that is performed by hardware, for example, processing performed by a display device or the like in the output portion (processing that can only be performed with hardware) is not included.

Furthermore, in the foregoing embodiments, it will be appreciated that two or more storage units in one apparatus may be physically implemented as one medium.

Furthermore, in the foregoing embodiments, each processing (each function) may be implemented by integrated processing by a single apparatus (system), or may be implemented by distributed processing by multiple apparatuses.

Furthermore, the computer that executes this program may be a single computer, or may be multiple computers. More specifically, centralized processing may be performed, or distributed processing may be performed.

The present invention is not limited to the embodiments set forth herein. Various modifications are possible within the scope of the present invention.

INDUSTRIAL APPLICABILITY

As described above, the information processing system according to the present invention has the effect that information relating to the elasticity of a three-dimensional object can be handled, and thus this system is useful, for example, as a simulator apparatus for surgeries.

BRIEF DESCRIPTION OF THE DRAWINGS

Figure 6:
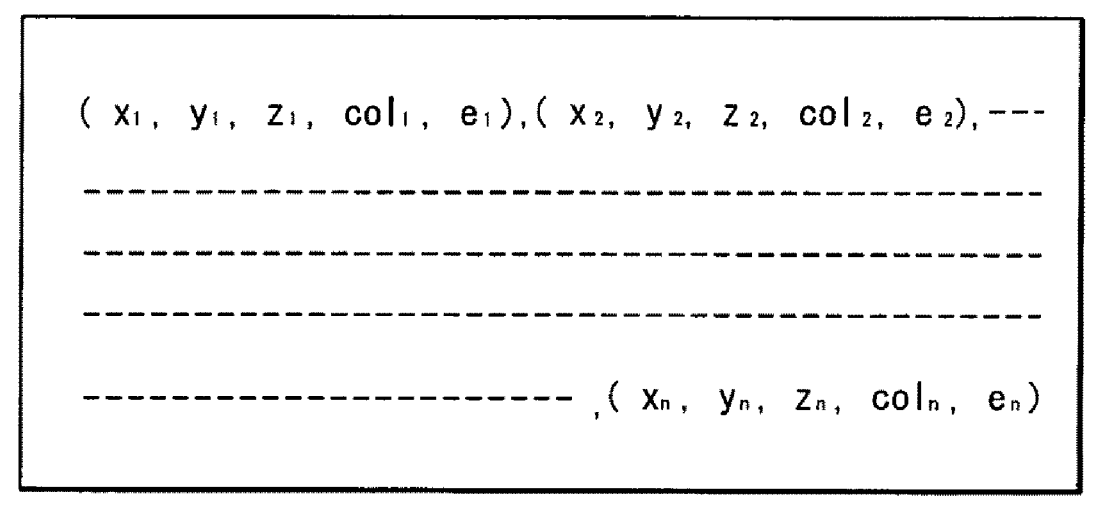

FIG. 6 shows 3D voxel information in the information processing apparatus.

FIG. 7 shows first mesh information in the information processing apparatus.

FIG. 10 shows second mesh information in the information processing apparatus.

FIG. 24 illustrates a surgical instrument metaphor in the information processing apparatus.

FIG. 39 shows an example of the data structure of second mesh information in the information processing apparatus.

Figure 40:
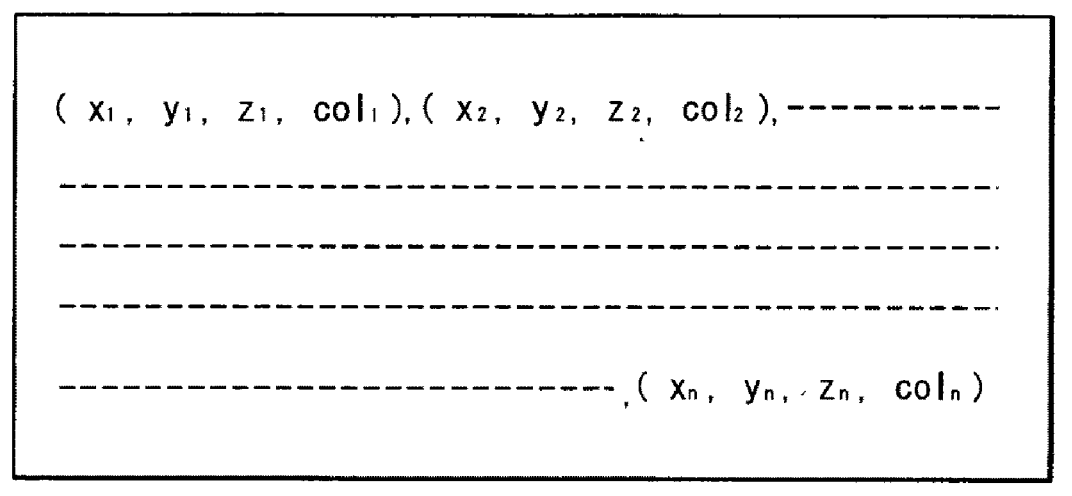

FIG. 40 shows an example of the data structure of 3D voxel information in the information processing apparatus.

Figure 1:
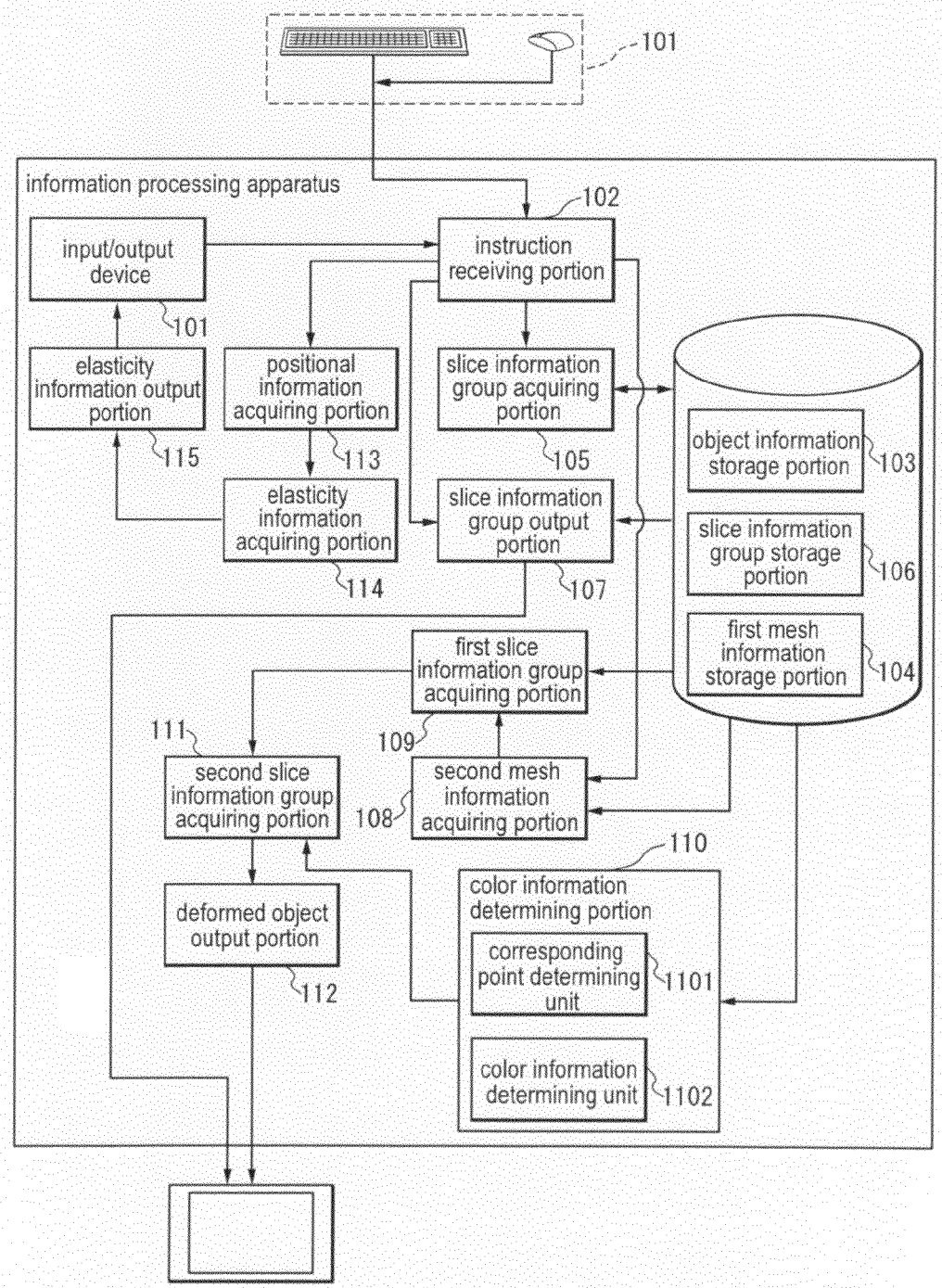
FIG. 1 is a block diagram of an information processing apparatus in Embodiment 1.
Figure 2:
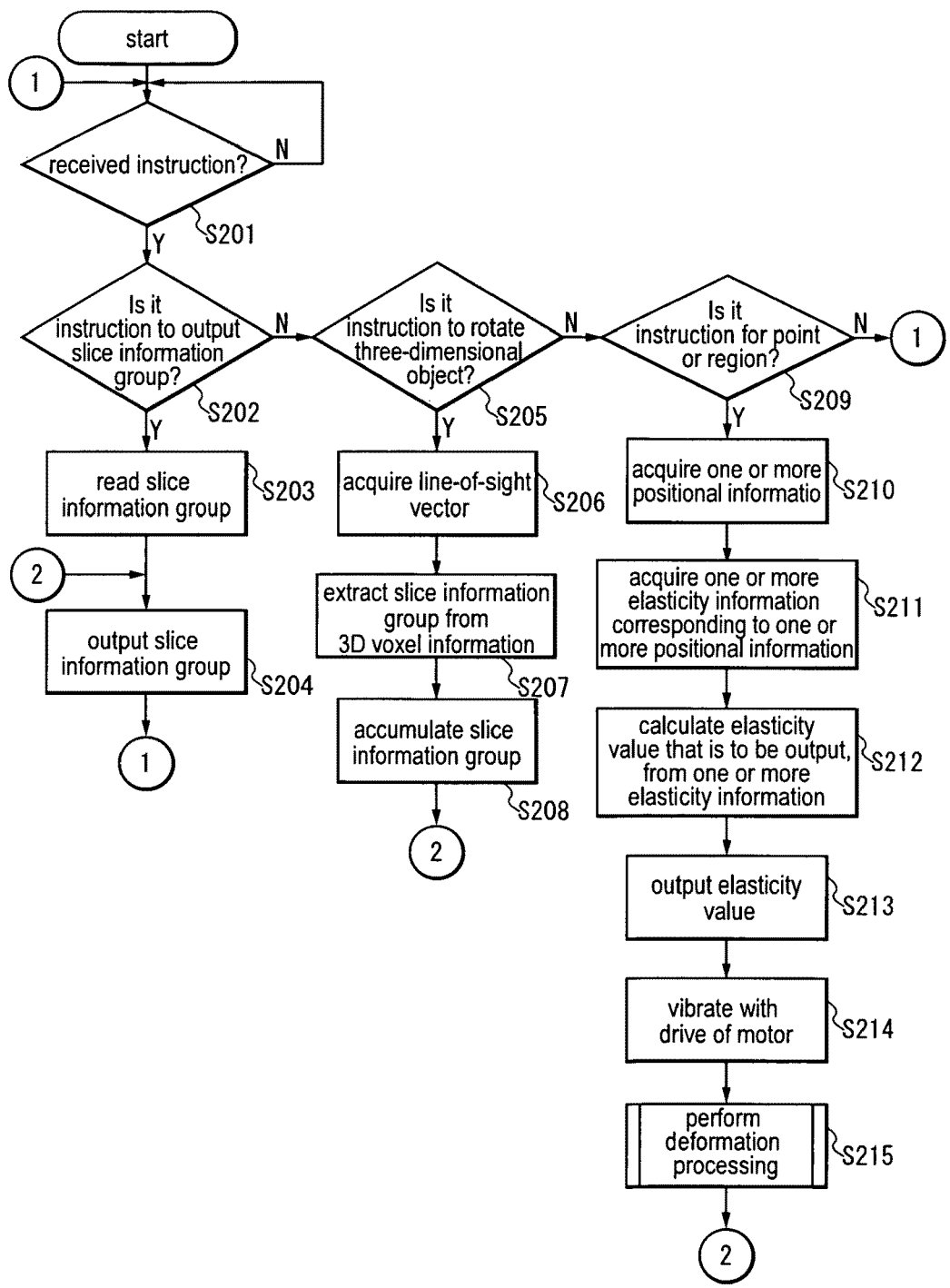
FIG. 2 is a flowchart illustrating the operation of the information processing apparatus.
Figure 3:
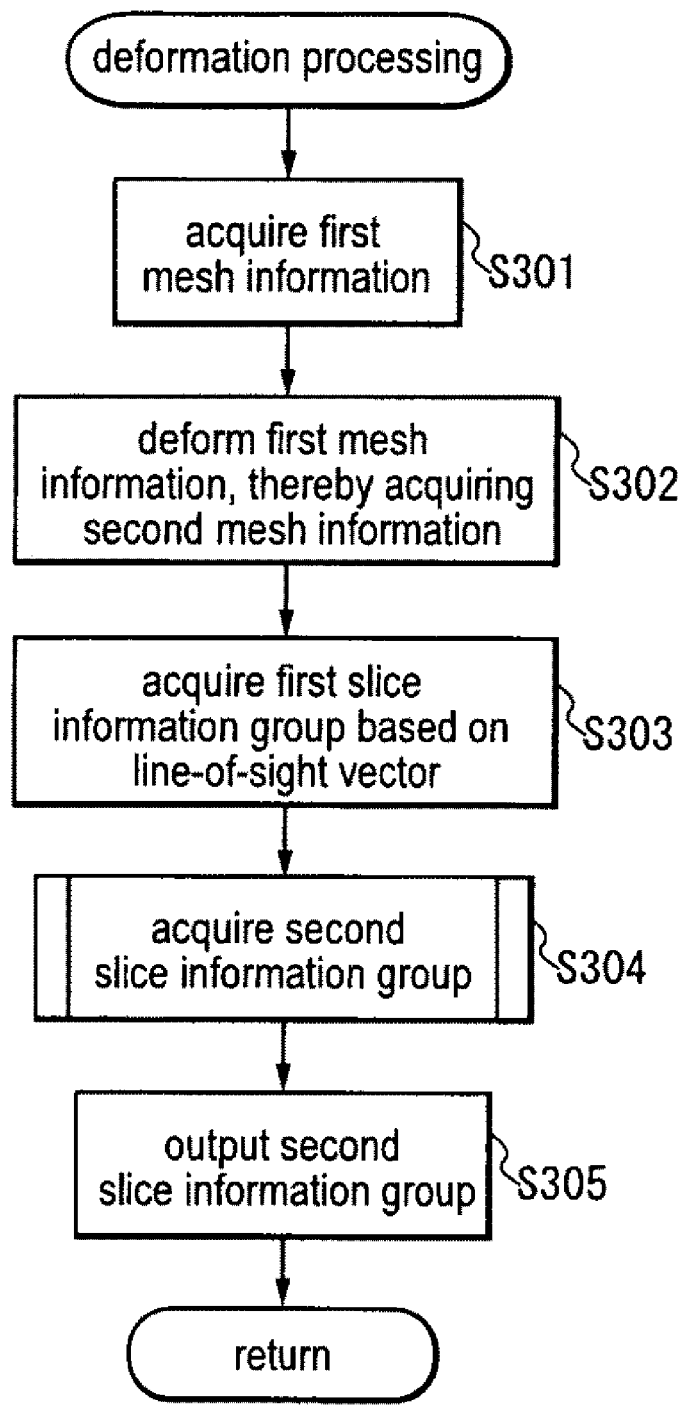
FIG. 3 is a flowchart illustrating deformation processing in the information processing apparatus.
Figure 4:
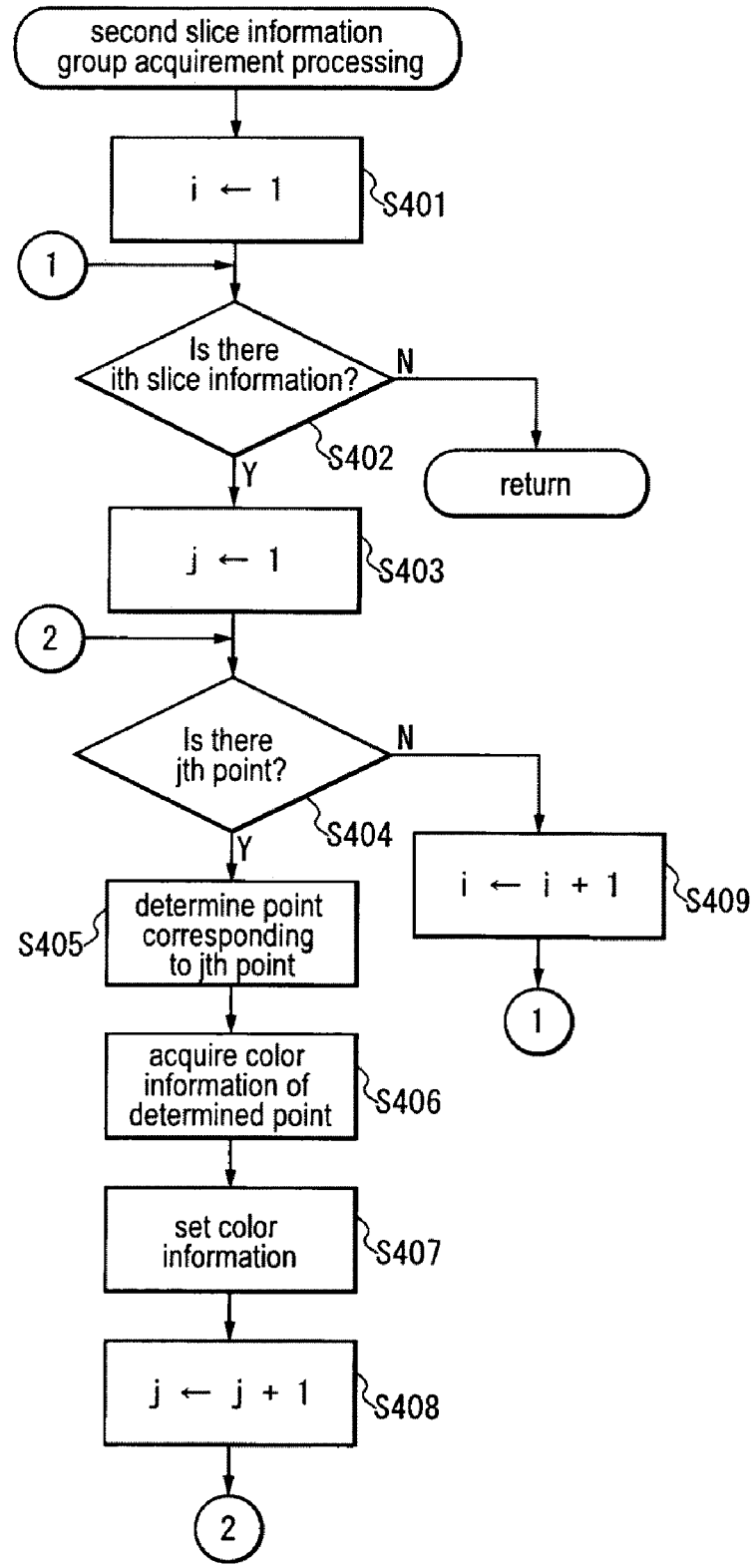
FIG. 4 is a flowchart illustrating second slice information group acquiring processing in the information processing apparatus.
Figure 5A:
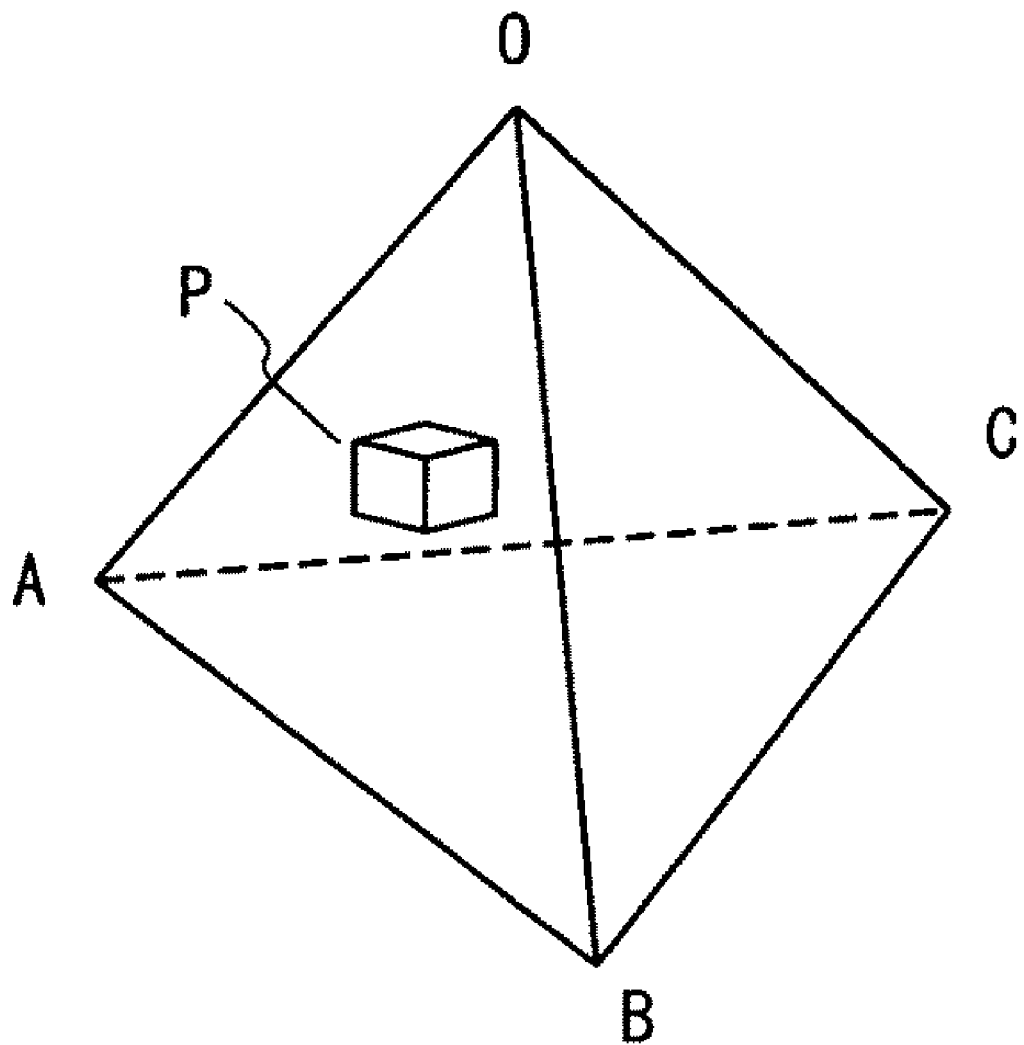
FIG. 5 shows a tetrahedron constituting a three-dimensional object that is to be deformed in the information processing apparatus.
Figure 5B:
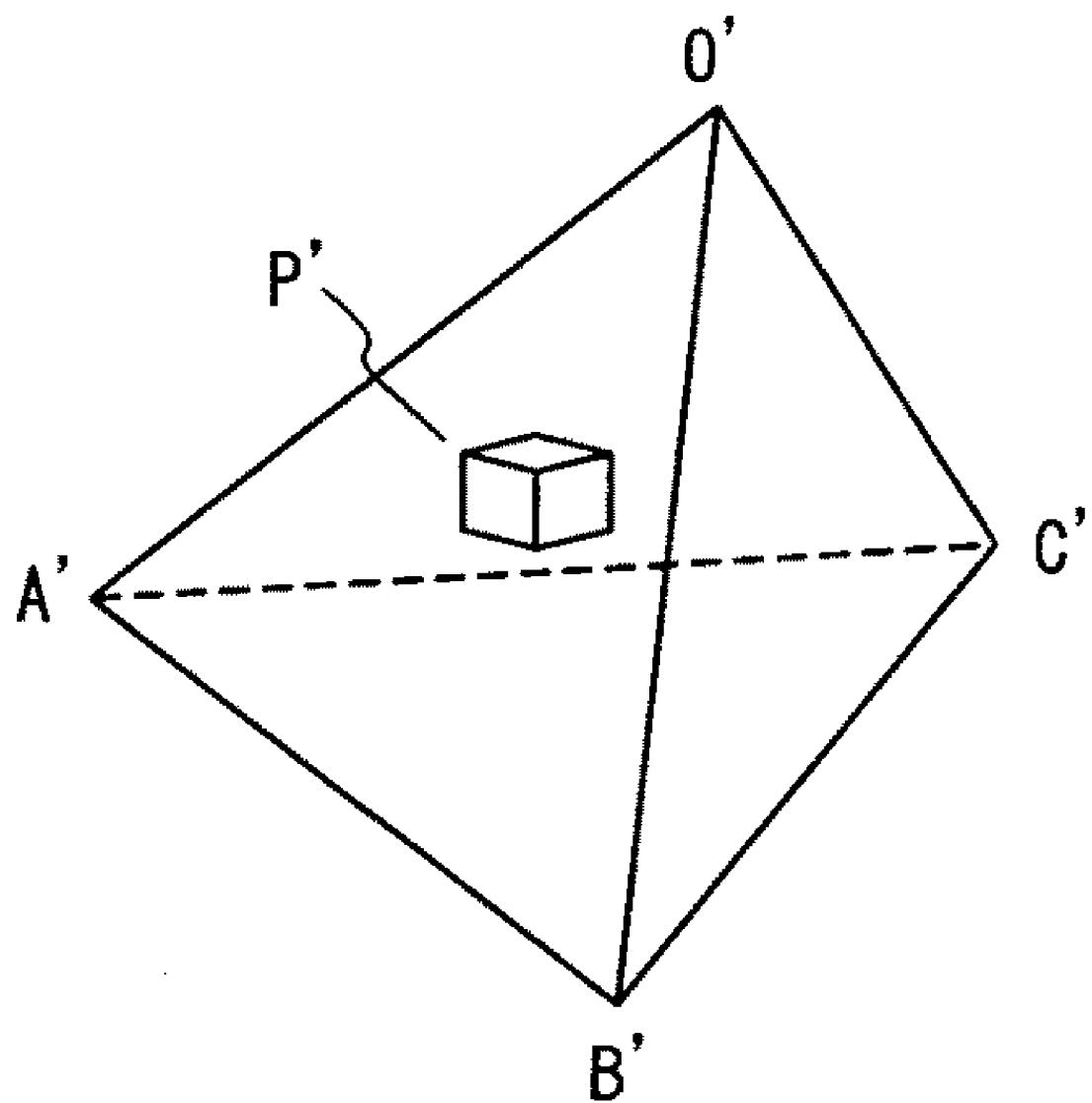
Figure 8:
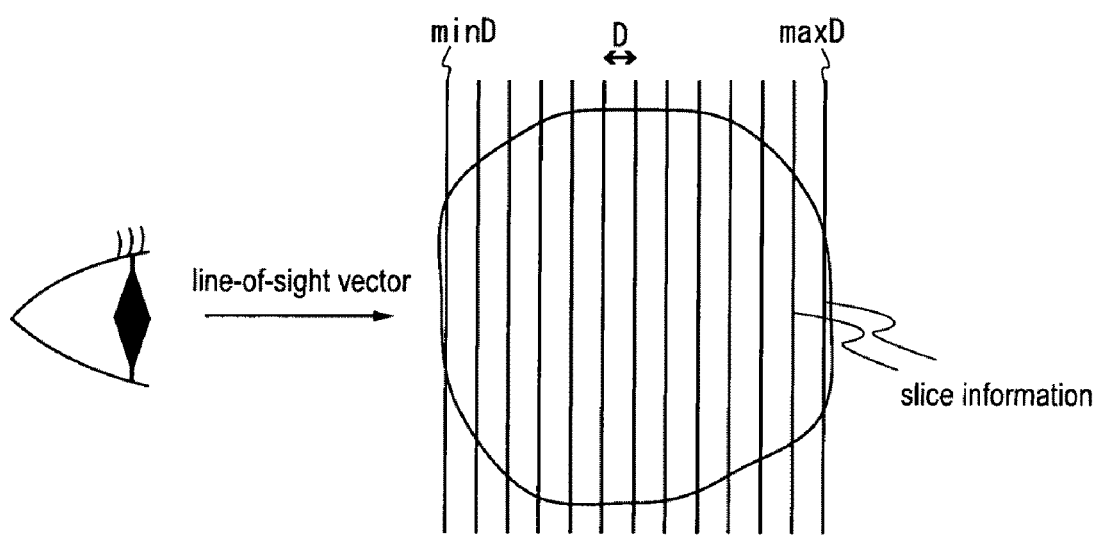
FIG. 8 shows an image at the time of acquiring a first slice information group in the information processing apparatus.
Figure 9:
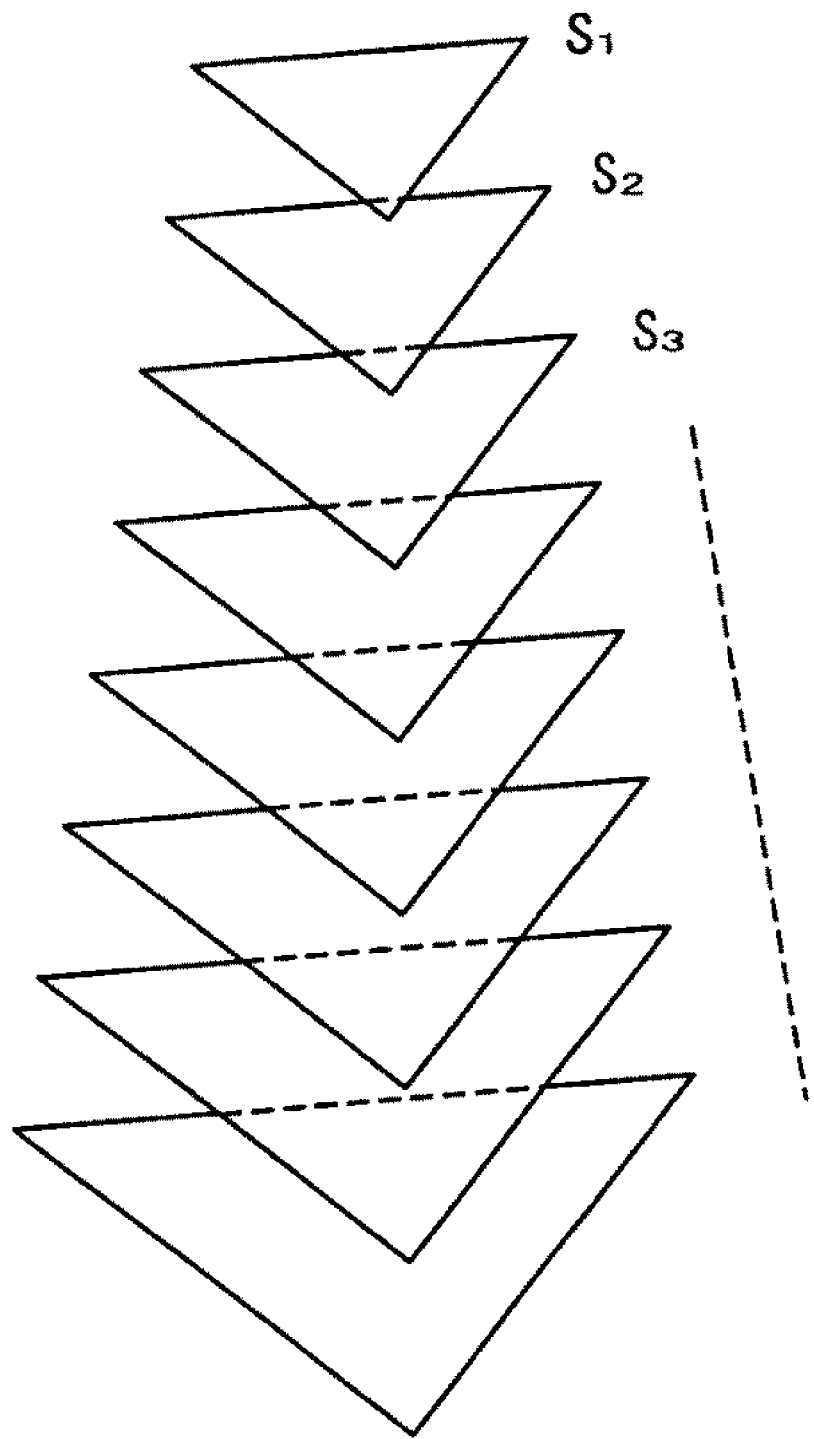
FIG. 9 shows a slice information group in the information processing apparatus.
Figure 11:
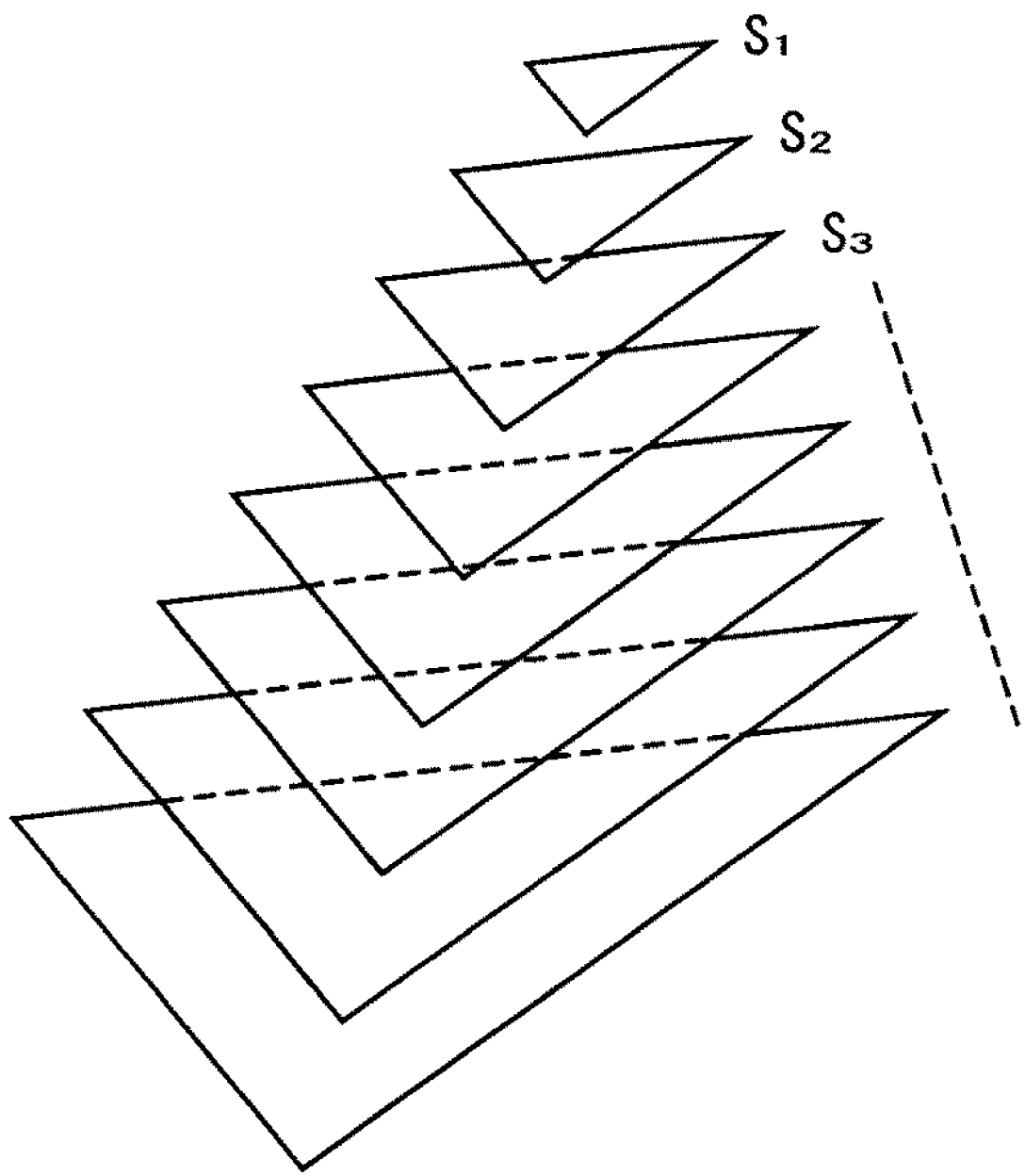
FIG. 11 shows a slice information group after deformation in the information processing apparatus.
Figure 12A:
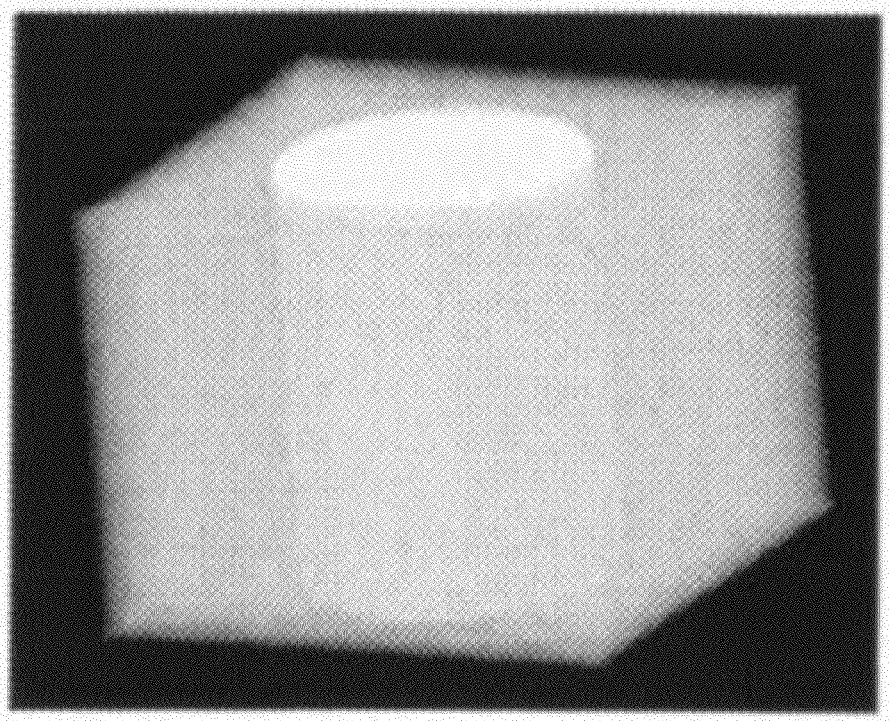
FIG. 12 shows a three-dimensional object that is to be deformed in the information processing apparatus.
Figure 12B:
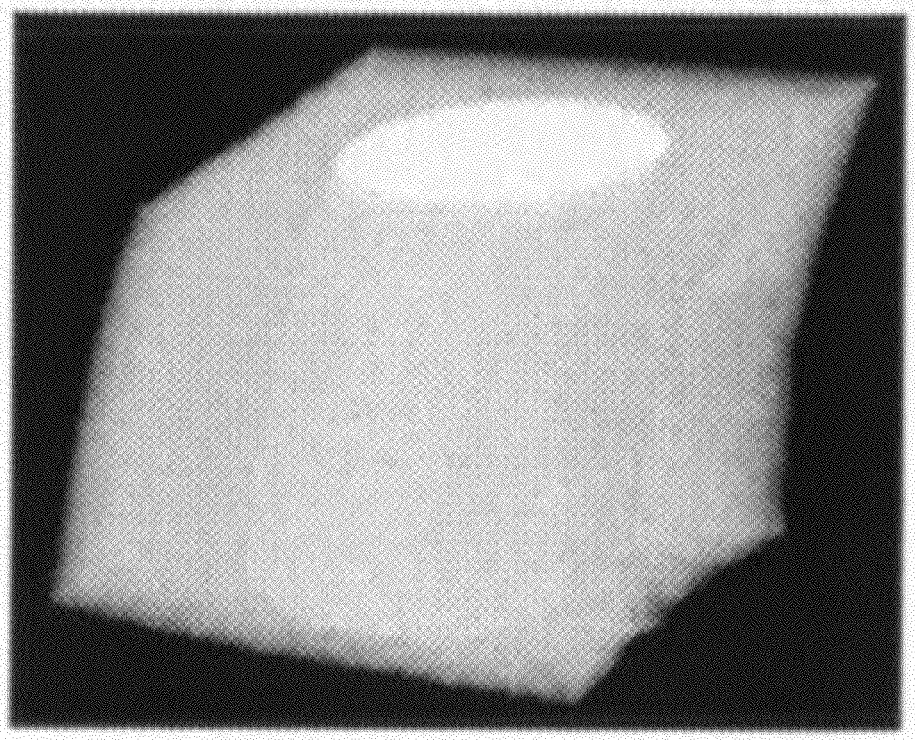
Figure 12C:
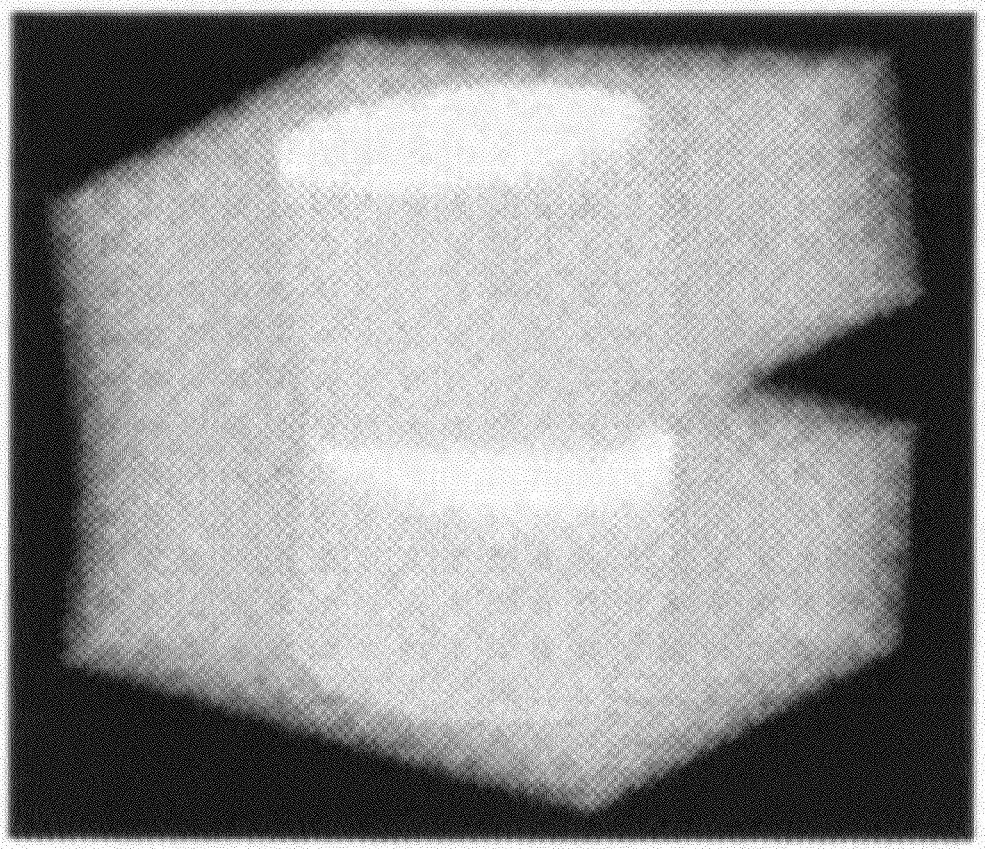
Figure 13:
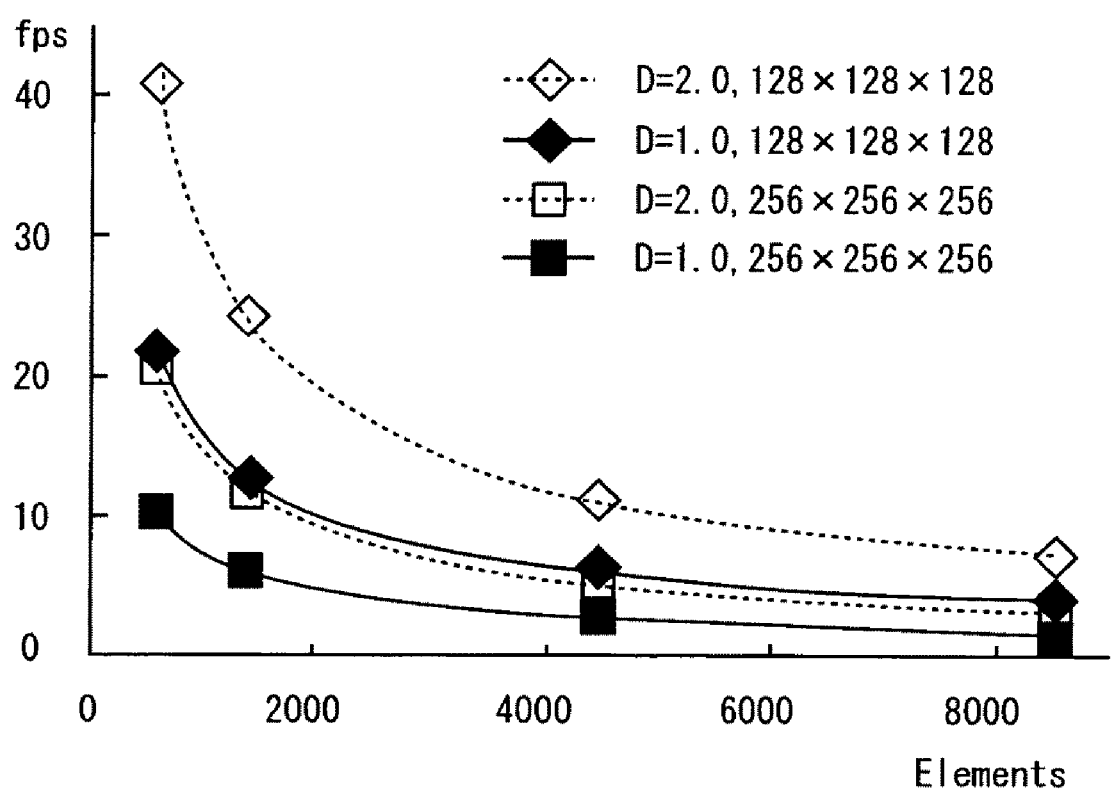
FIG. 13 shows data for examining the calculation time in the information processing apparatus.
Figure 14A:
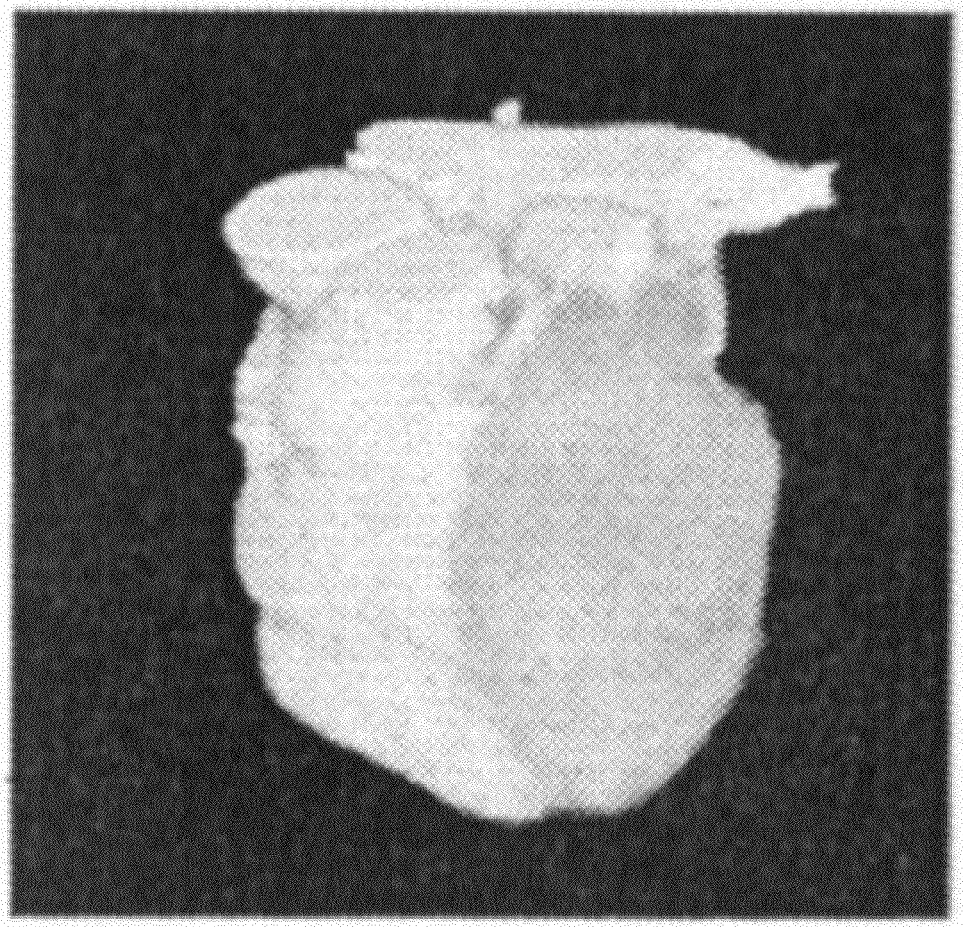
FIG. 14 shows the myocardium that is to be deformed in the information processing apparatus.
Figure 14B:
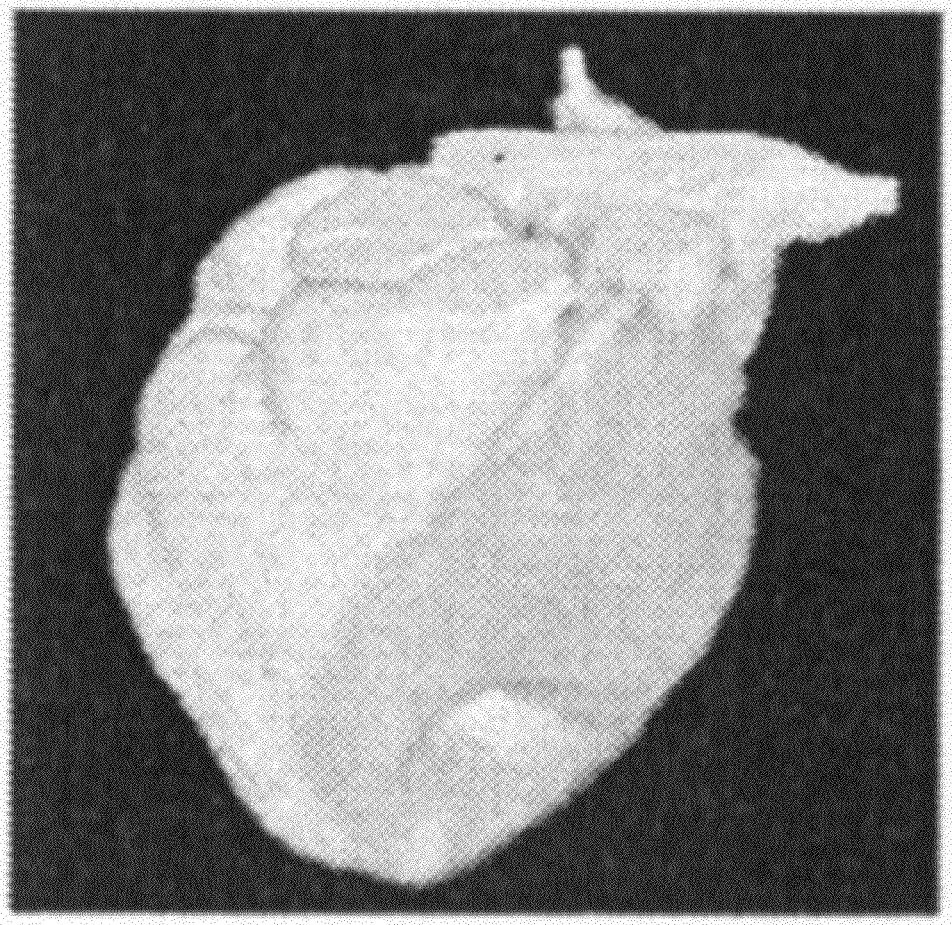
Figure 15A:
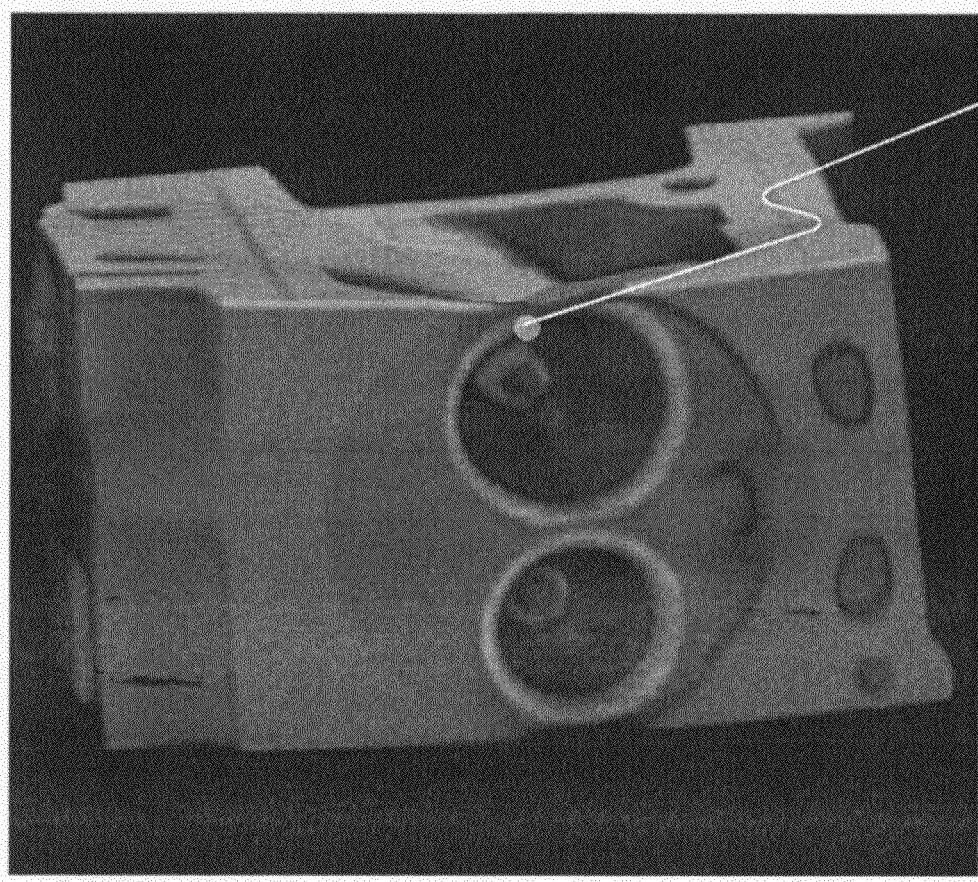
FIG. 15 shows a three-dimensional object that is to be deformed in the information processing apparatus.
Figure 15B:
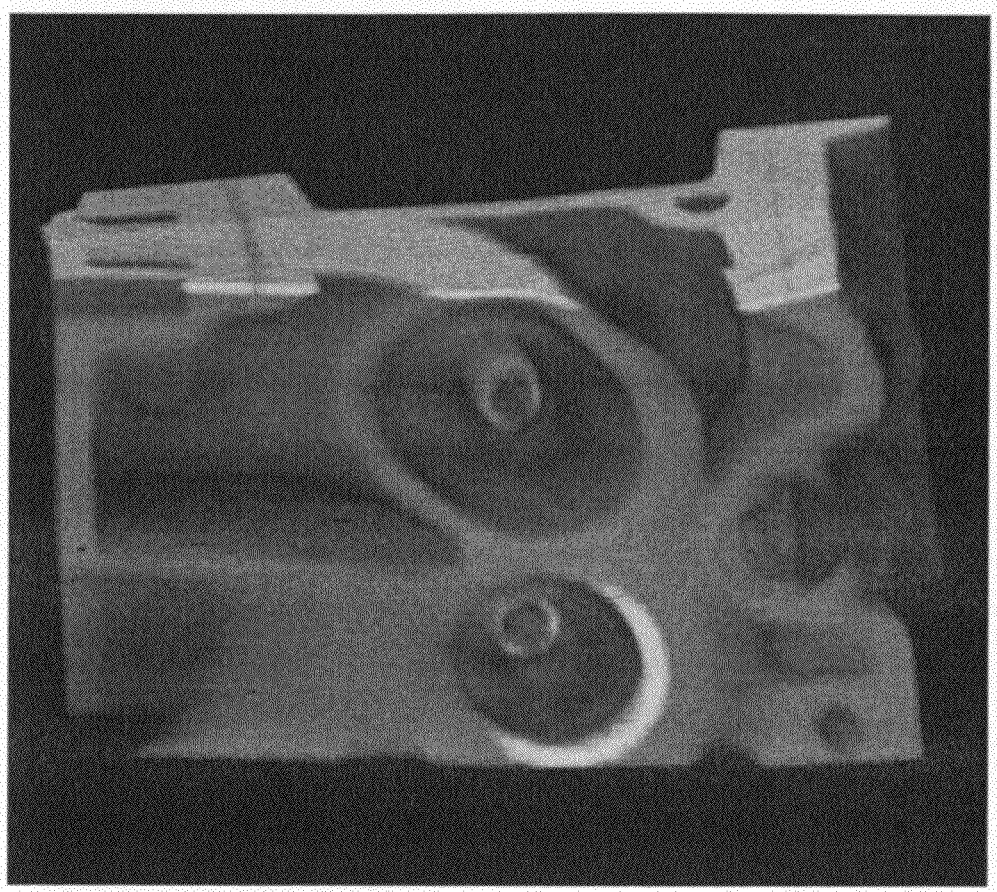
Figure 16:
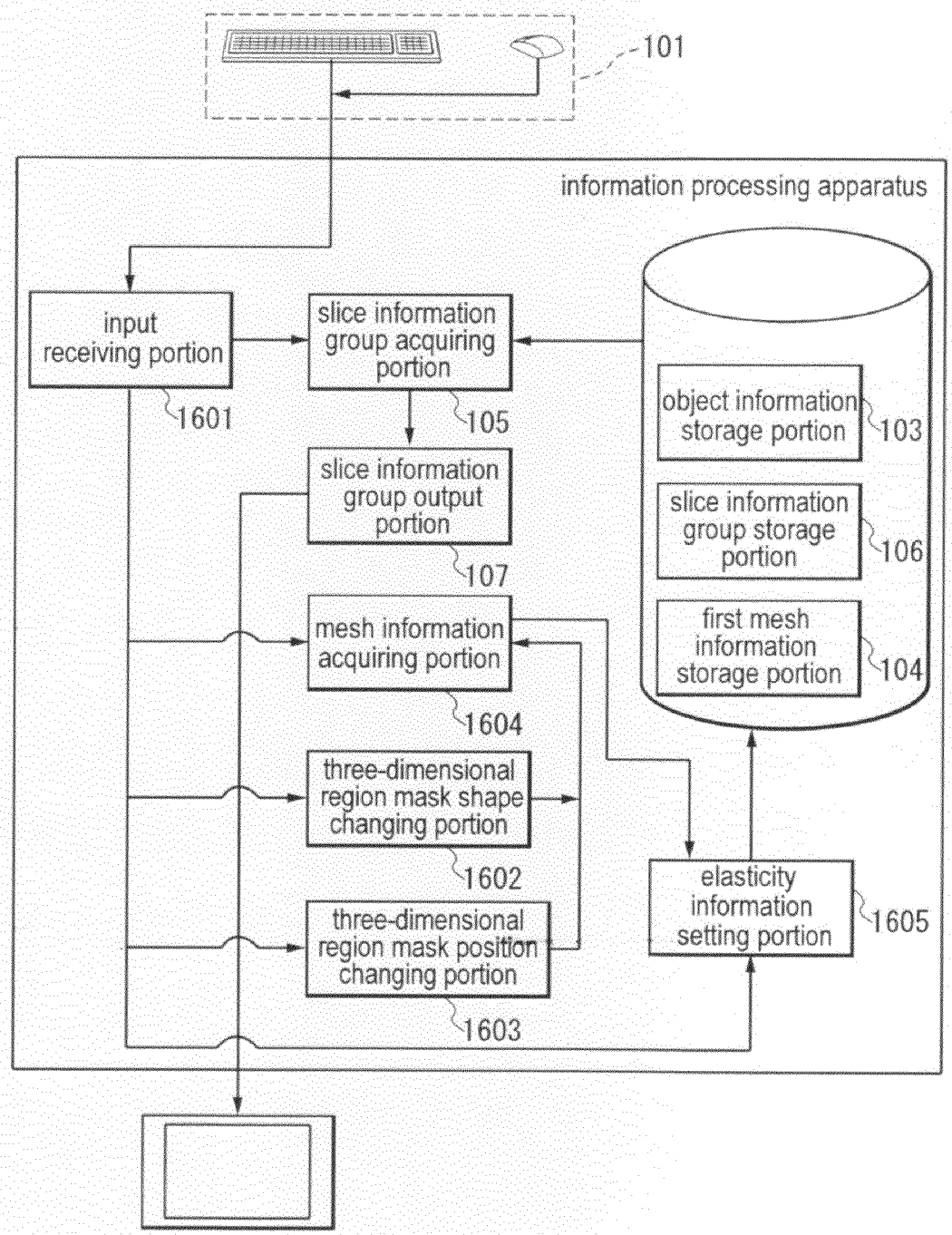
FIG. 16 is a block diagram of an information processing apparatus in Embodiment 2.
Figure 17:
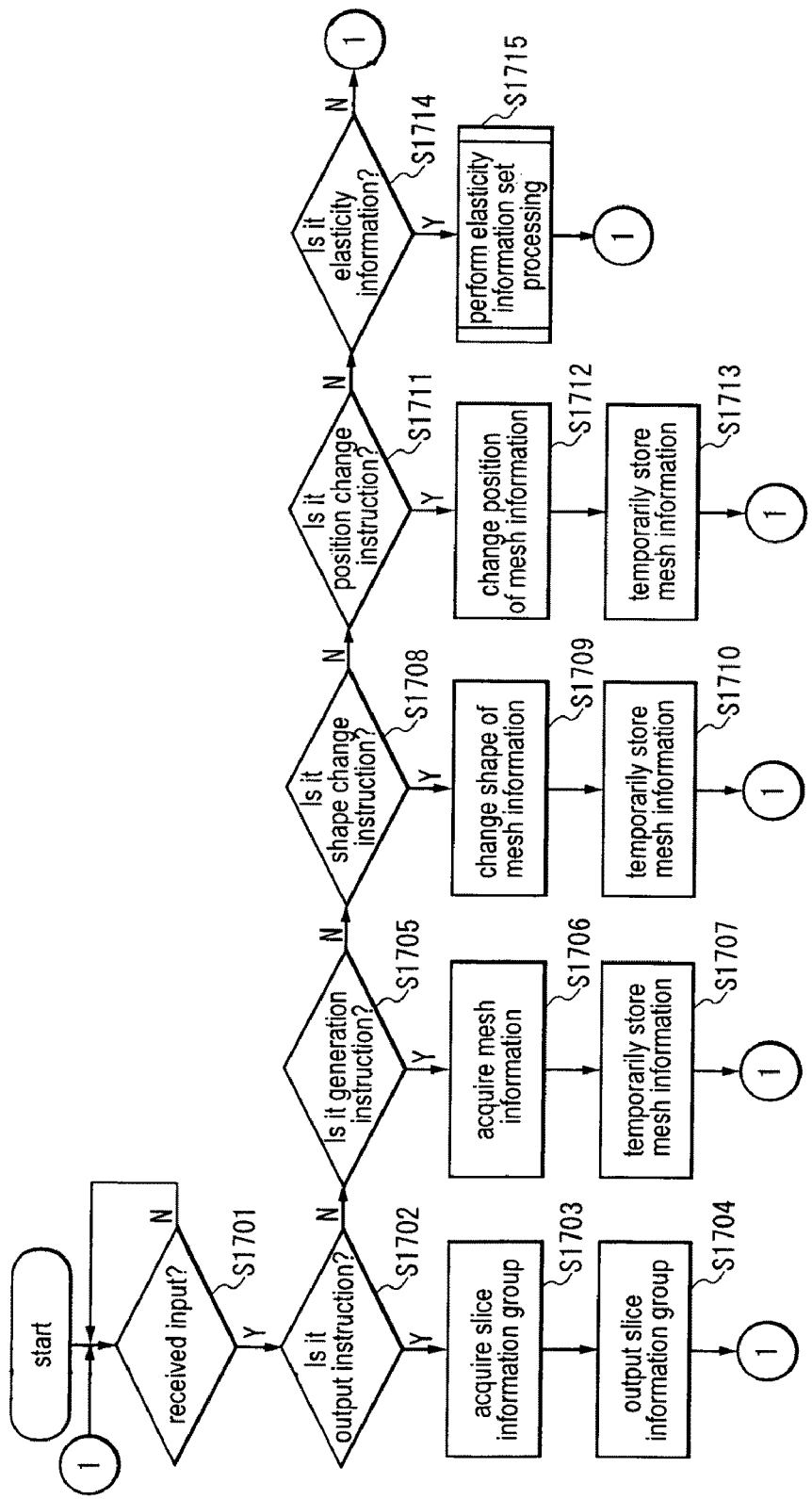
FIG. 17 is a flowchart illustrating the operation of the information processing apparatus.
Figure 18:
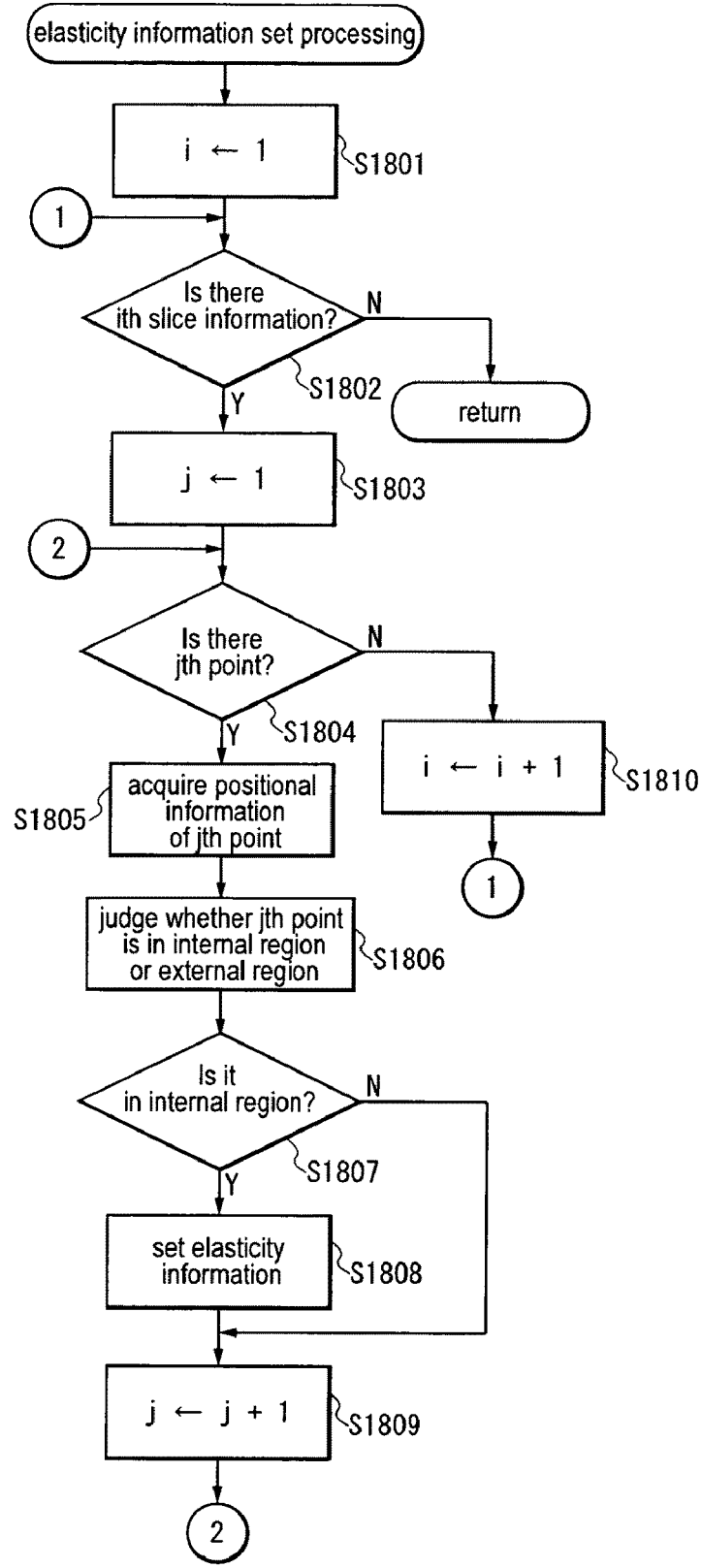
FIG. 18 is a flowchart illustrating the operation of elasticity information set processing in the information processing apparatus.
Figure 19:
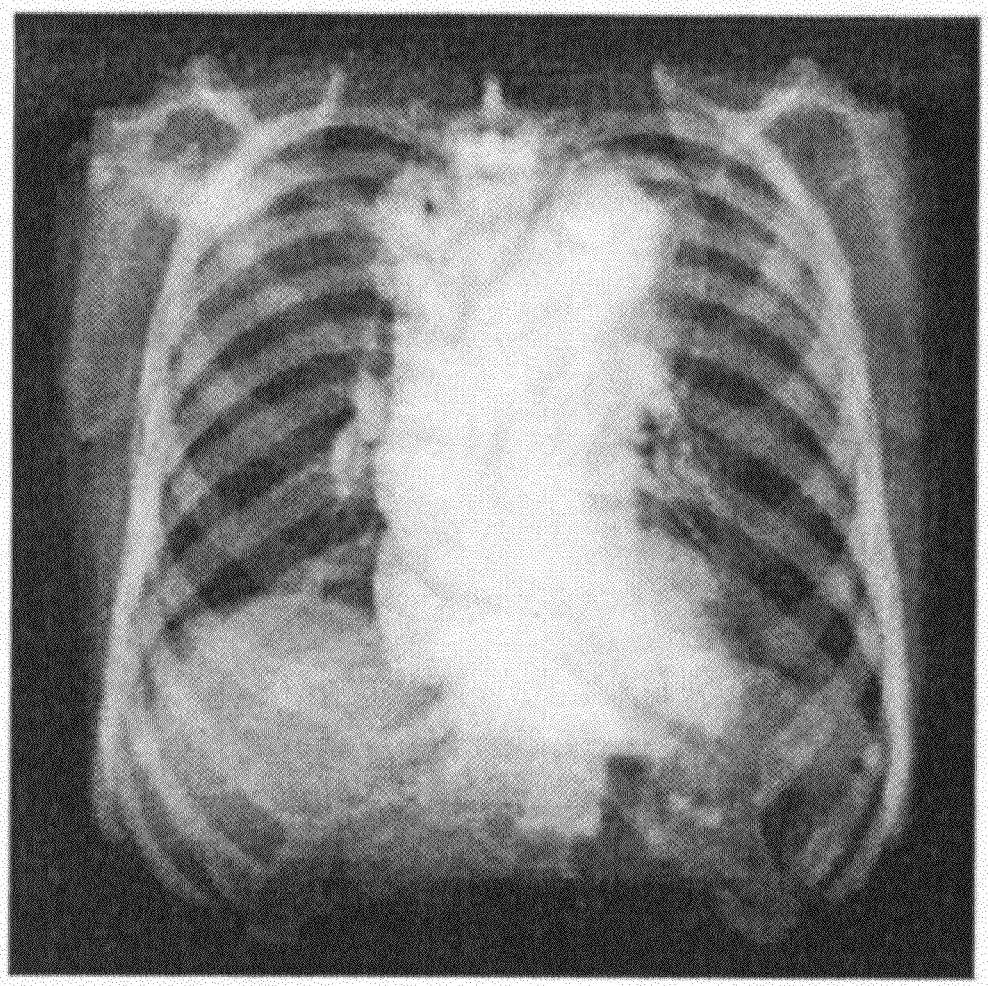
FIG. 19 shows a display example of a slice information group in the information processing apparatus.
Figure 20:
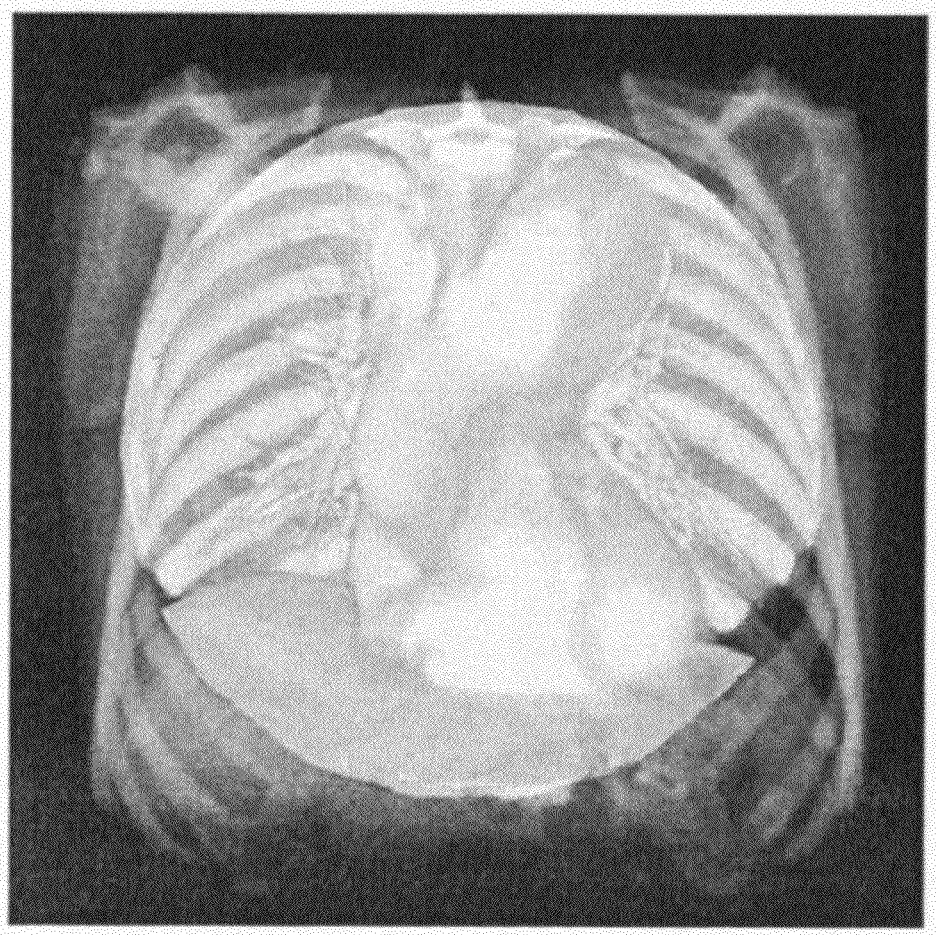
FIG. 20 shows a view displaying three-dimensional mesh information with respect to the displayed slice information group.
Figure 21:
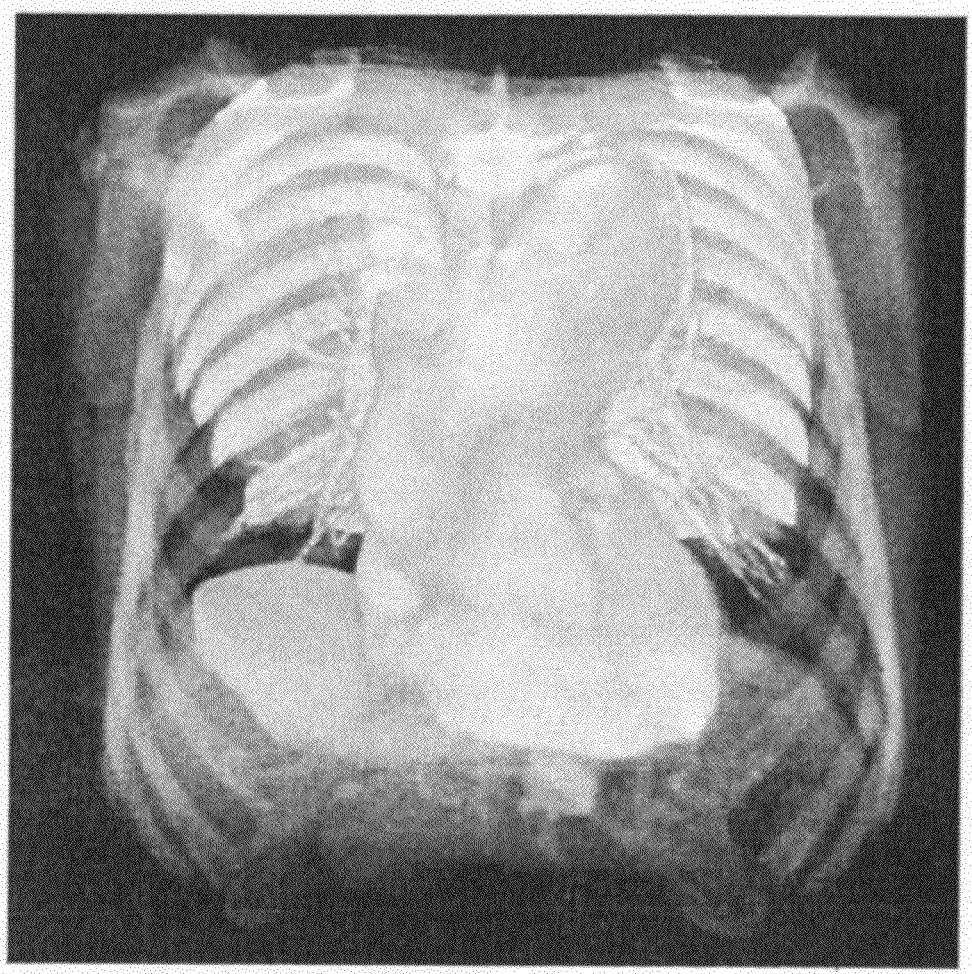
FIG. 21 shows a view displaying mesh information after deformation in the information processing apparatus.
Figure 22:
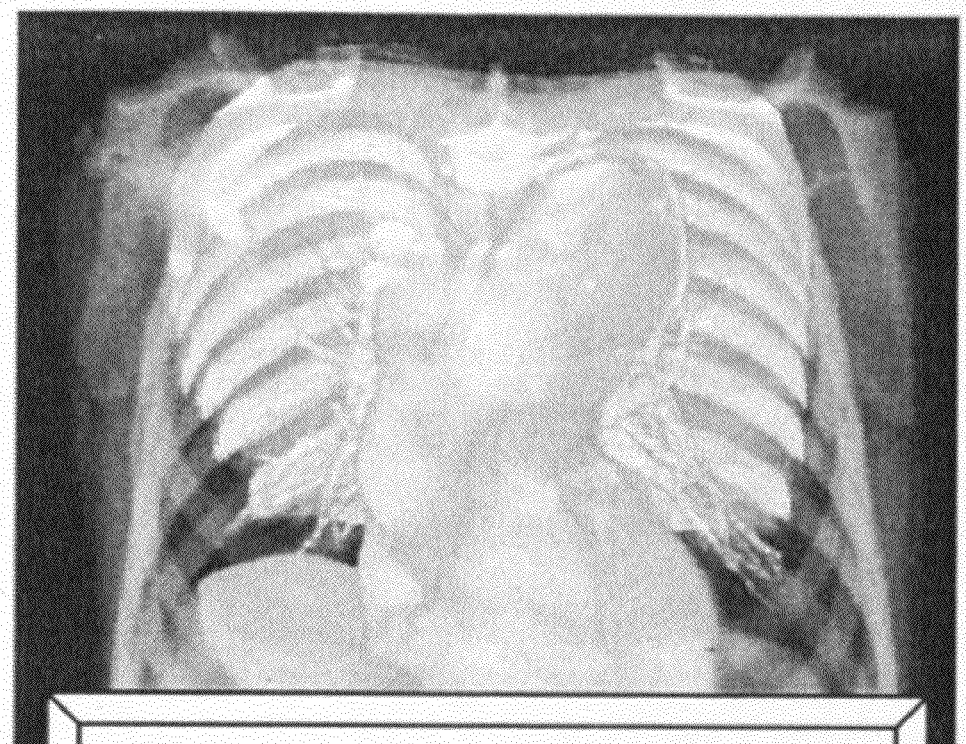
FIG. 22 shows an example of an input menu for the elasticity information.
Figure 23:
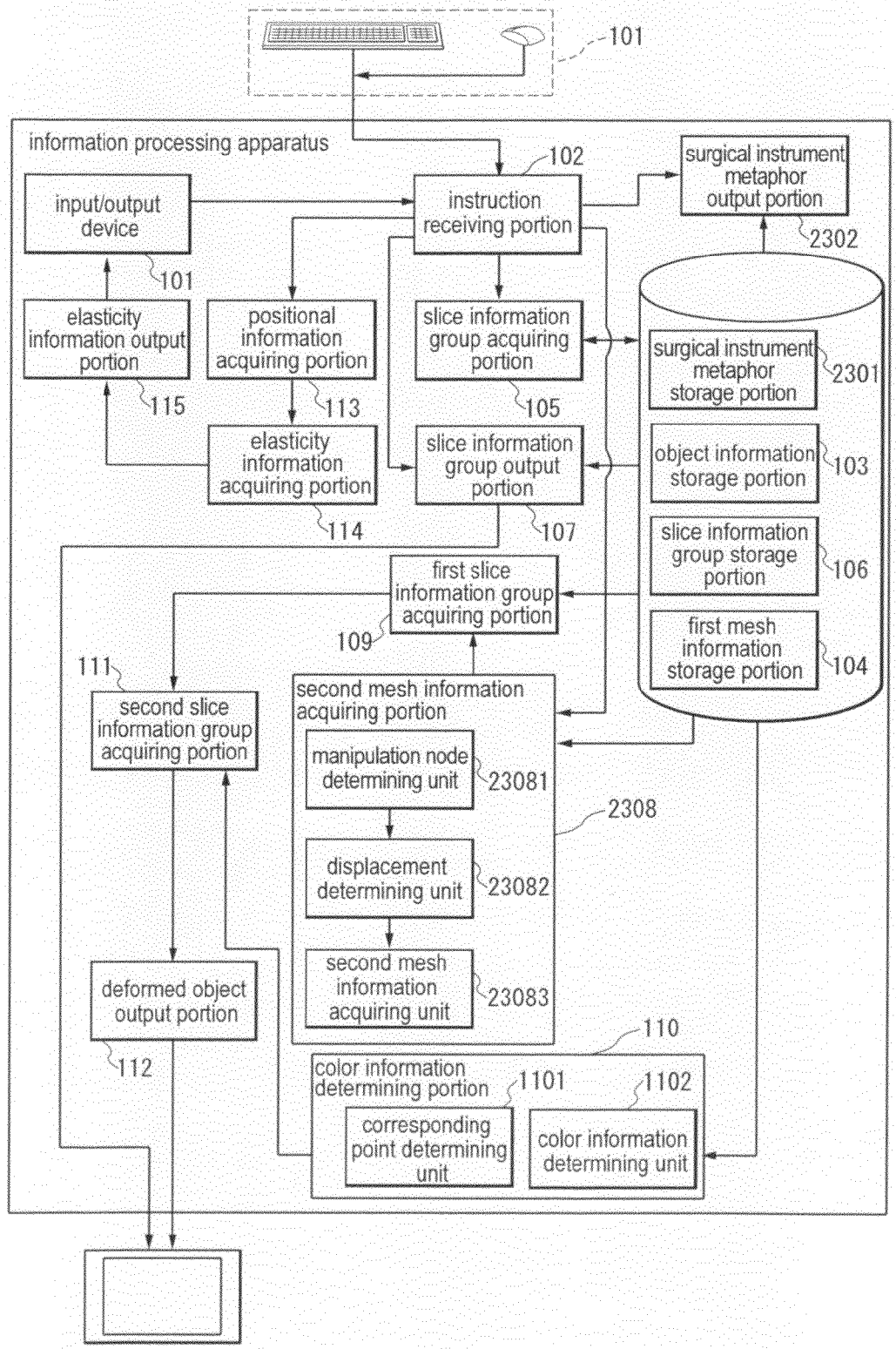
FIG. 23 is a block diagram of an information processing apparatus in Embodiment 3.
Figure 25:
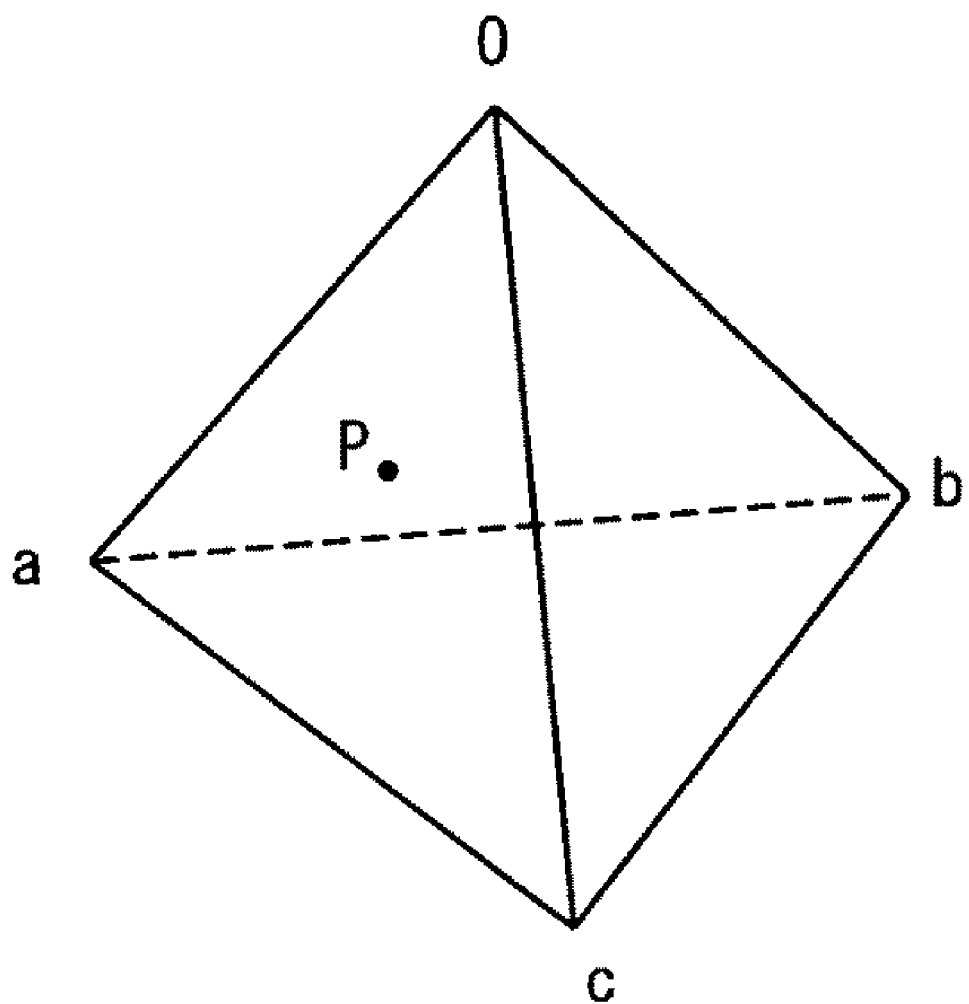
FIG. 25 illustrates a tetrahedron mesh of the surgical instrument metaphor.
Figure 26:
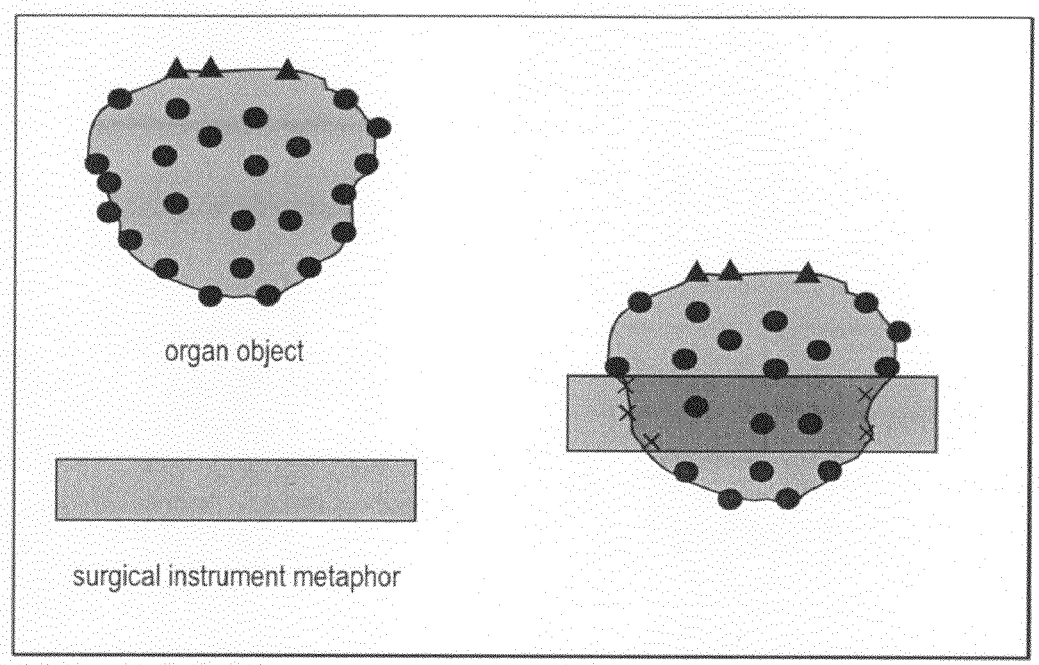
FIG. 26 shows a concept of the processing of a manipulation node determining unit in the information processing apparatus.
Figure 27:
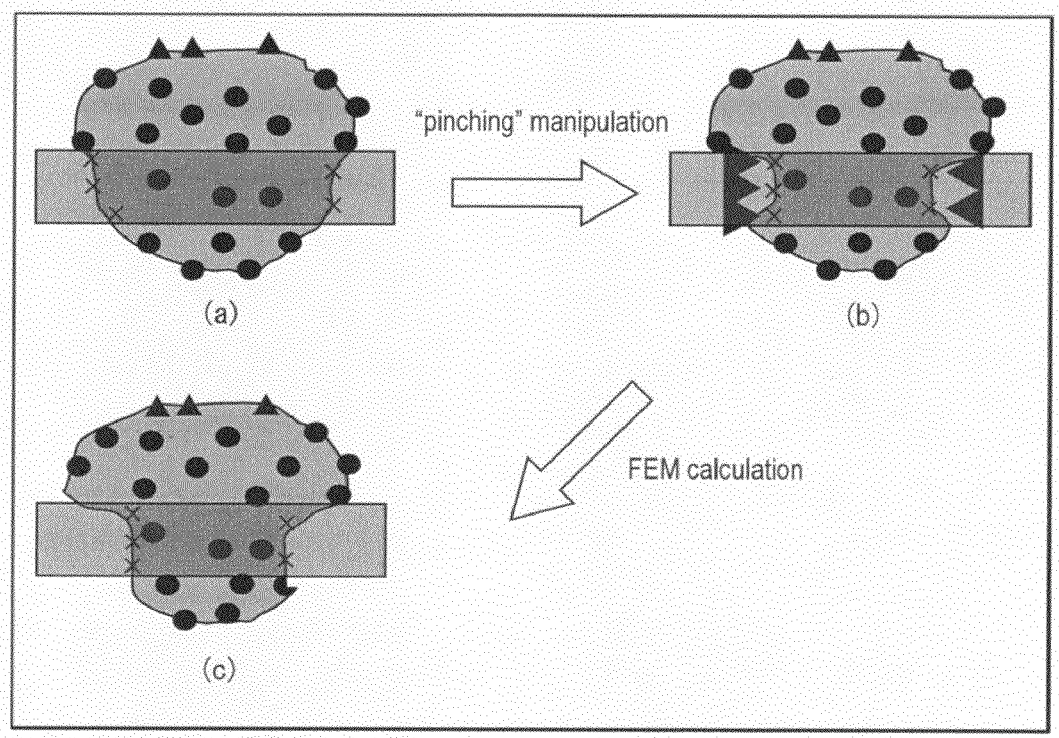
FIG. 27 shows a concept of displacement of manipulation nodes in the information processing apparatus.
Figure 28:
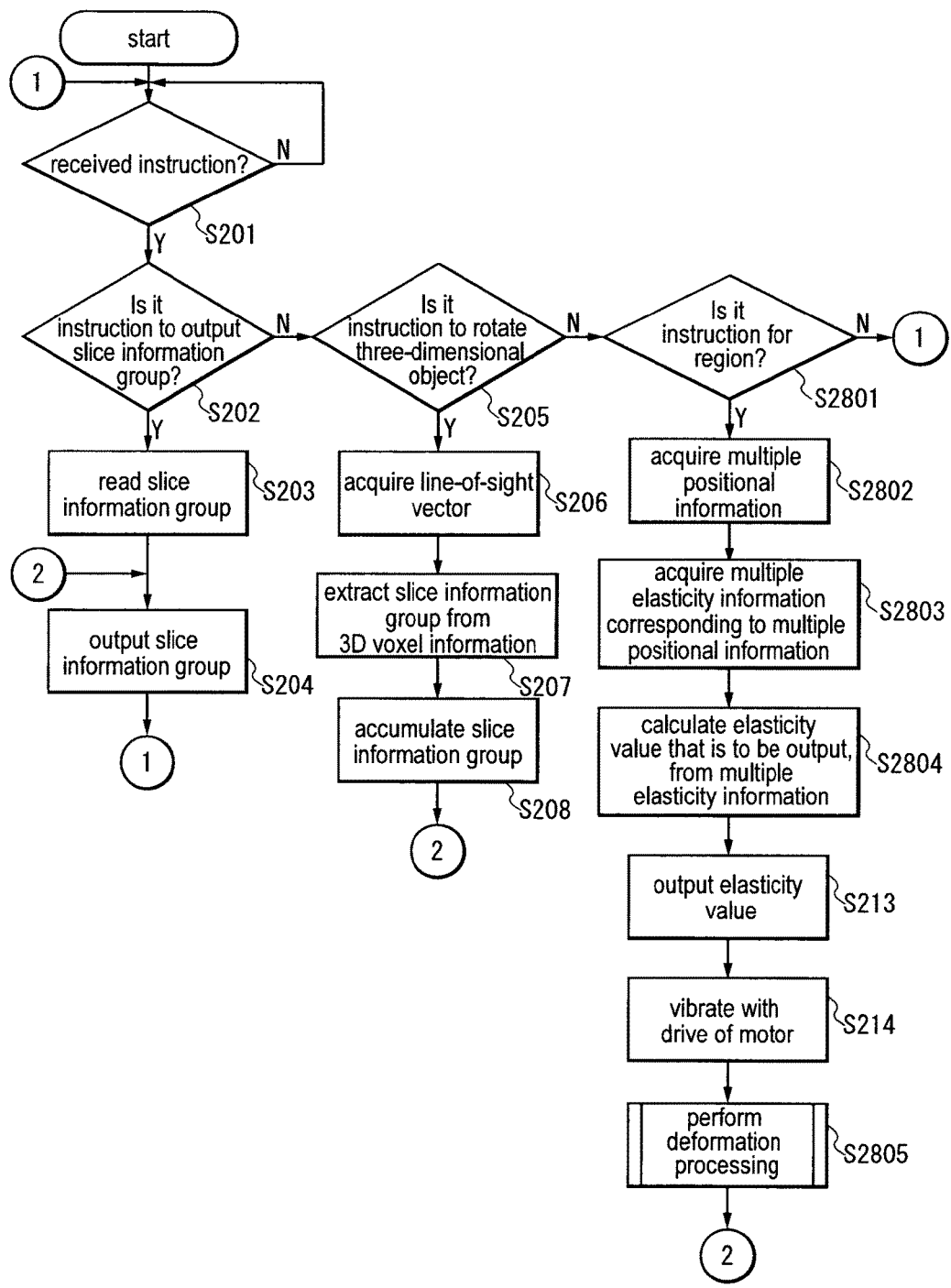
FIG. 28 is a flowchart illustrating the operation of the information processing apparatus.
Figure 29:
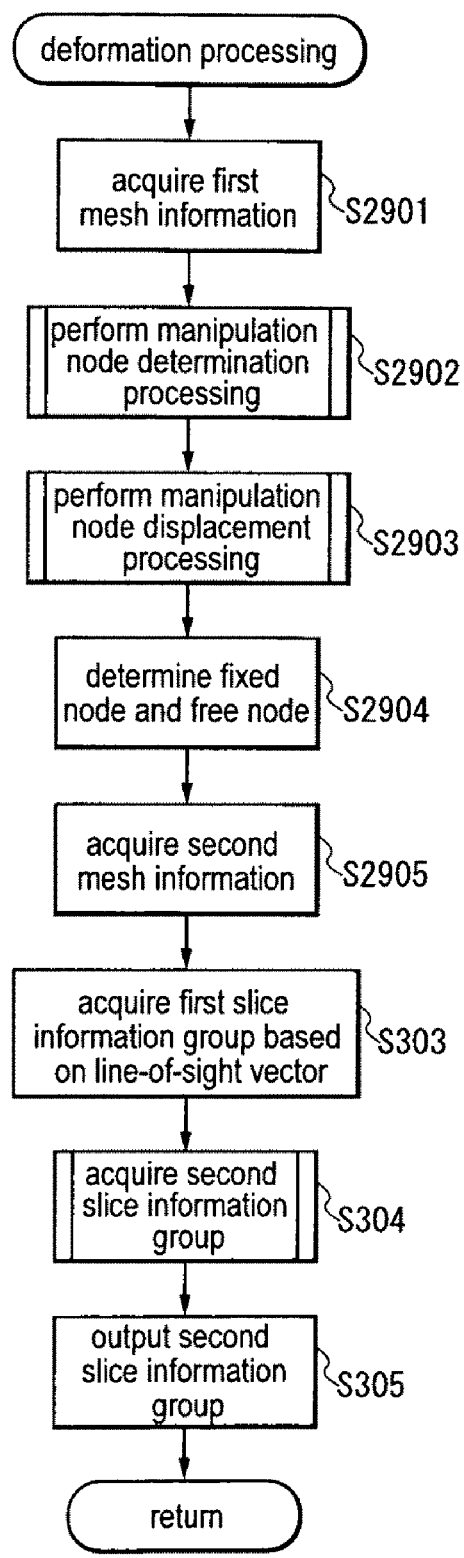
FIG. 29 is a flowchart illustrating deformation processing in the information processing apparatus.
Figure 30:
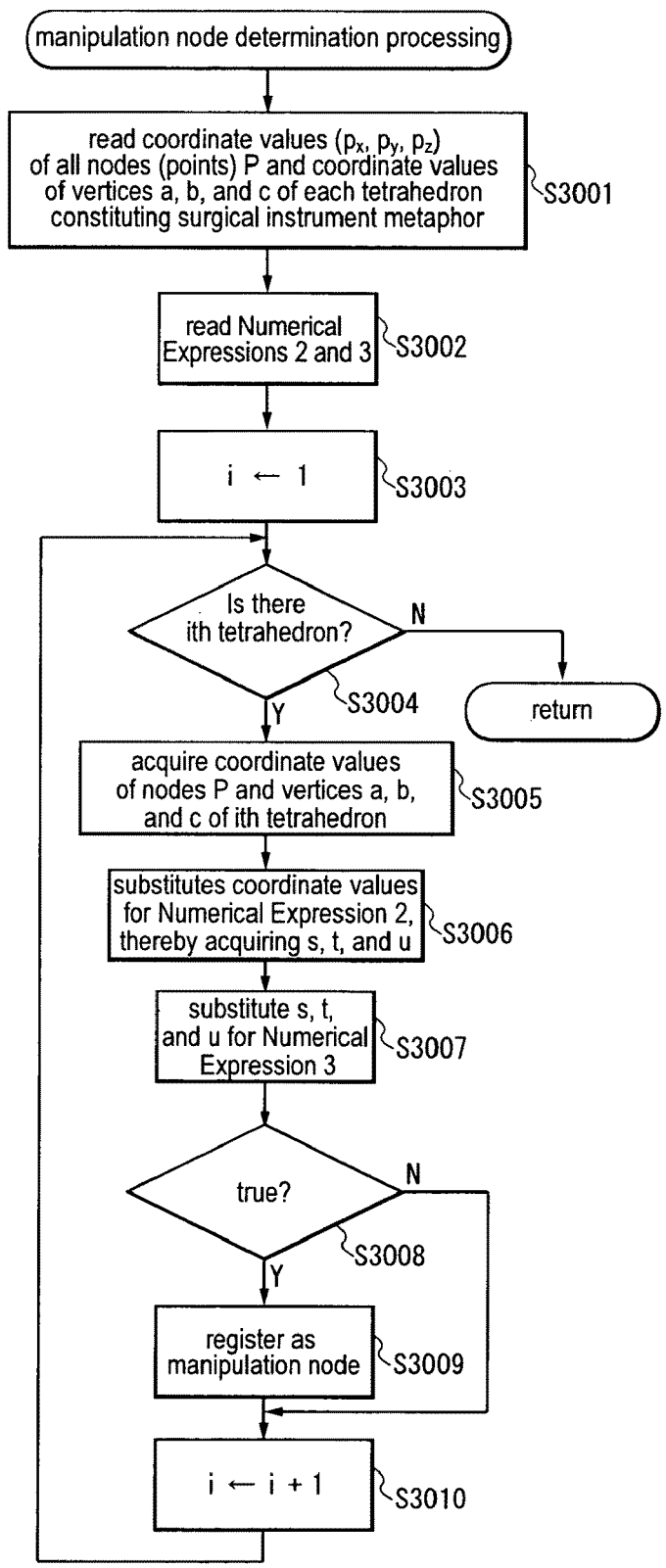
FIG. 30 is a flowchart illustrating manipulation node determination processing in the information processing apparatus.
Figure 31:
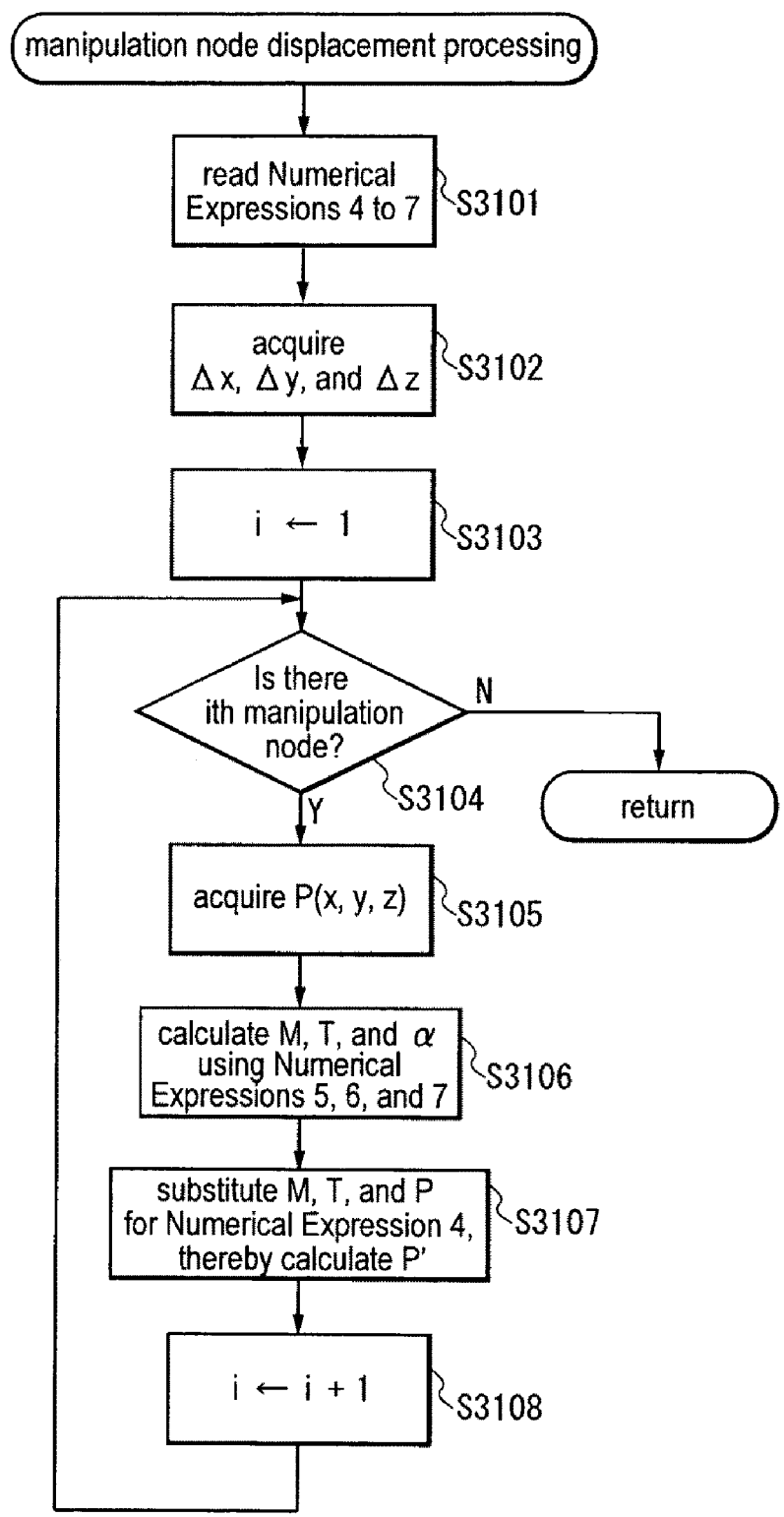
FIG. 31 is a flowchart illustrating manipulation node displacement processing in the information processing apparatus.
Figure 32A:
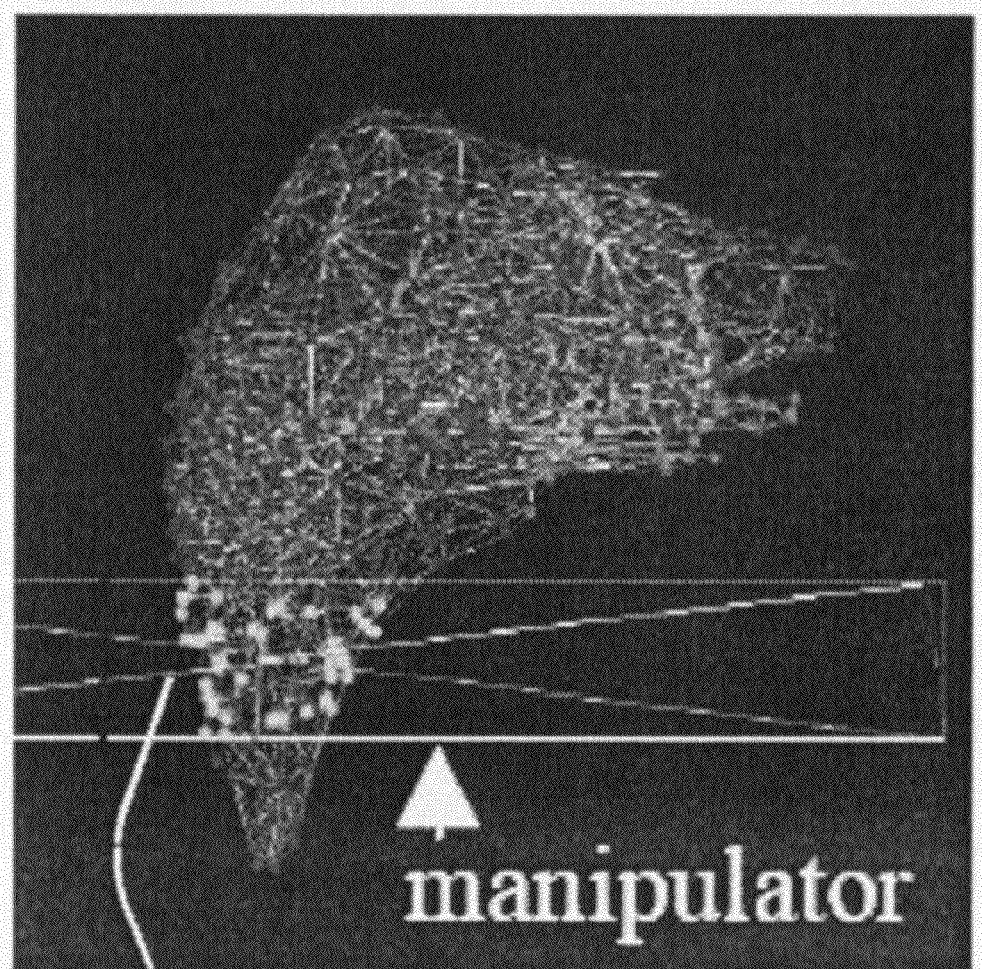
FIG. 32 shows a manner in which a manipulation region is specified in an organ object in the information processing apparatus.
Figure 32B:
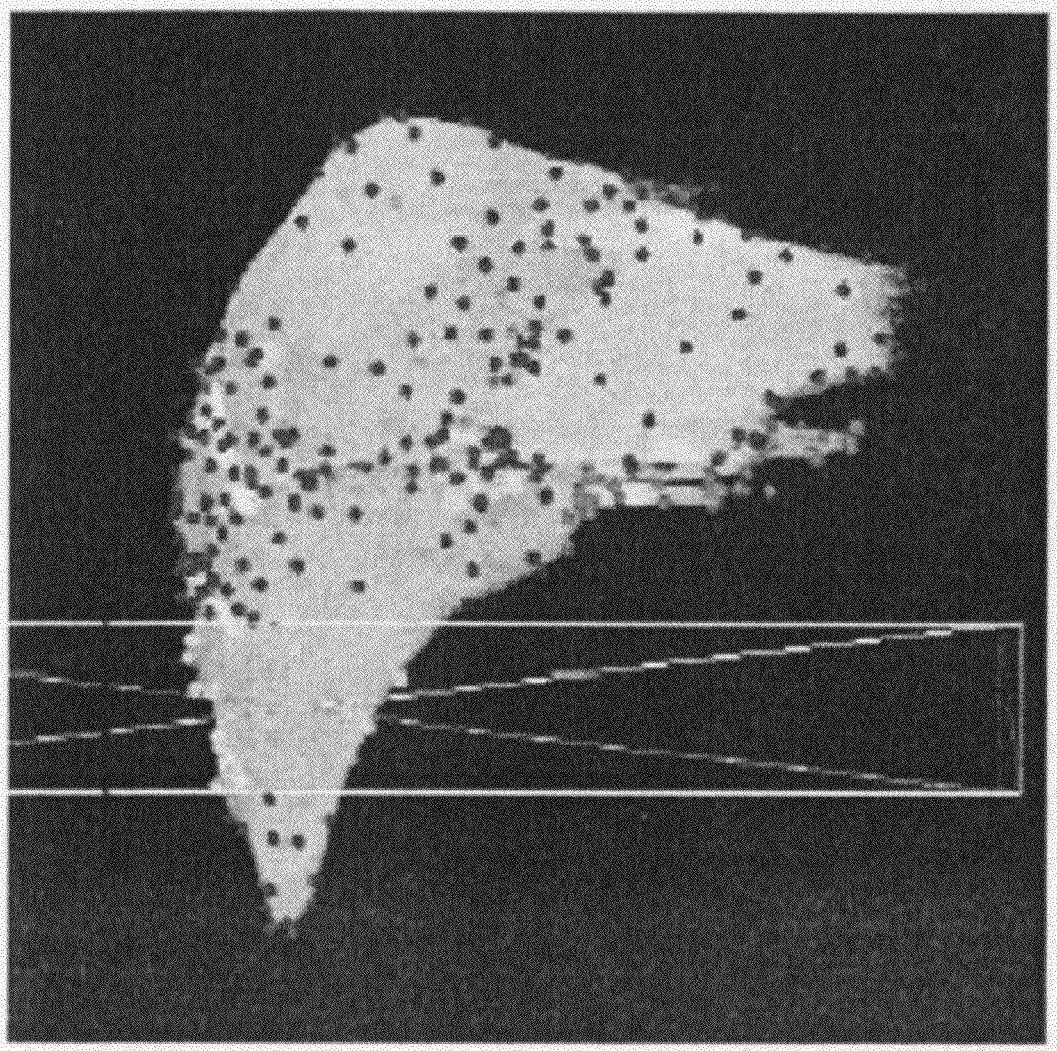
Figure 33A:
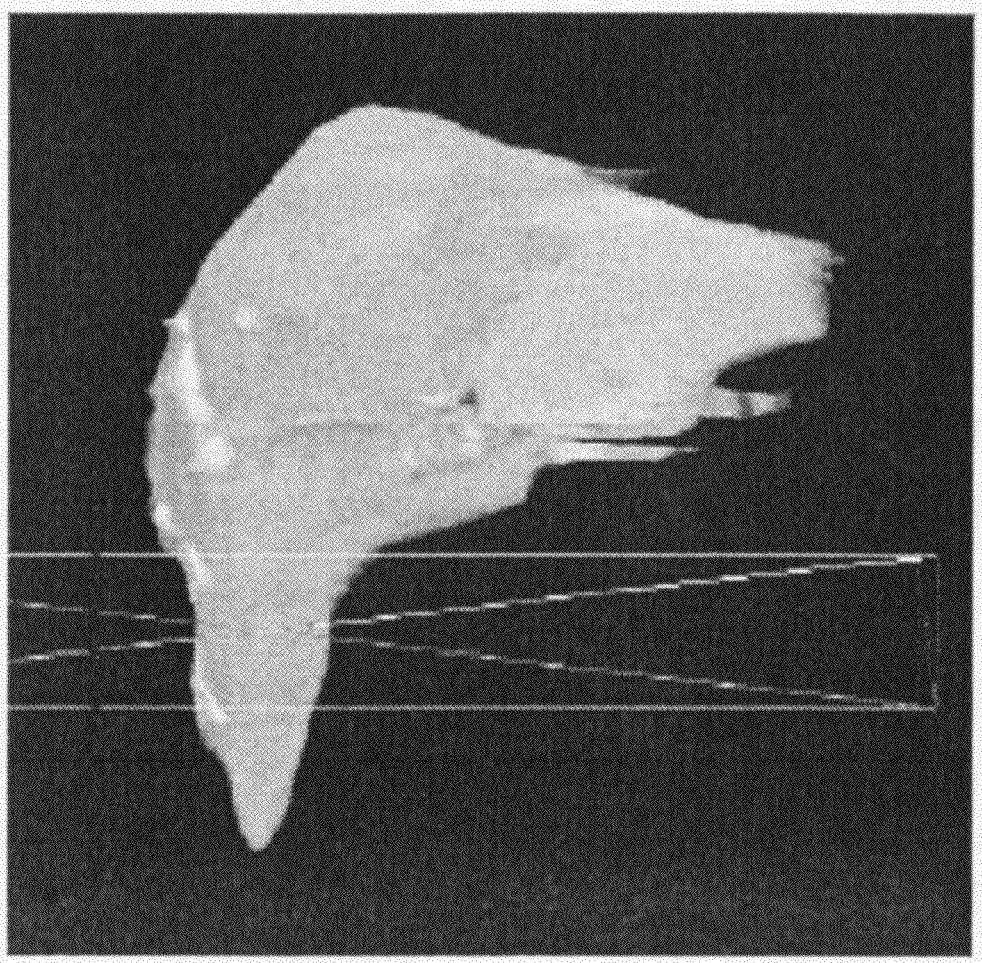
FIG. 33 shows a volume image of the liver in the case of performing a pinching manipulation in the information processing apparatus.
Figure 33B:
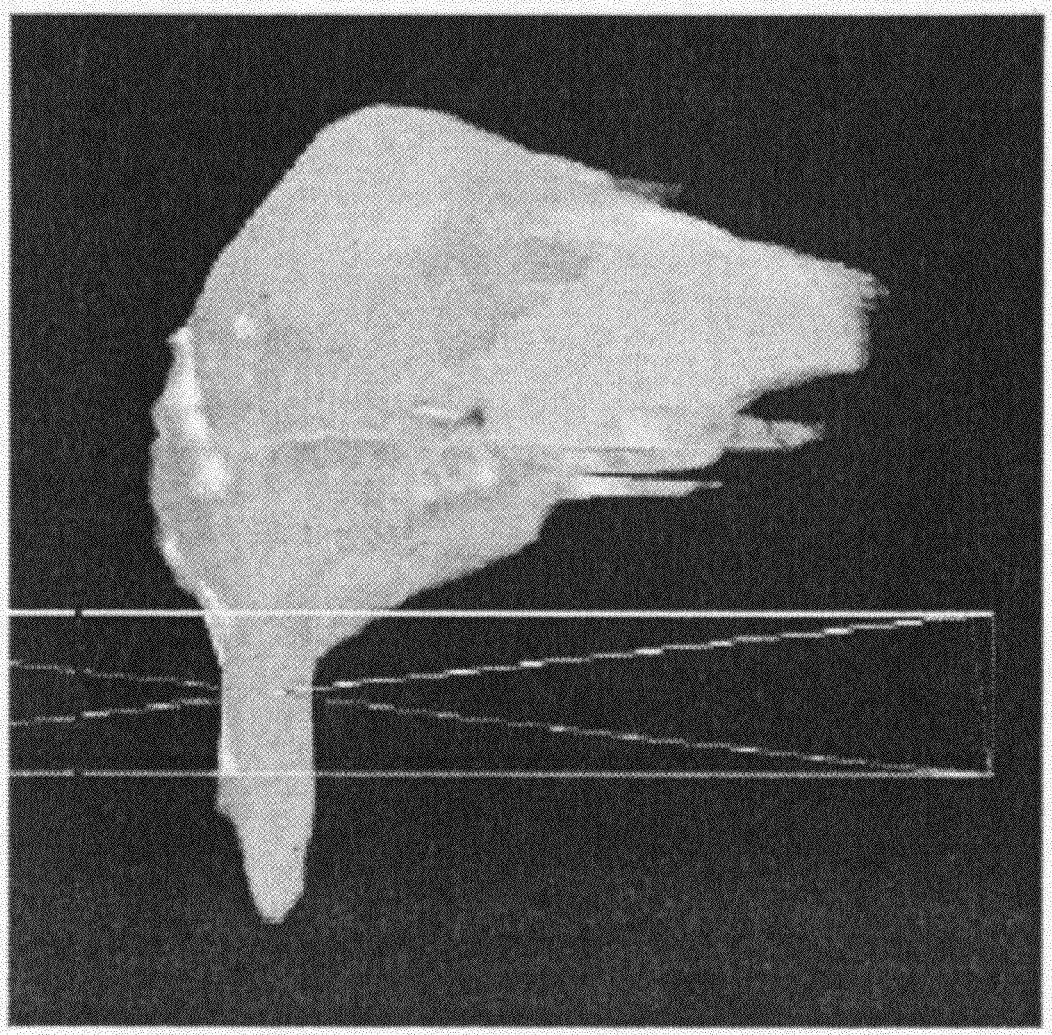
Figure 34A:
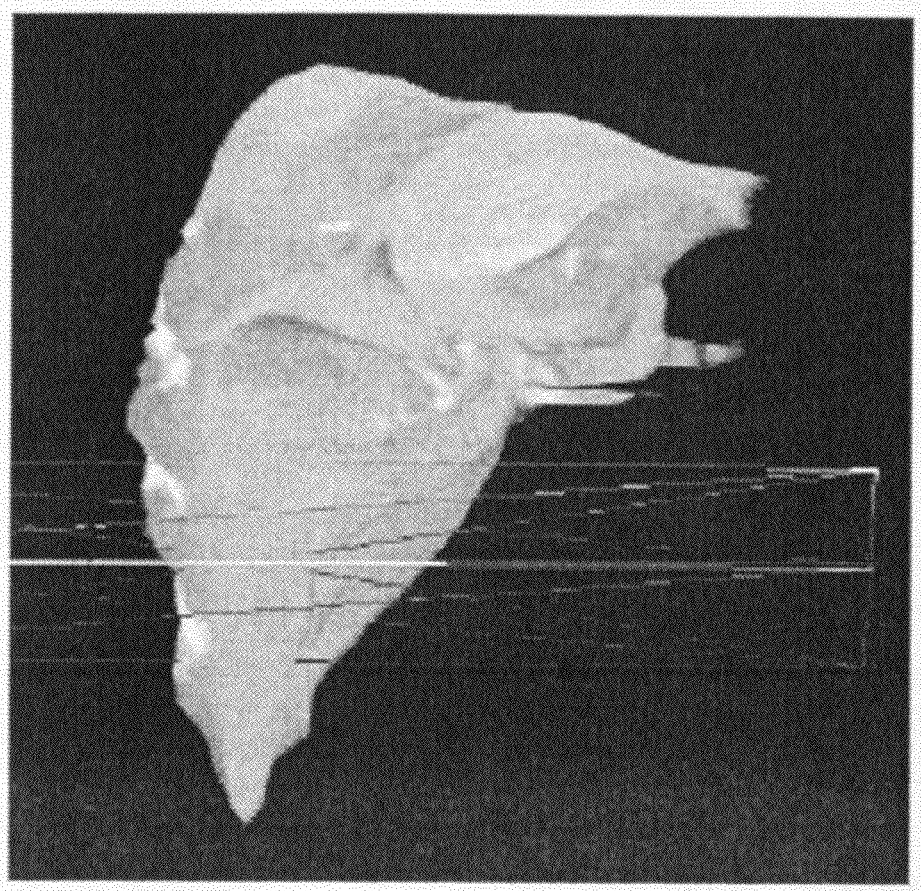
FIG. 34 shows a volume image of the liver in the case of performing a rotation manipulation in the information processing apparatus
Figure 34B:
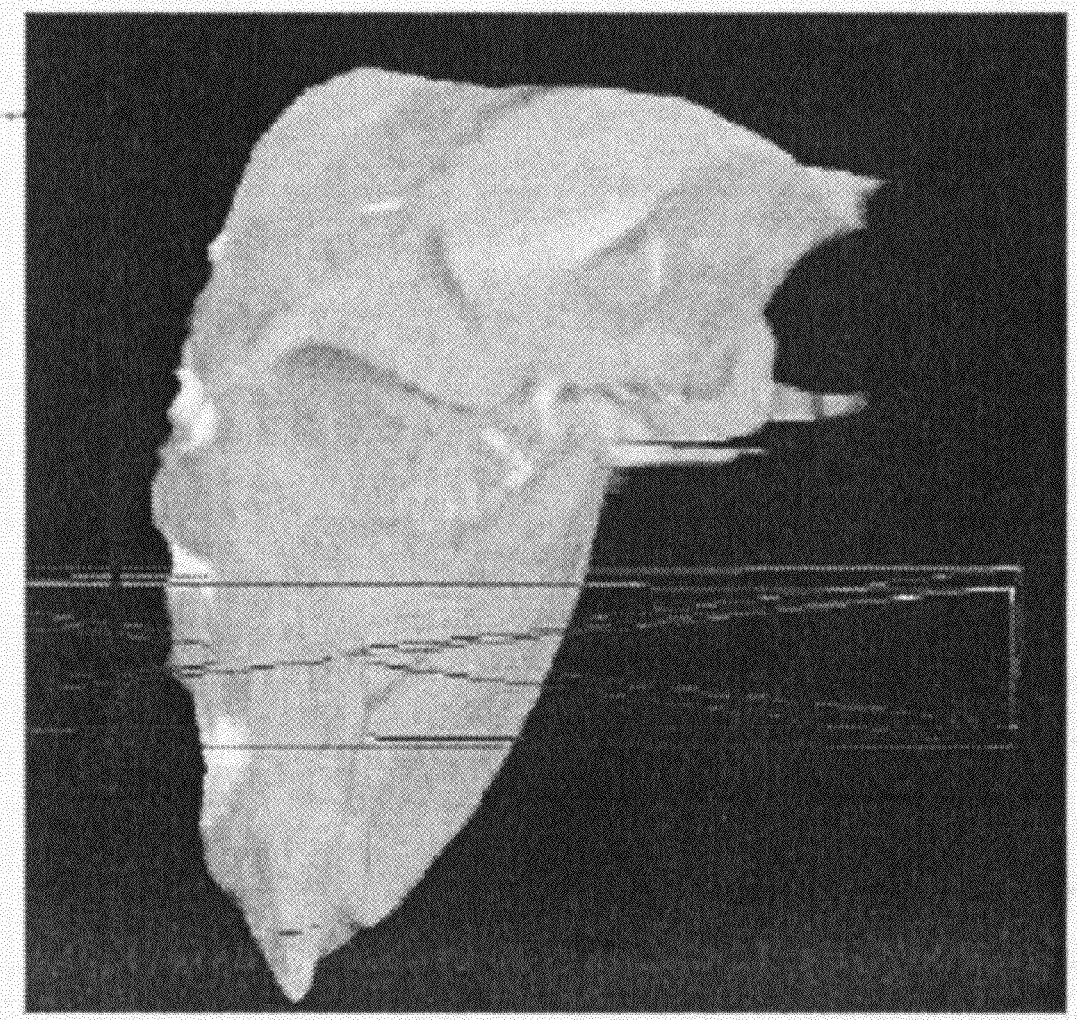
Figure 35:
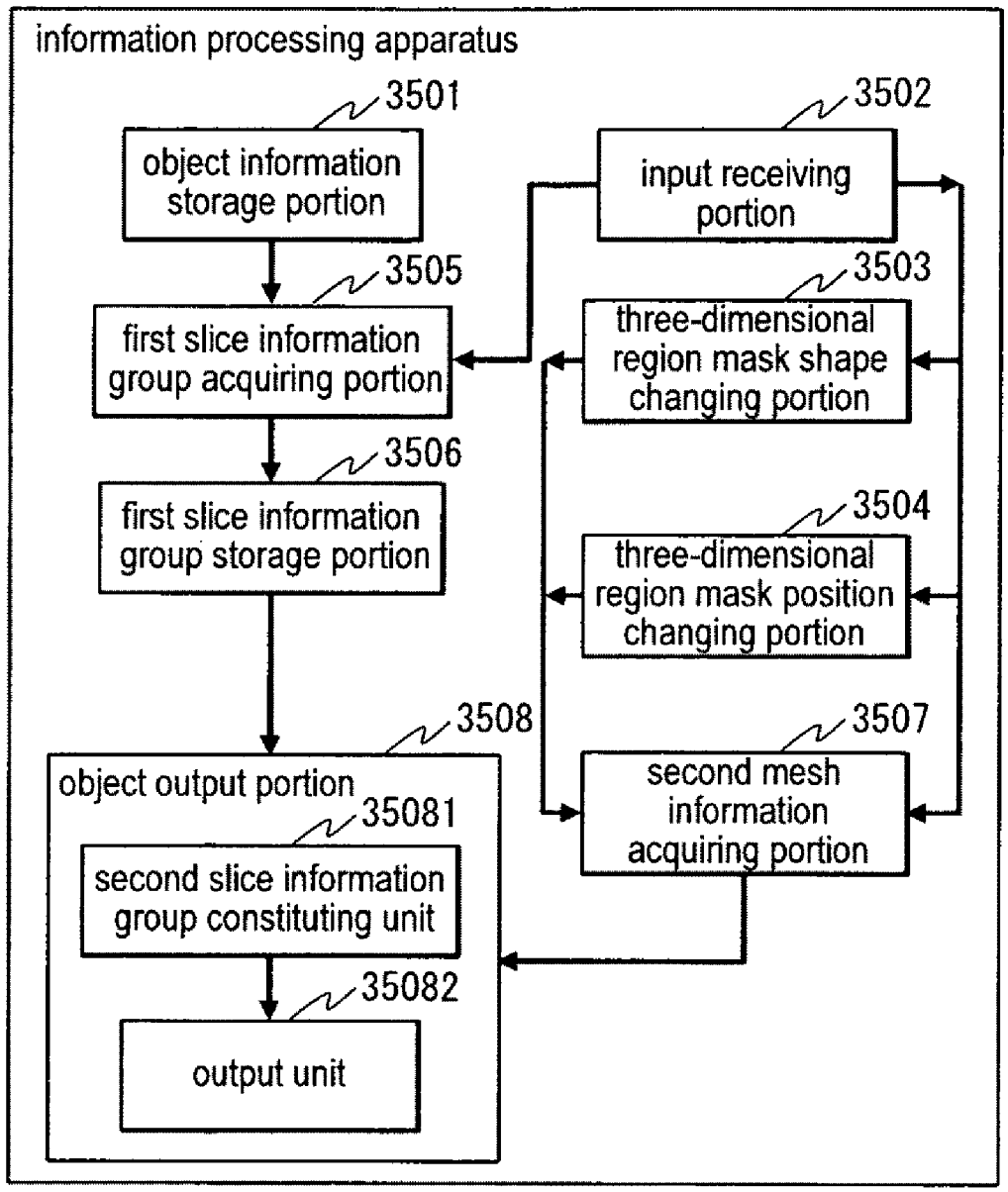
FIG. 35 is a block diagram of an information processing apparatus in Embodiment 4.
Figure 36:
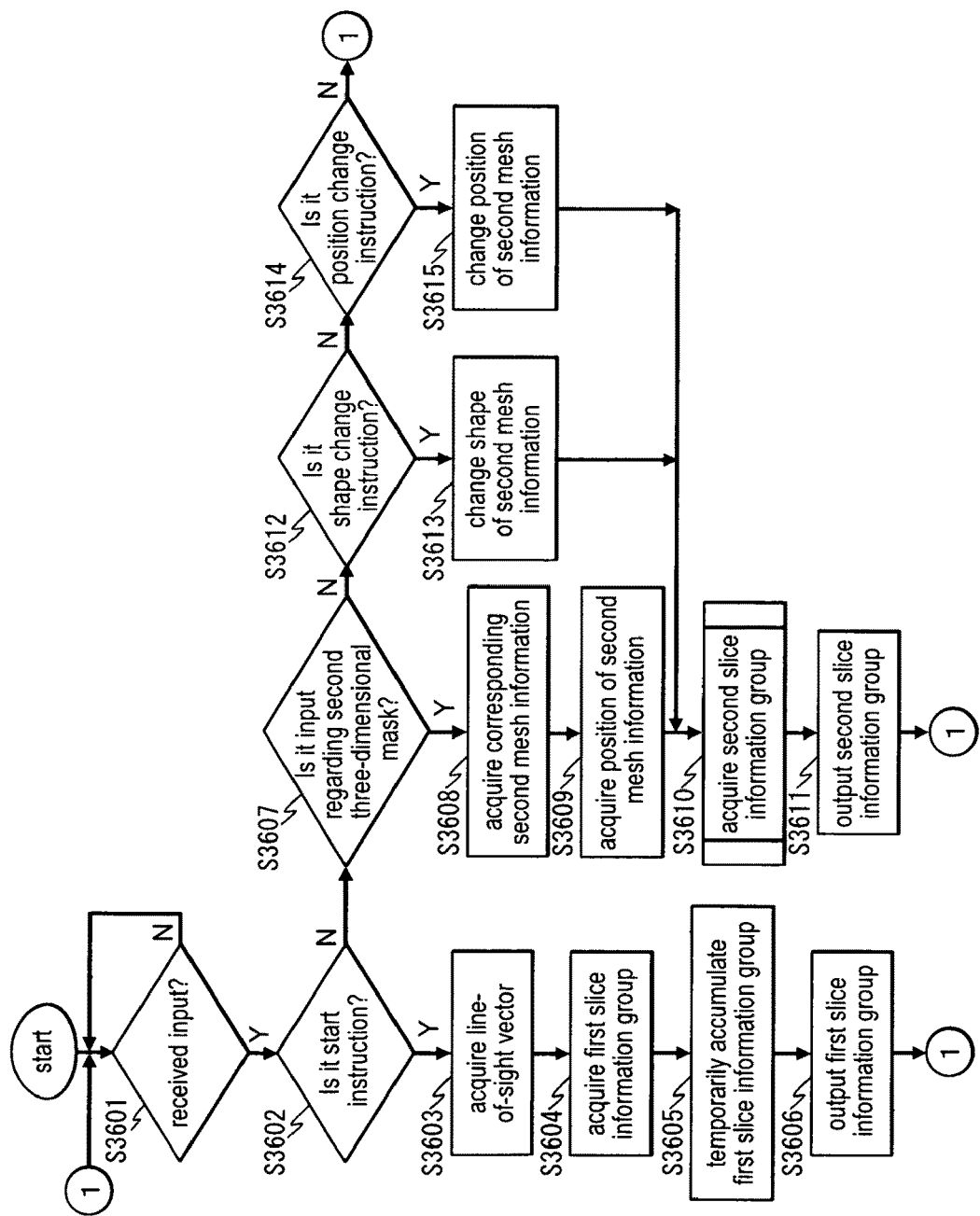
FIG. 36 is a flowchart illustrating the operation of the information processing apparatus.
Figure 37:
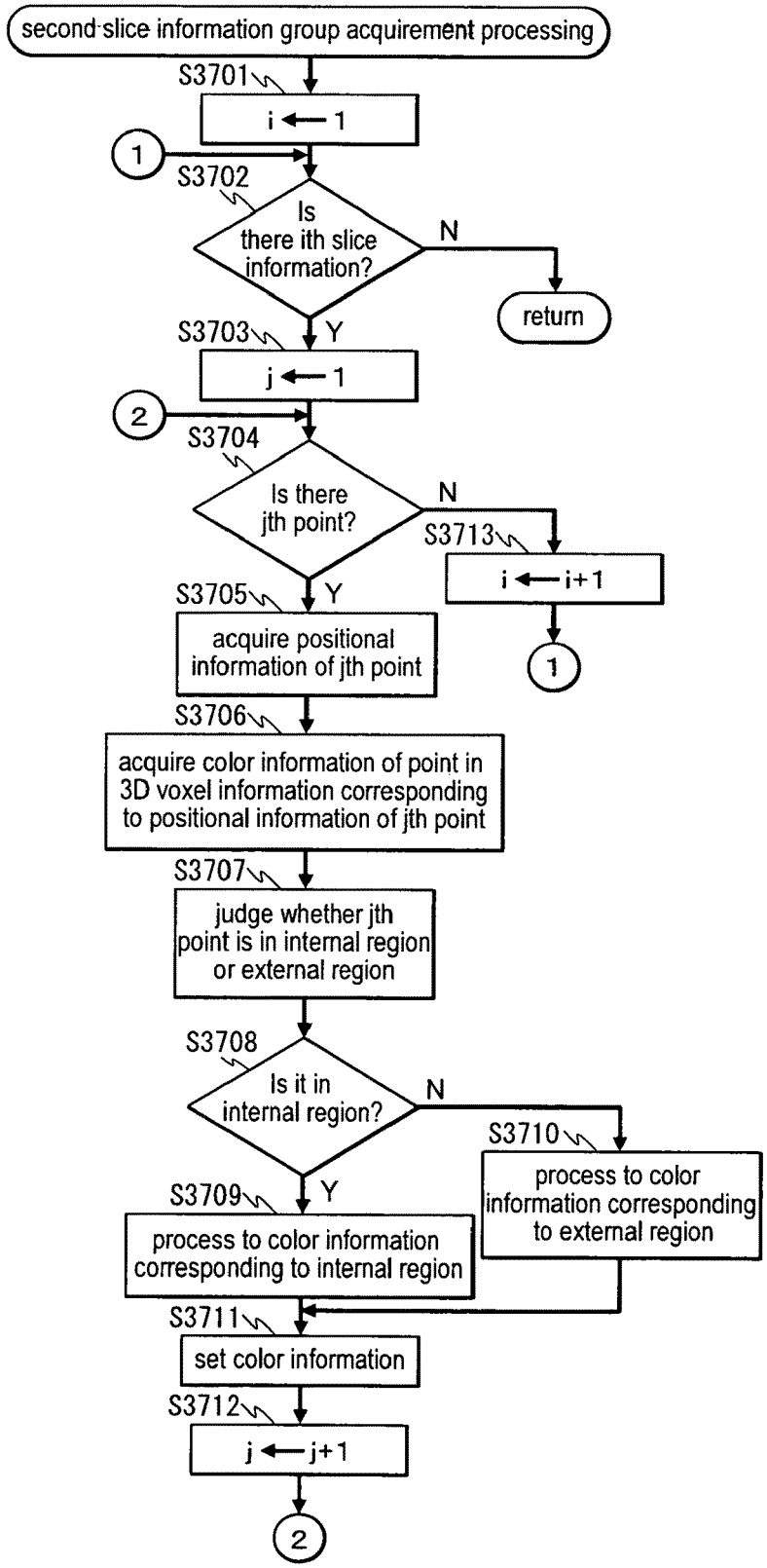
FIG. 37 is a flowchart illustrating the operation of second slice information group acquiring processing in the information processing apparatus.
Figure 38:
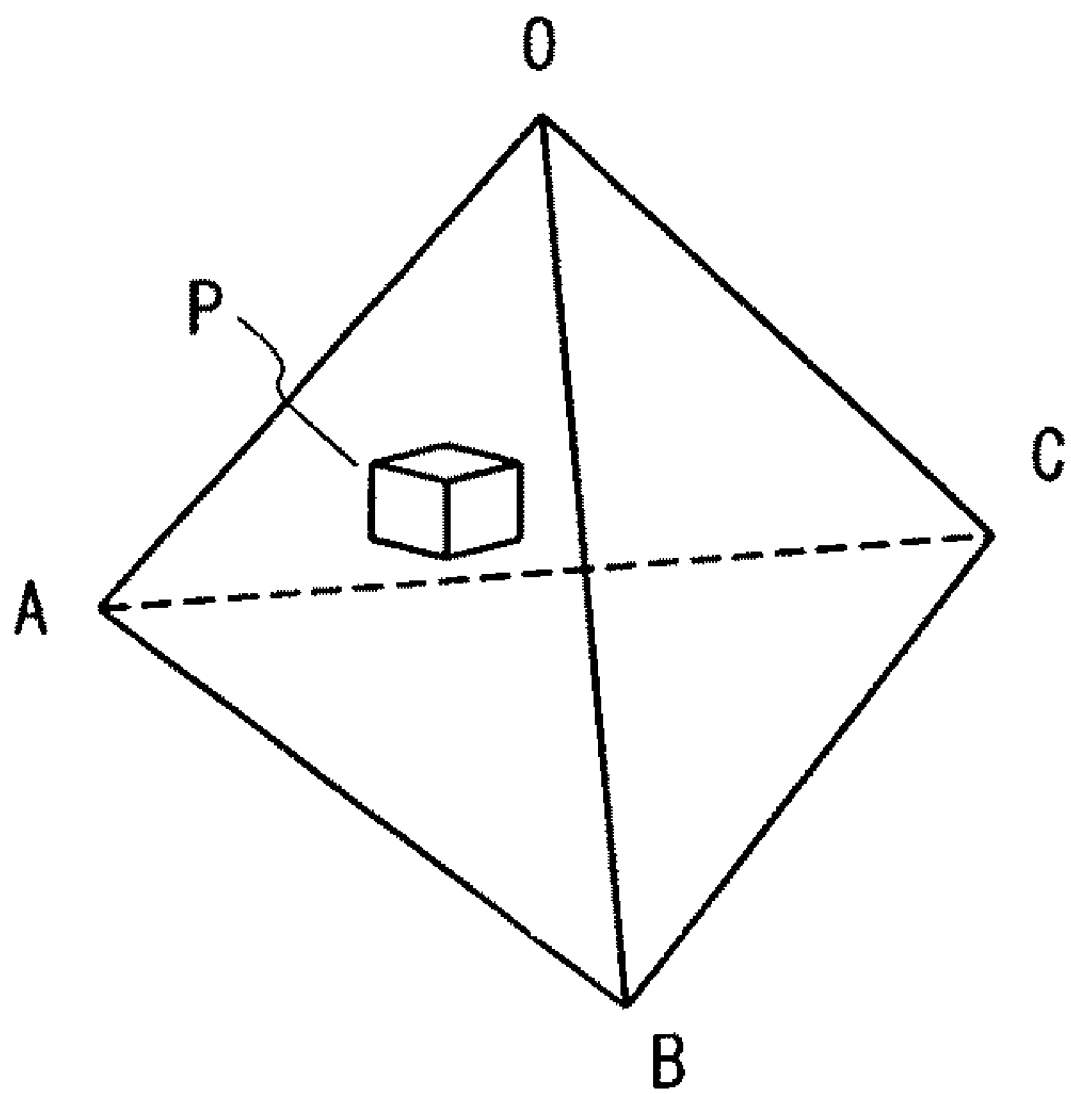
FIG. 38 is a diagram for illustrating data structure in the information processing apparatus.
Figure 41:
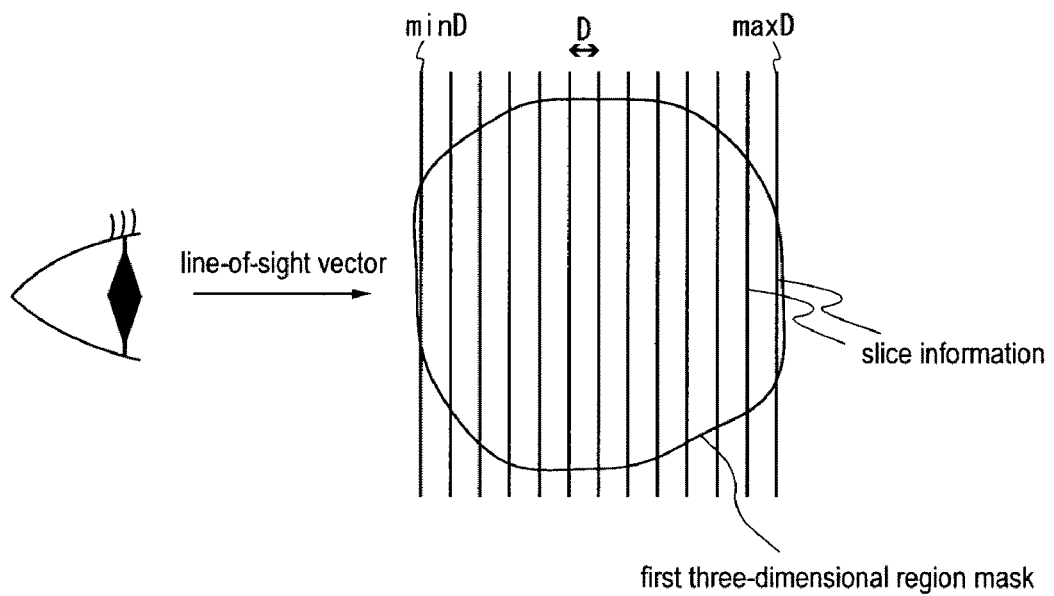
FIG. 41 shows an image at the time of acquiring a first slice information group in the information processing apparatus.
Figure 42:
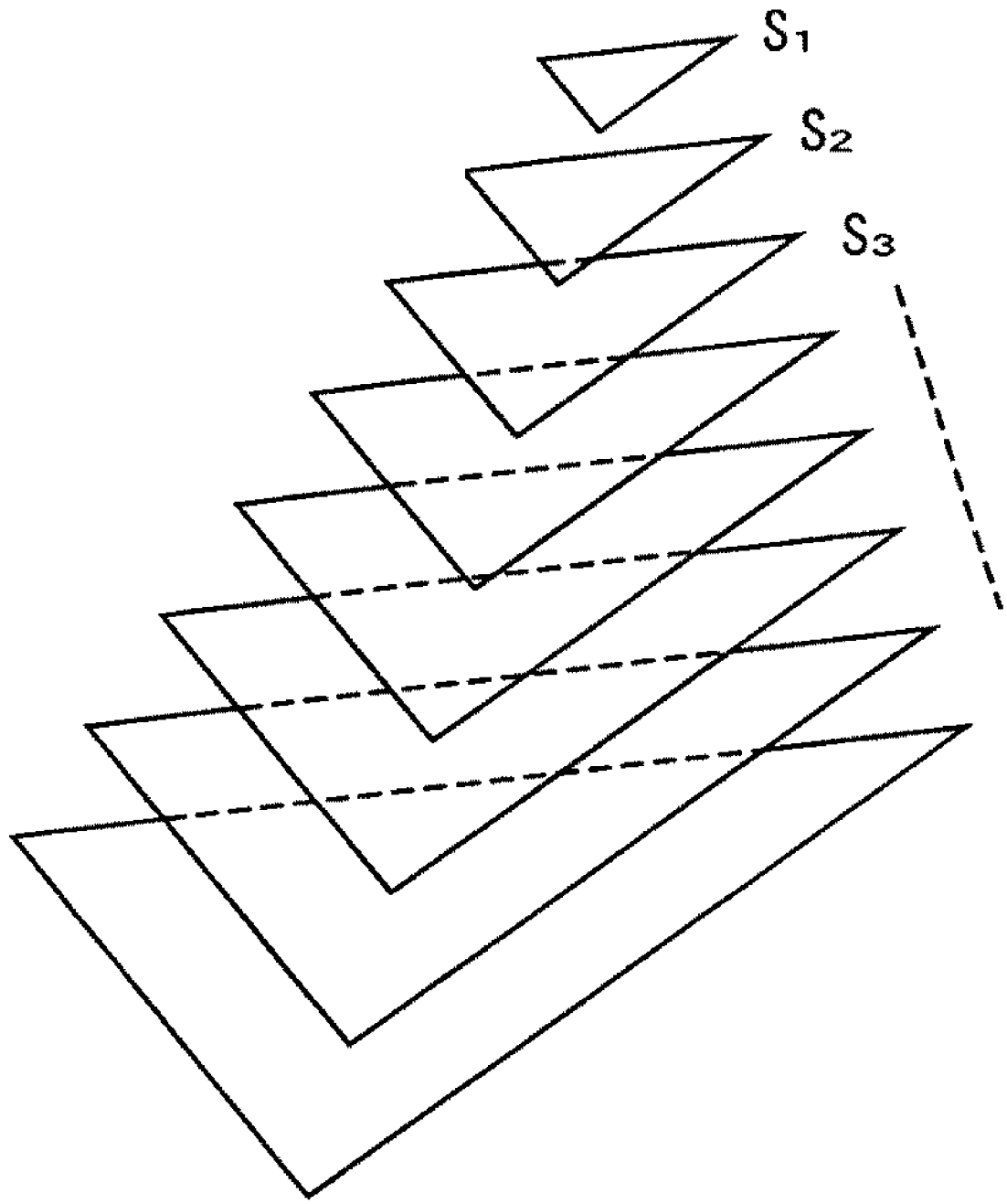
FIG. 42 shows the first slice information group.
Figure 43:
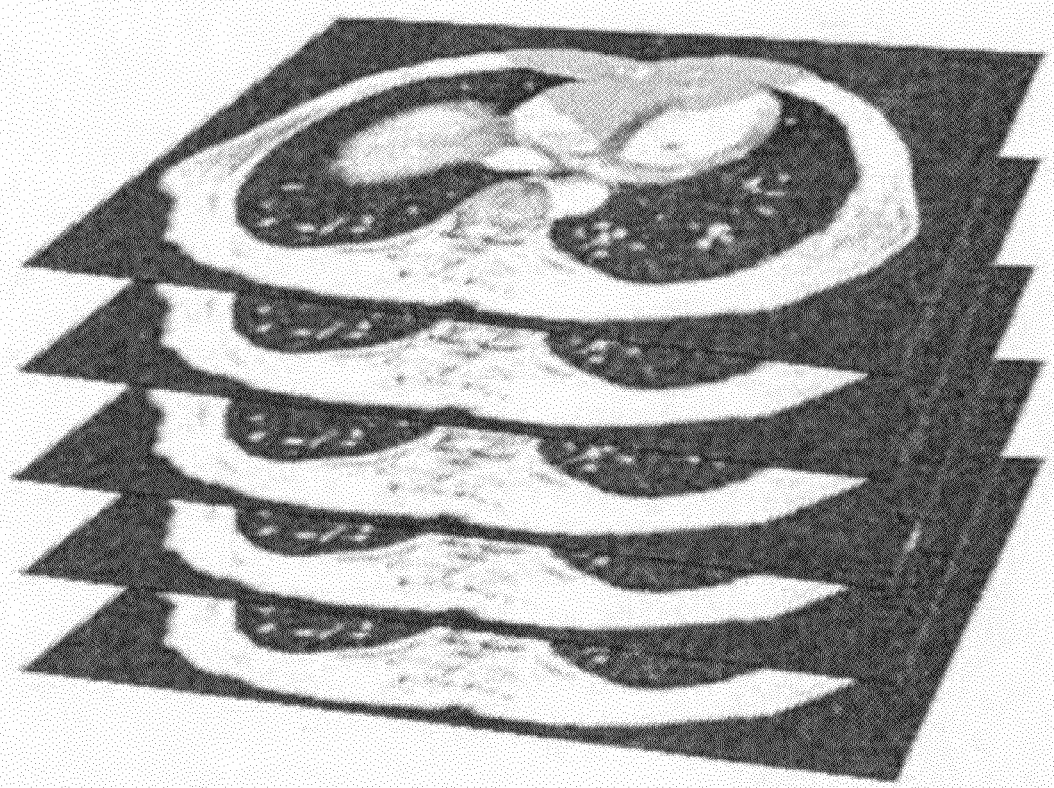
FIG. 43 shows the 3D voxel information.
Figure 44:
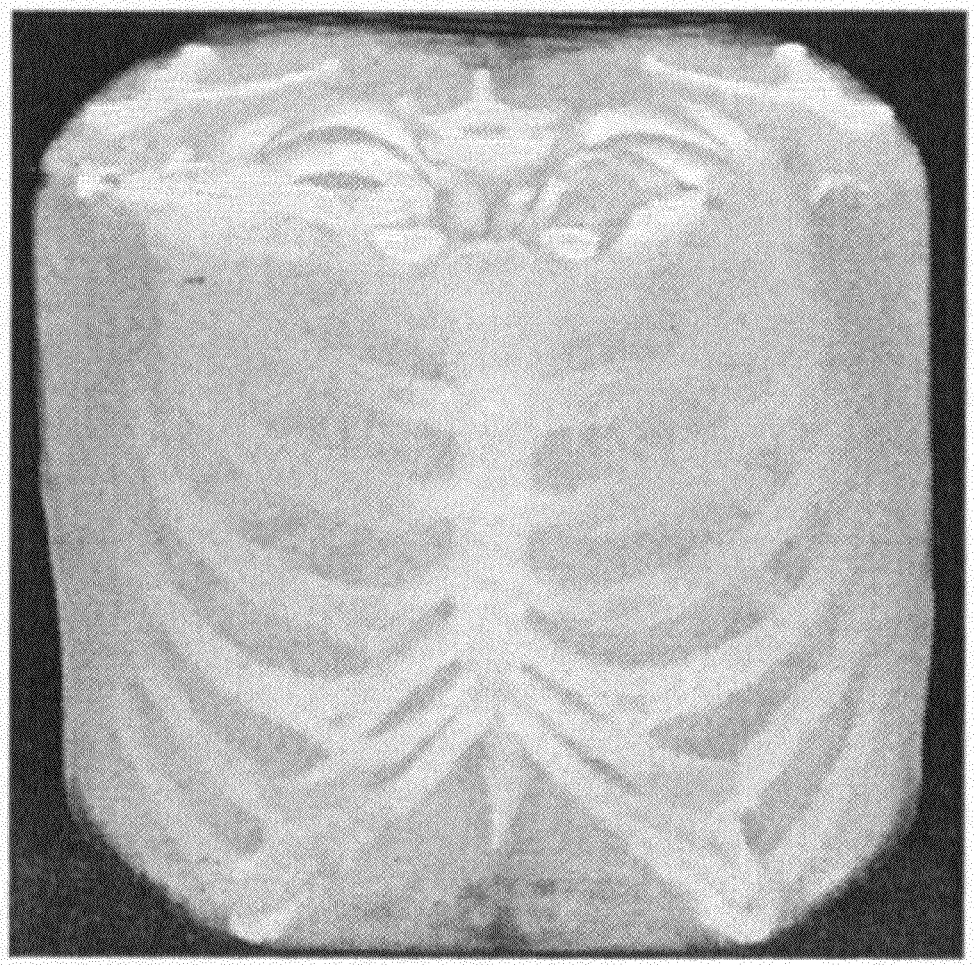
FIG. 44 shows a display example in the information processing apparatus.
Figure 45:
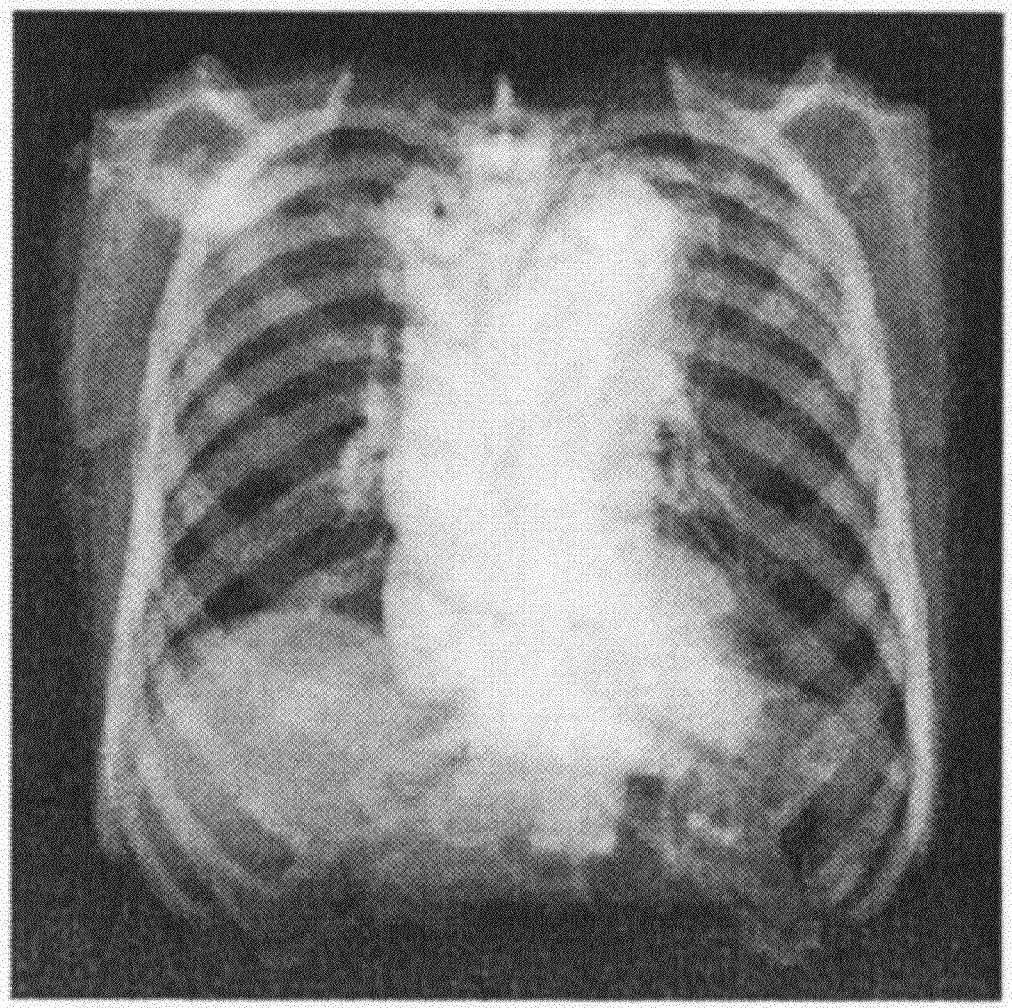
FIG. 45 shows a display example in the information processing apparatus.
Figure 46:
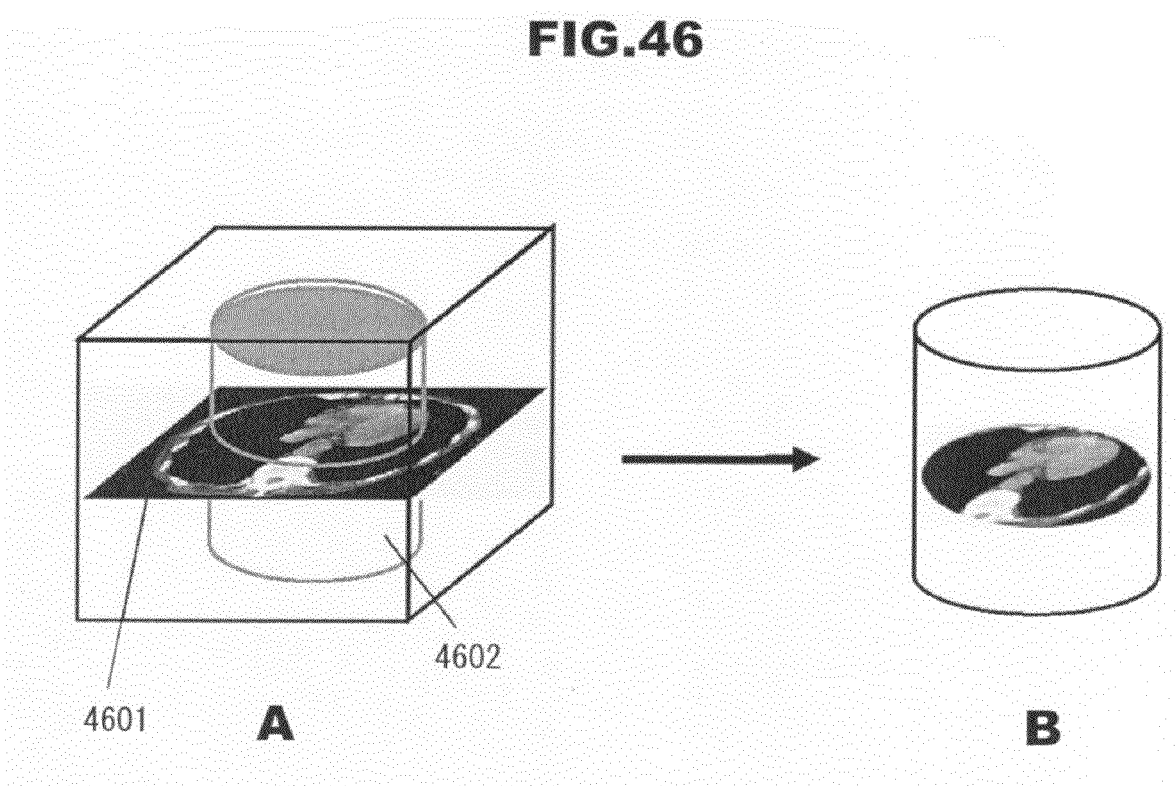
FIG. 46 illustrates a concept of processing in which a second slice information group is constituted in the information processing apparatus.
Figure 47:
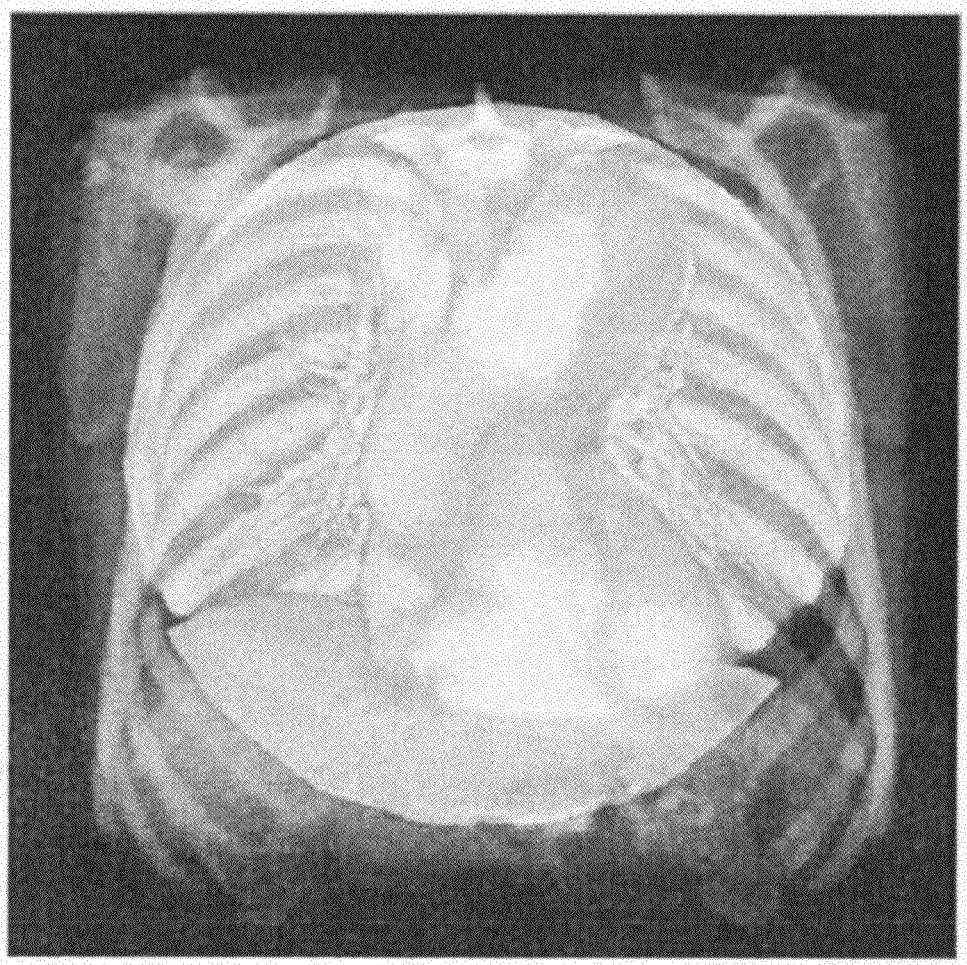
FIG. 47 shows a display example in the information processing apparatus.
Figure 48:
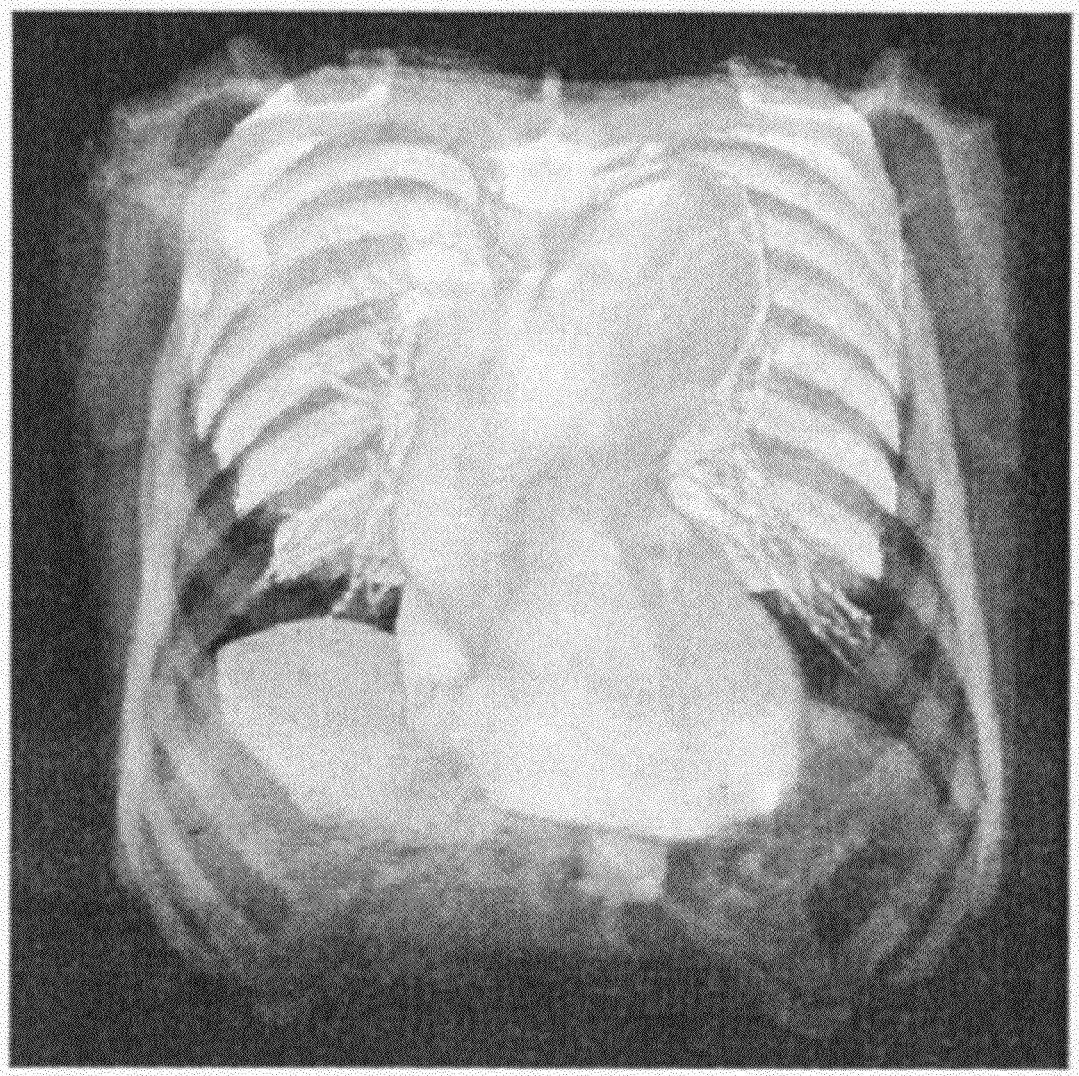
FIG. 48 shows a display example in the information processing apparatus.
Figure 49A:
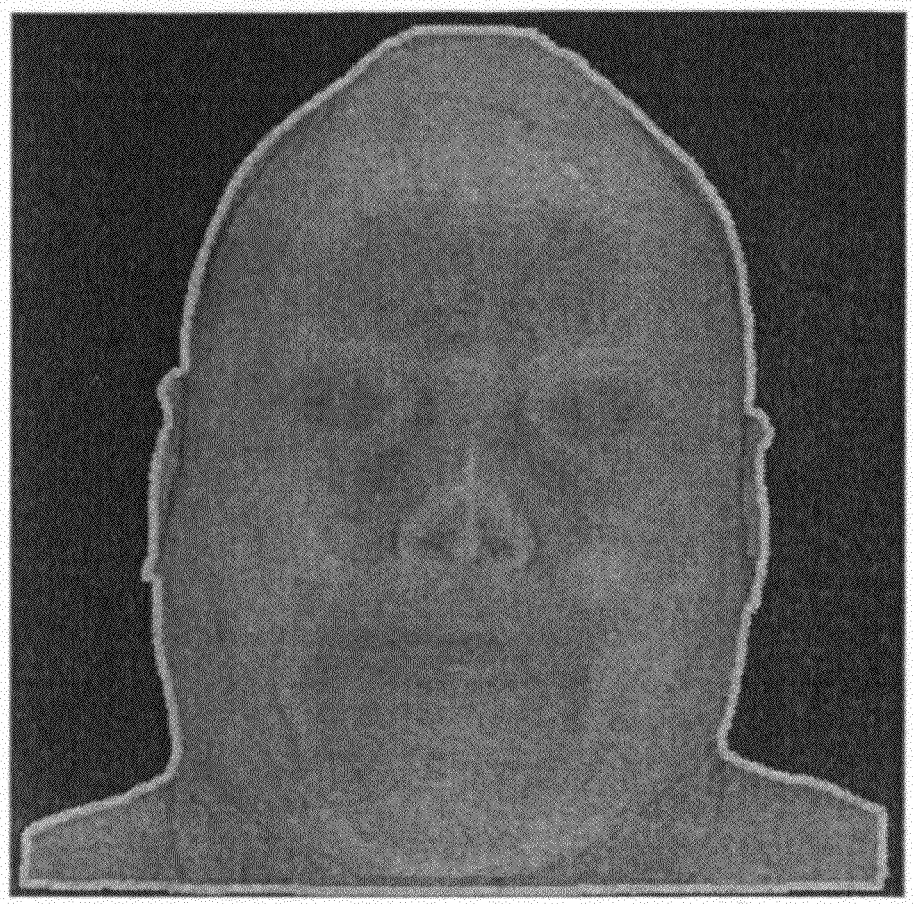
FIG. 49 shows a display example in the information processing apparatus.
Figure 49B:
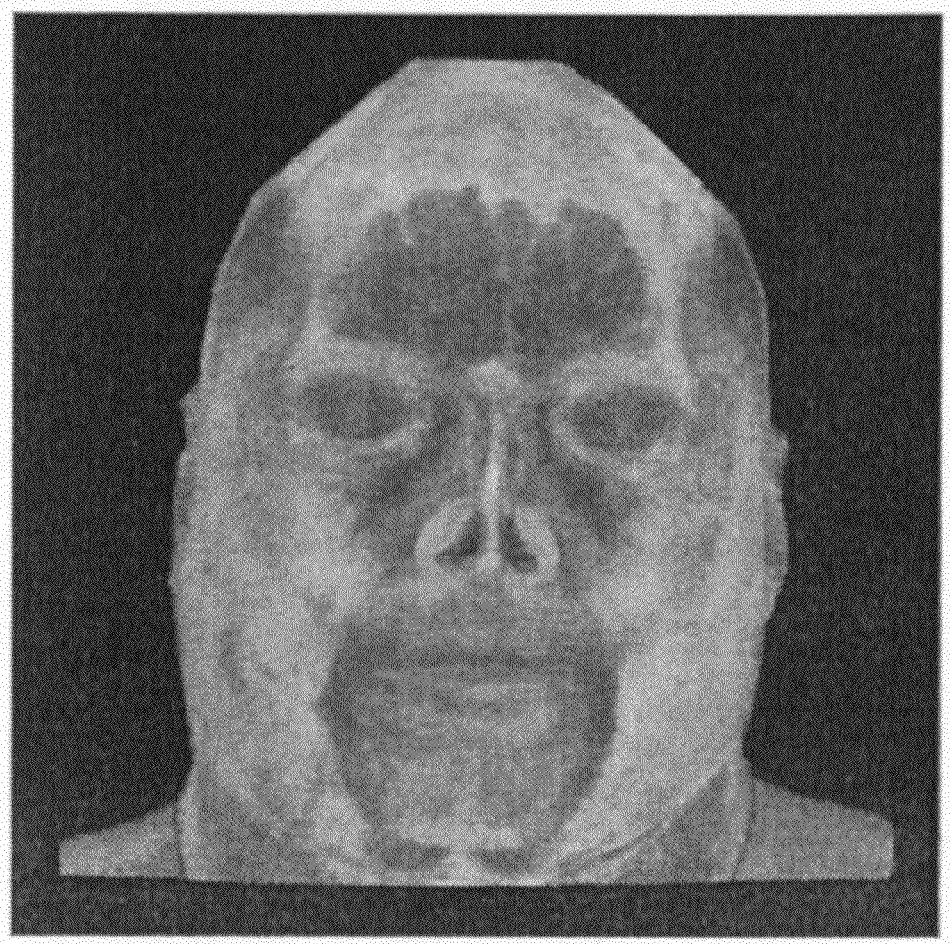
Figure 49C:
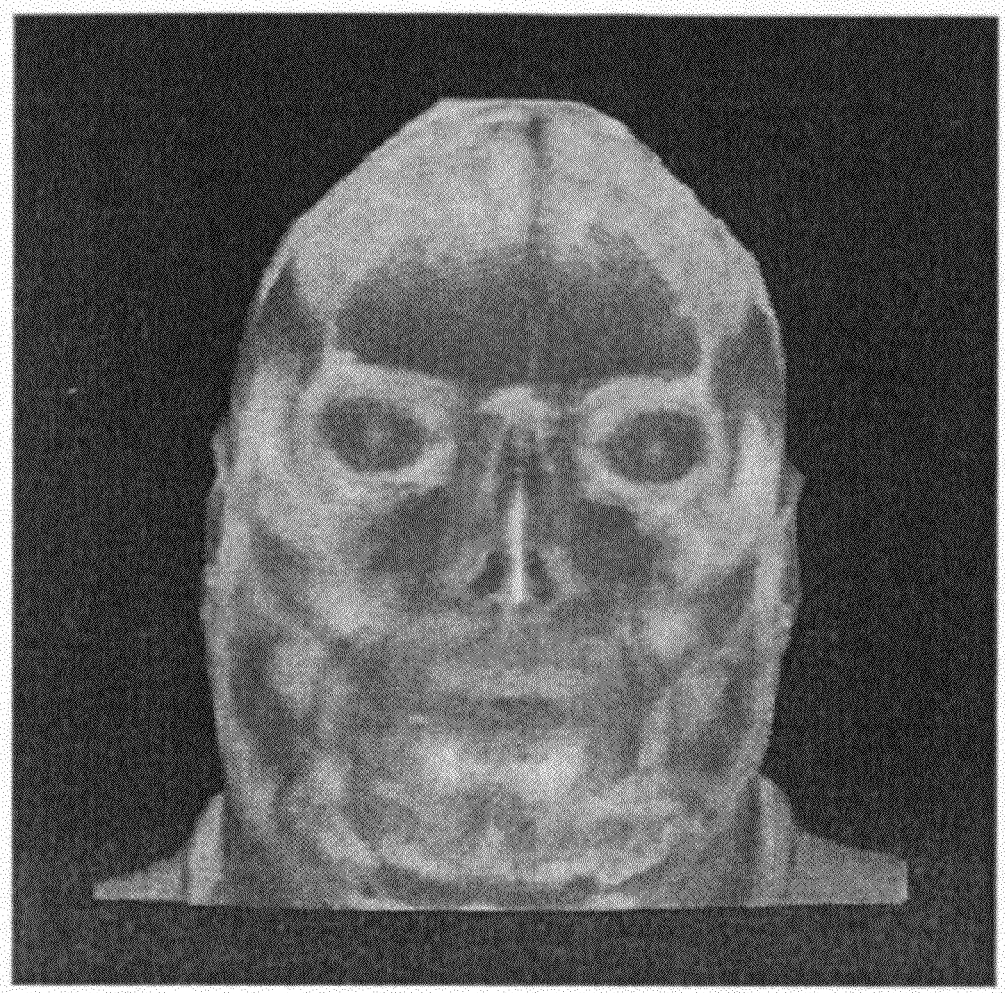
Figure 49D:
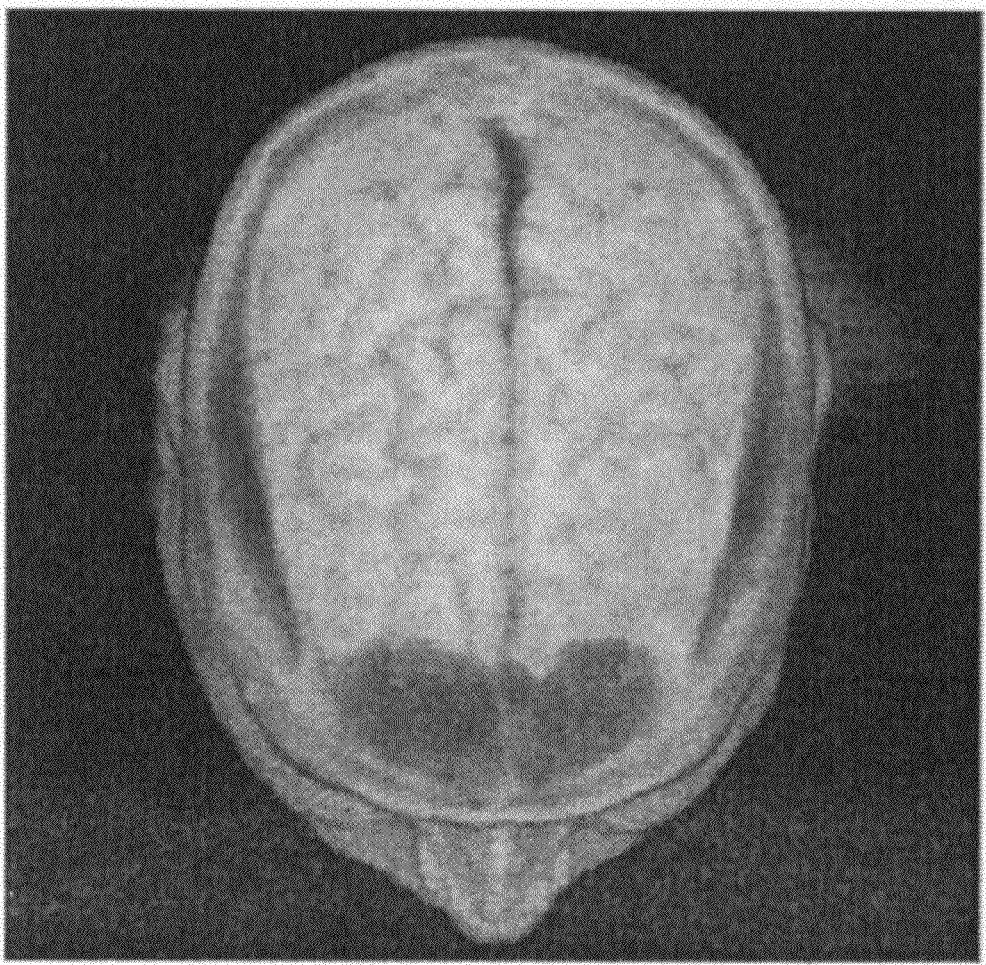
Figure 50:
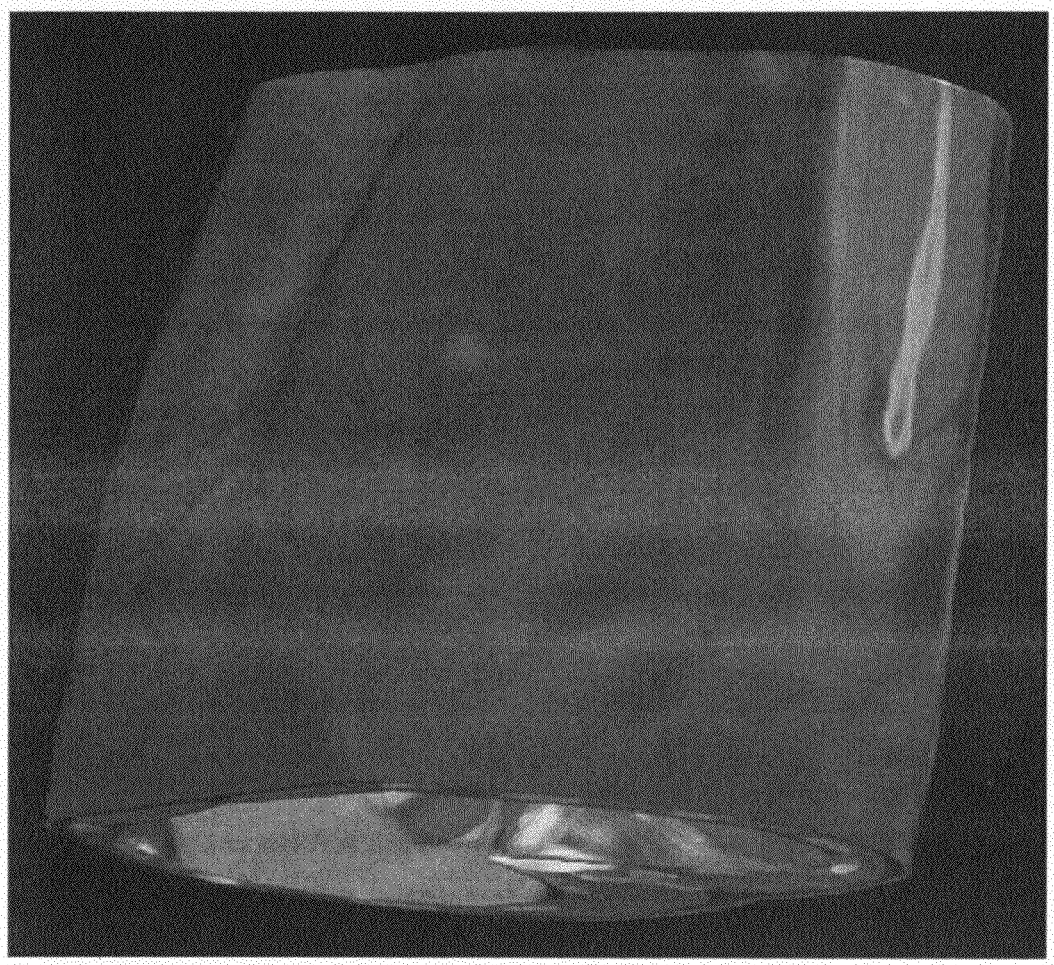
FIG. 50 shows a display example in the information processing apparatus.
Figure 51:
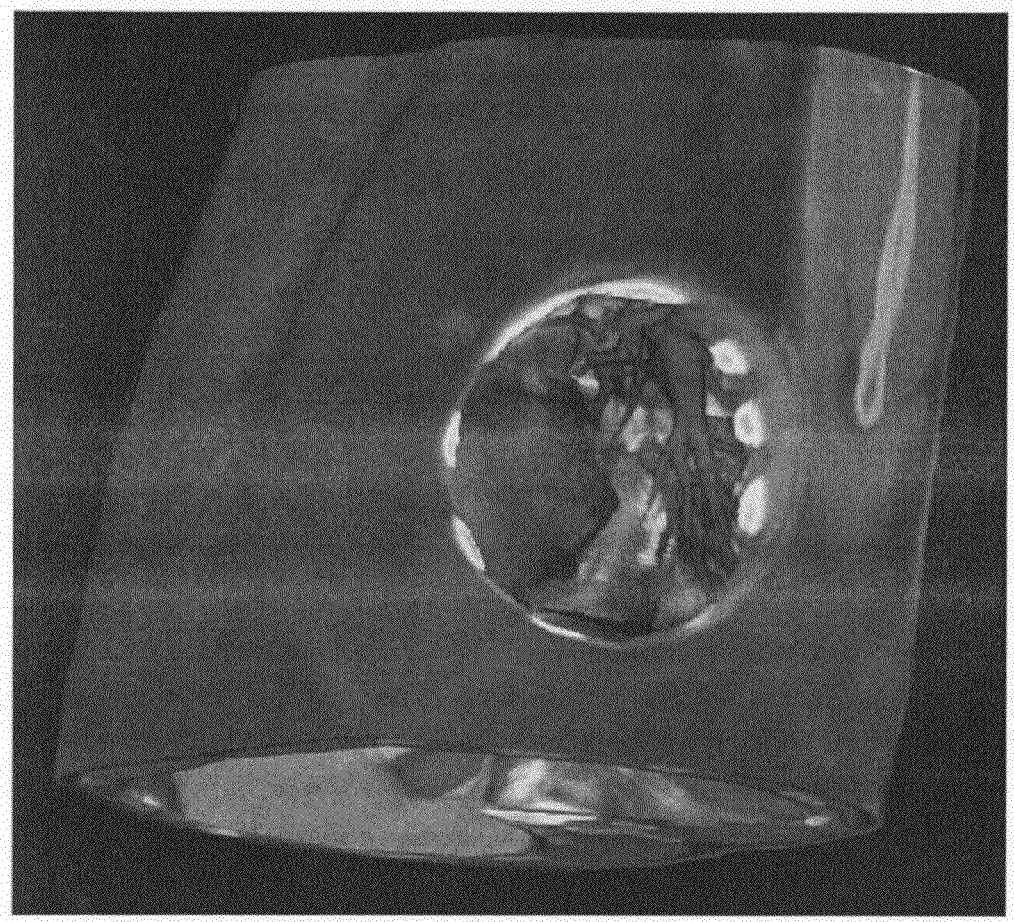
FIG. 51 shows a display example in the information processing apparatus.
Figure 52:
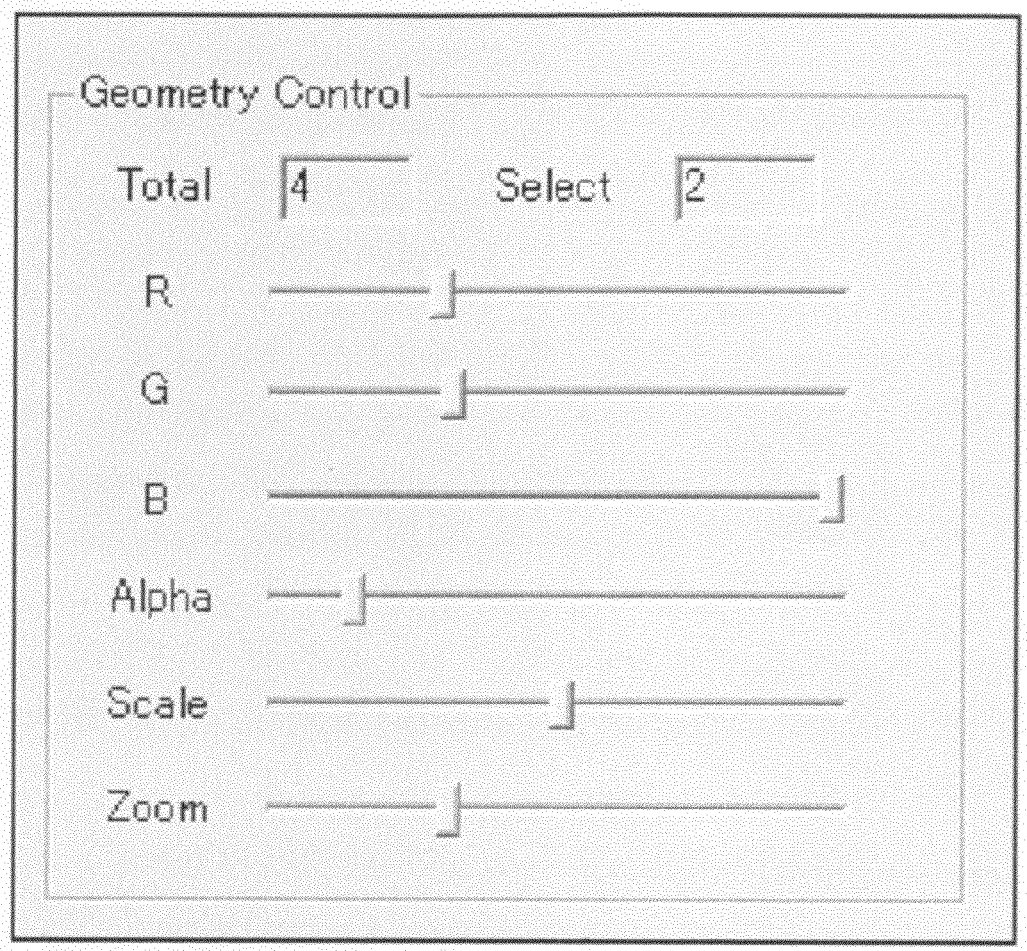
FIG. 52 shows an example of an input screen in the information processing apparatus.
Figure 53:
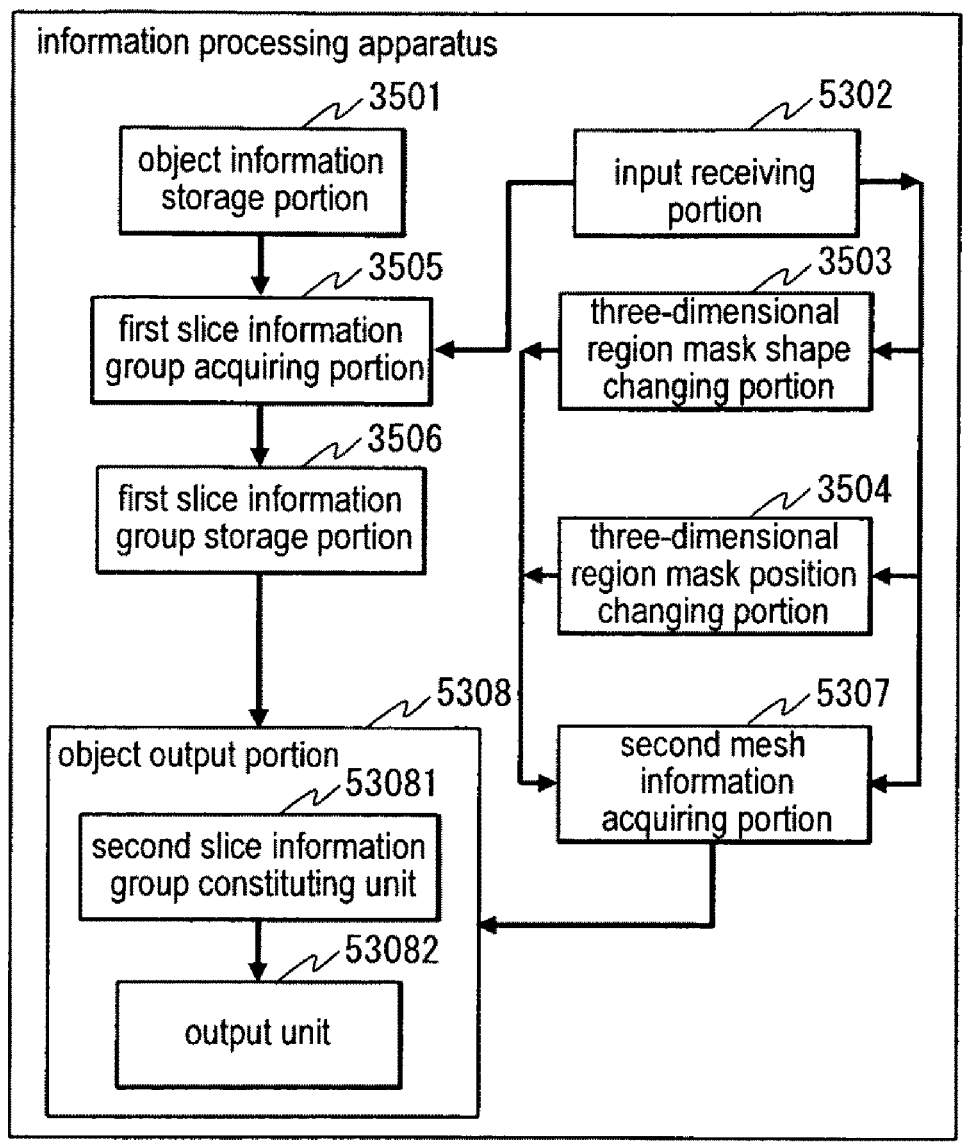
FIG. 53 is a block diagram of an information processing apparatus in Embodiment 5.
Figure 54:
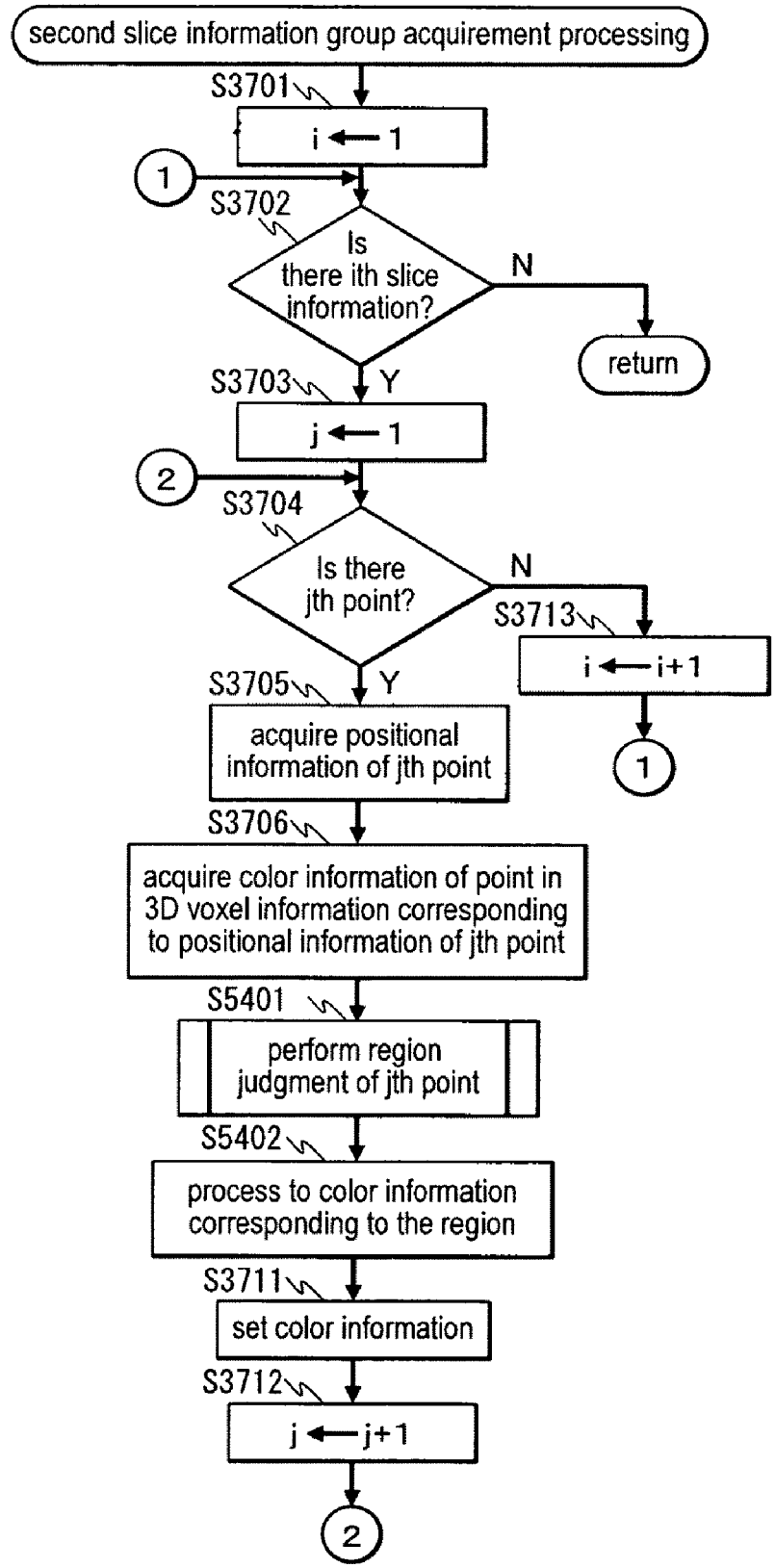
FIG. 54 is a flowchart illustrating the operation of the information processing apparatus.
Figure 55:
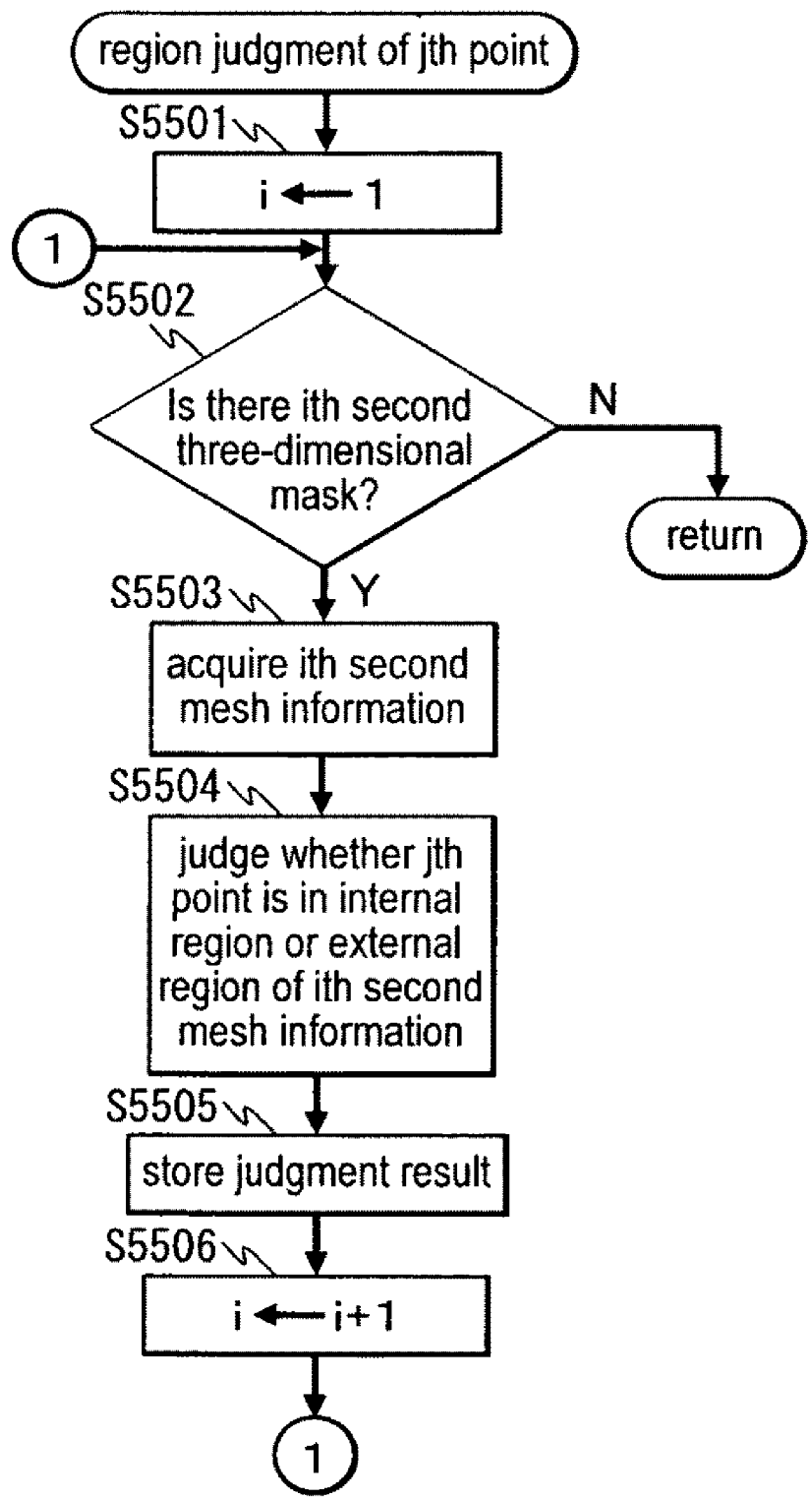
FIG. 55 is a flowchart illustrating the operation of region judgment processing in the information processing apparatus.
Figure 56:
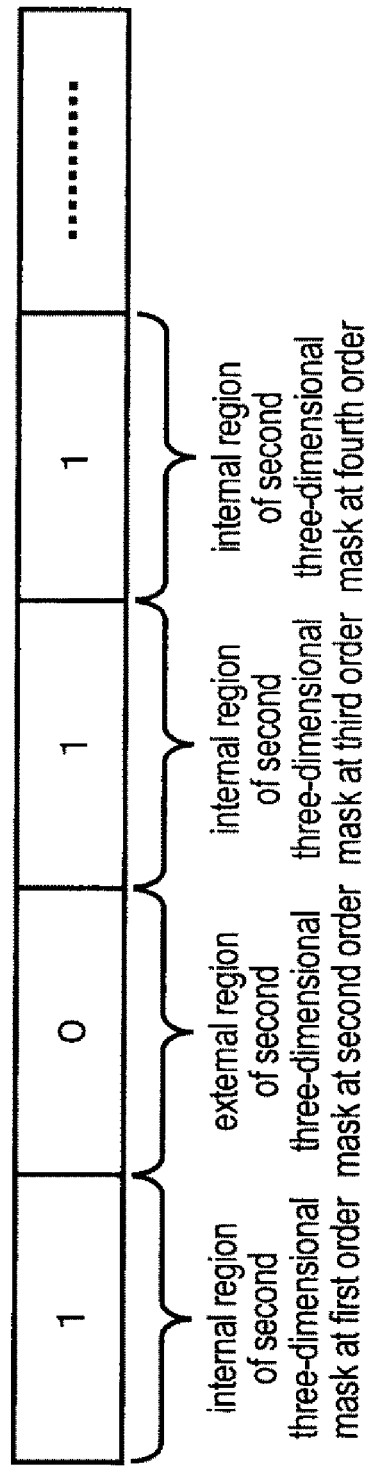
FIG. 56 shows an example of the data structure of region information in the information processing apparatus.
Figure 57:
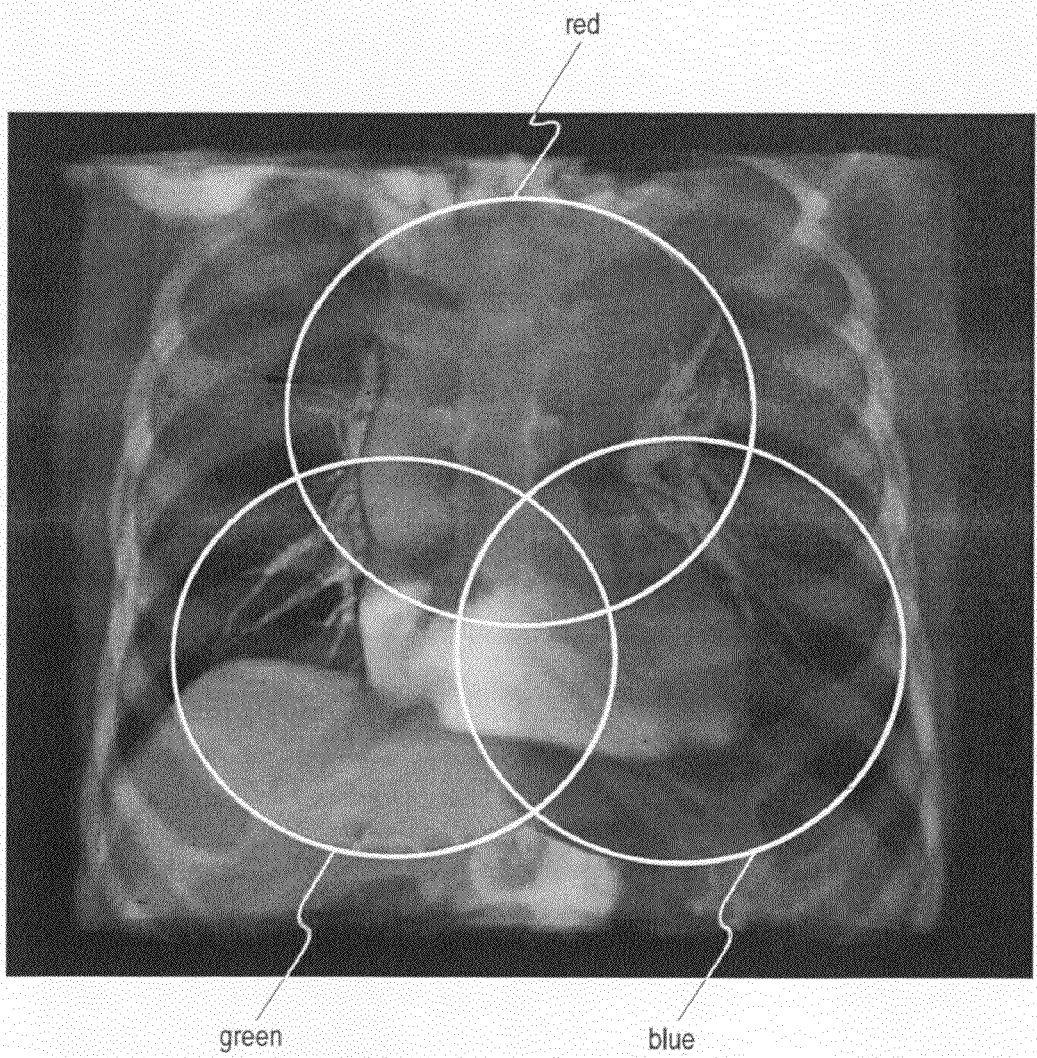
FIG. 57 shows a display example in the information processing apparatus.
Figure 58:
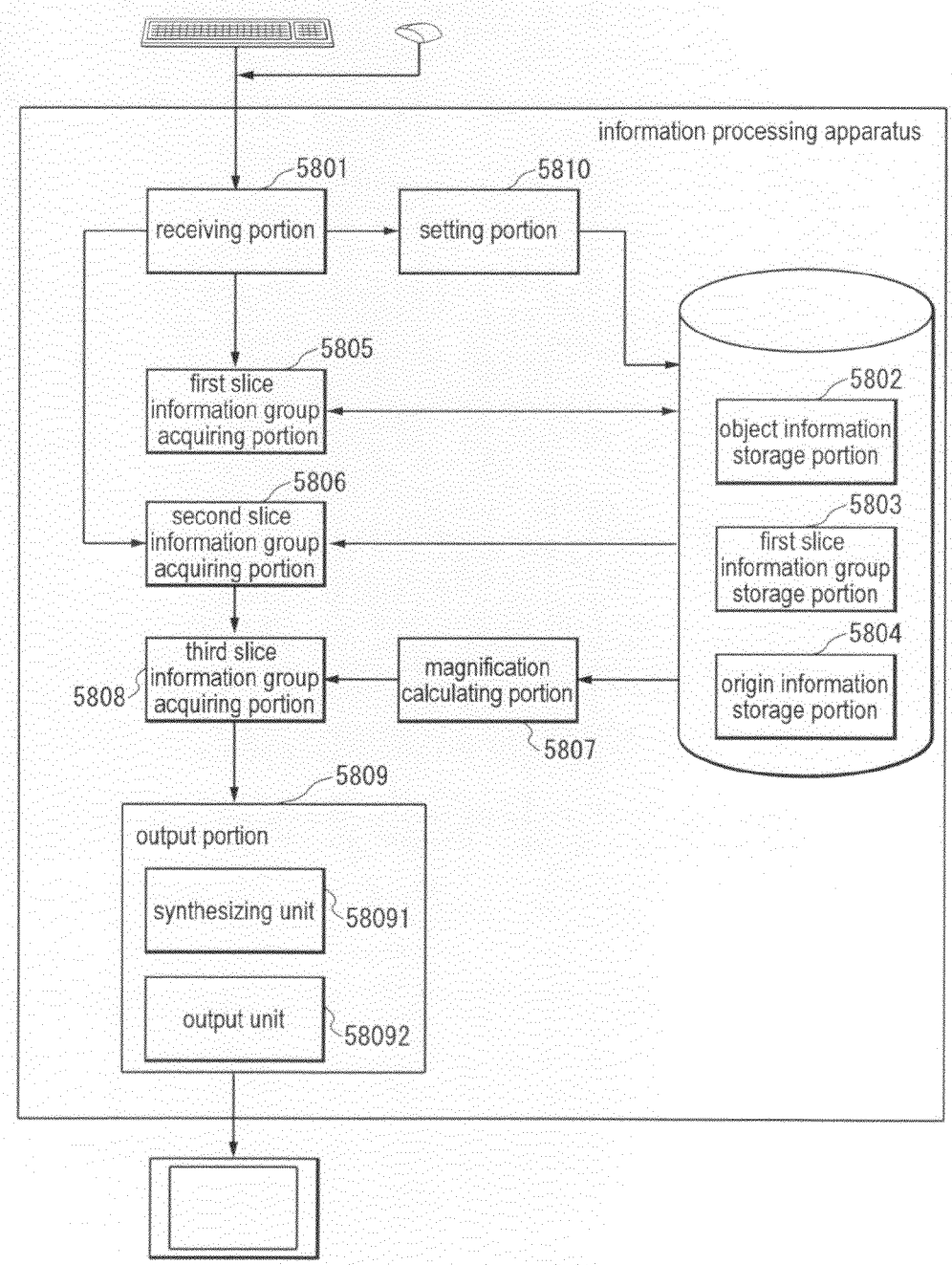
FIG. 58 is a block diagram of an information processing apparatus in Embodiment 6.
Figure 59:
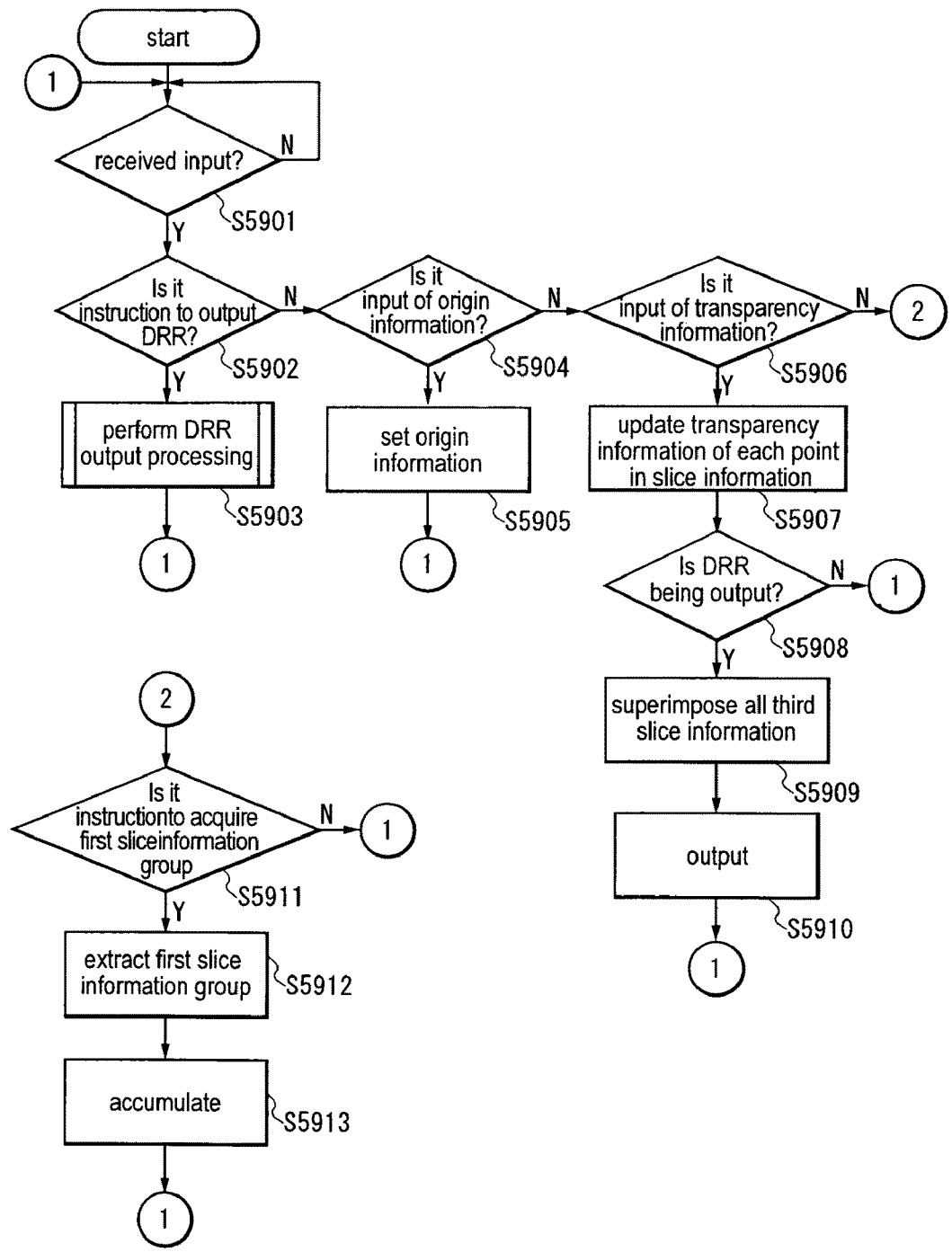
FIG. 59 is a flowchart illustrating the operation of the information processing apparatus.
Figure 60:
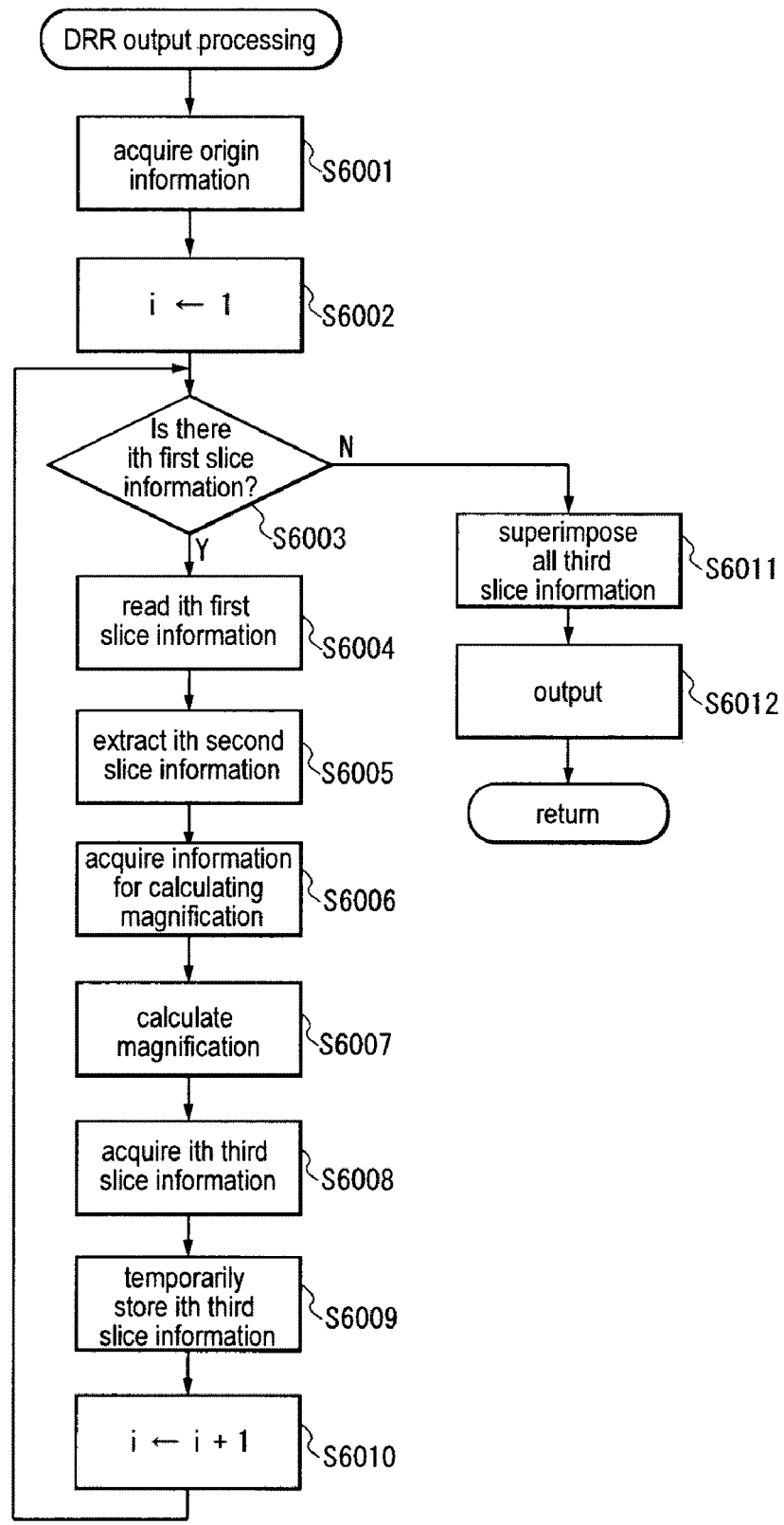
FIG. 60 is a flowchart illustrating processing of outputting a DRR in the information processing apparatus.
Figure 61:
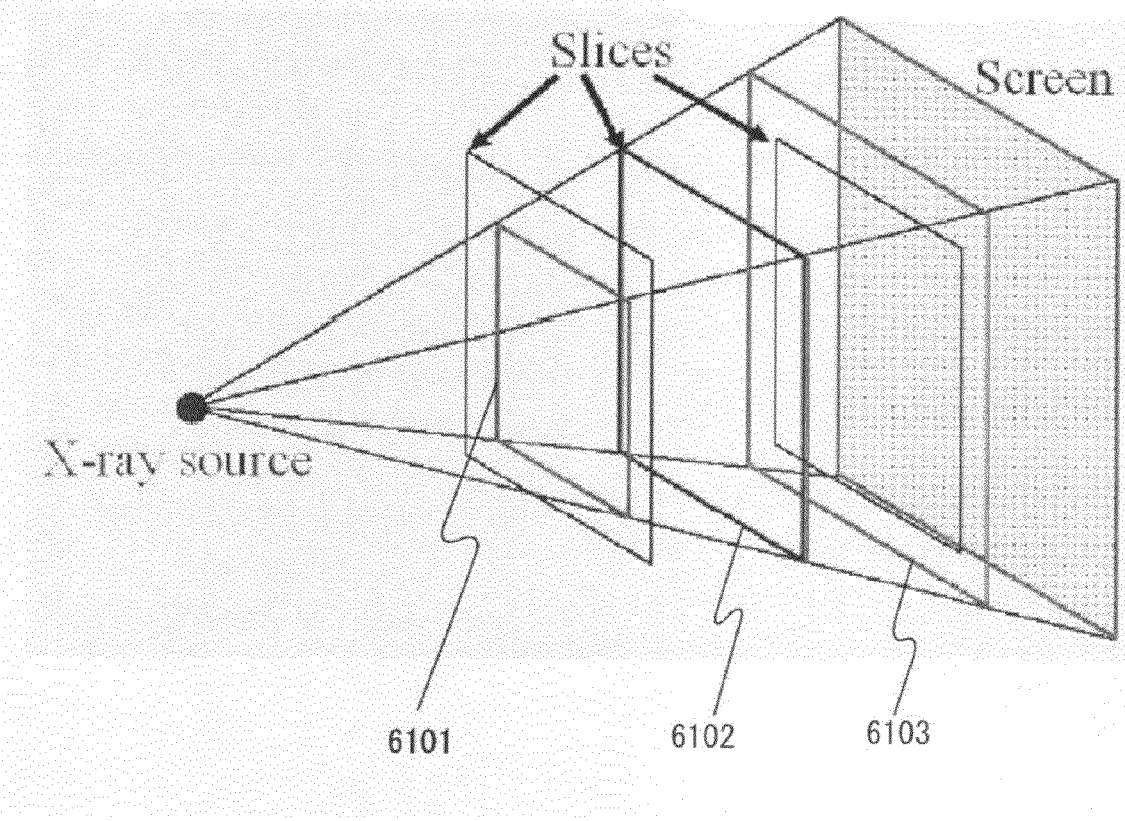
FIG. 61 illustrates a concept of the processing of the information processing apparatus.
Figure 62:
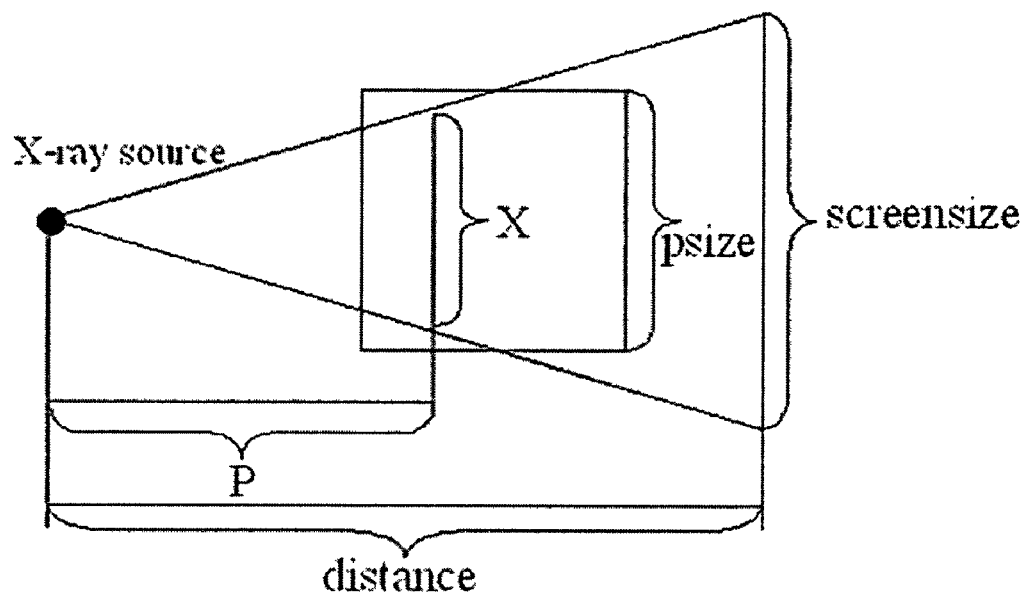
FIG. 62 is a diagram for illustrating an algorithm of magnification calculation in the information processing apparatus.
Figure 63:
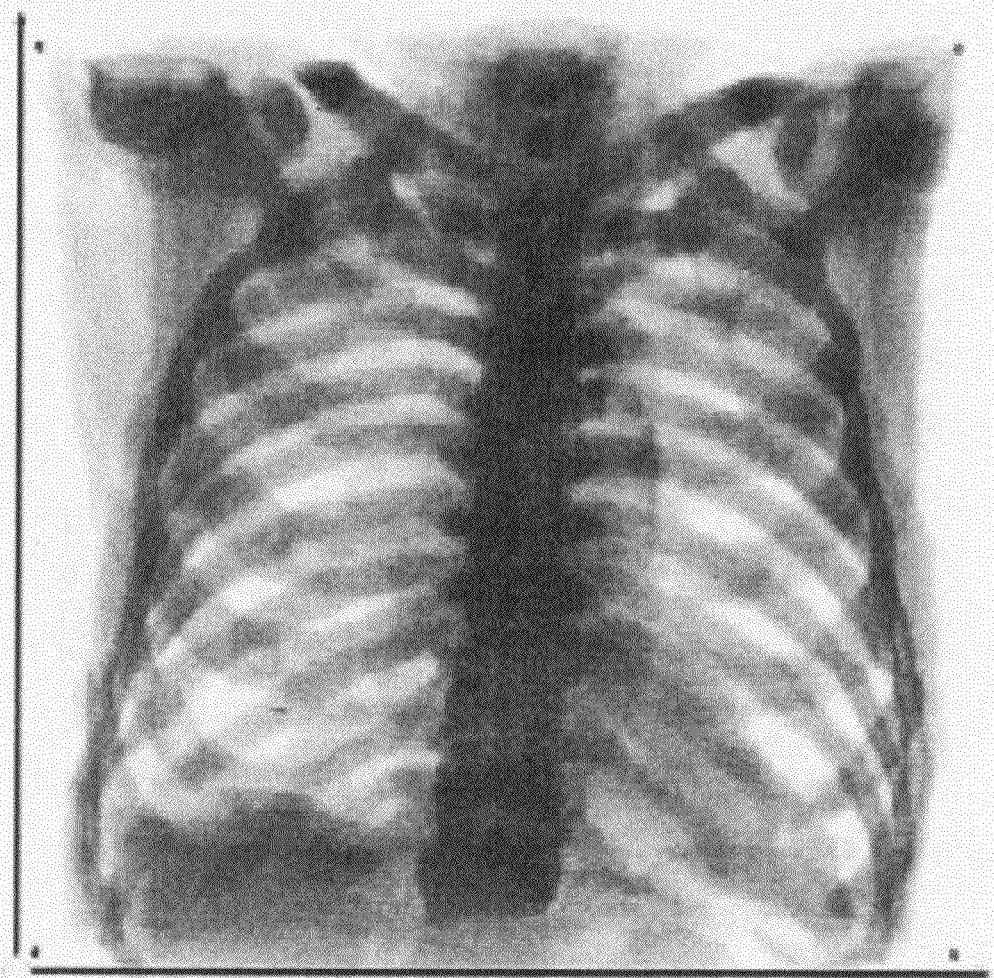
FIG. 63 shows a display example in the information processing apparatus.
Figure 64:
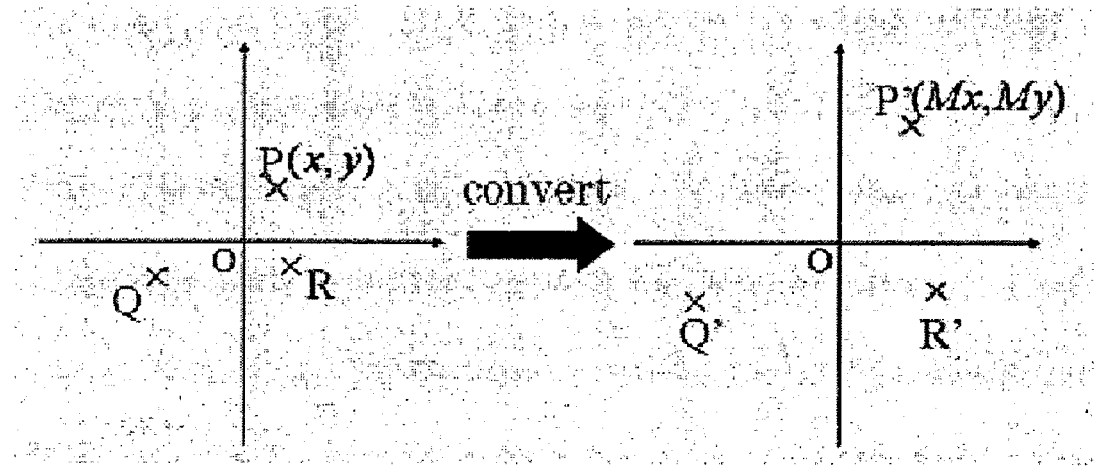
FIG. 64 illustrates coordinate conversion in the information processing apparatus.
Figure 65A:
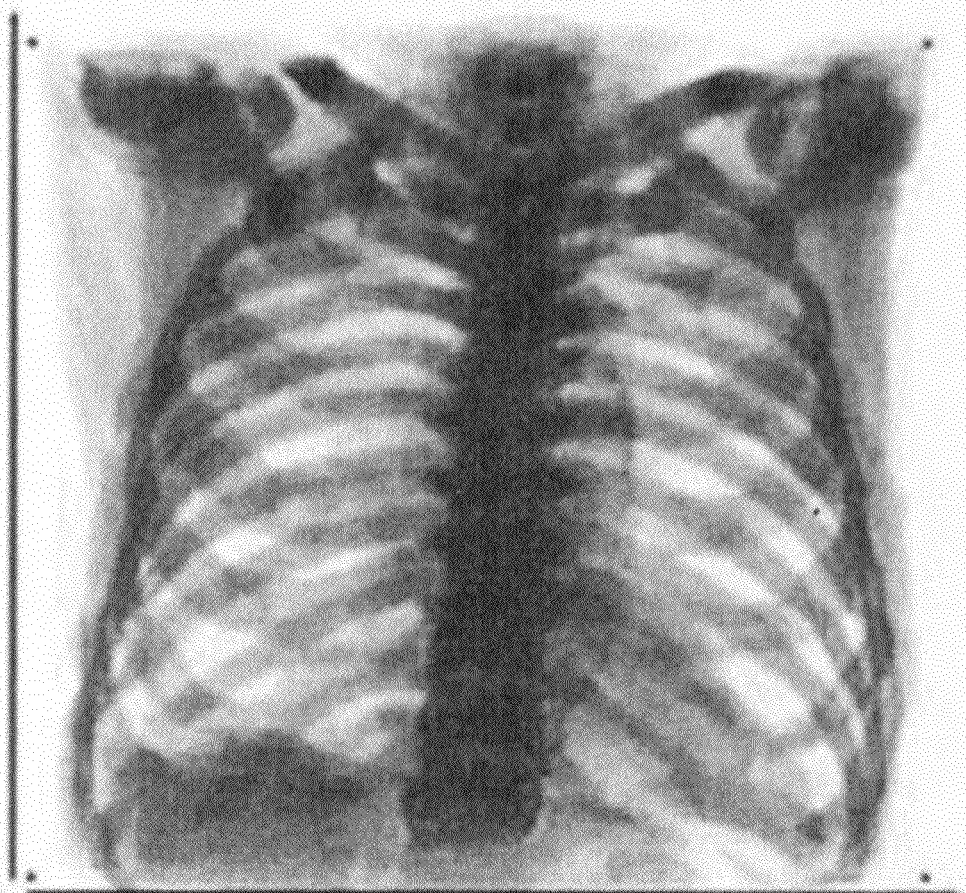
FIG. 65 is a diagram showing output of a deformed DRR in the information processing apparatus.
Figure 66:
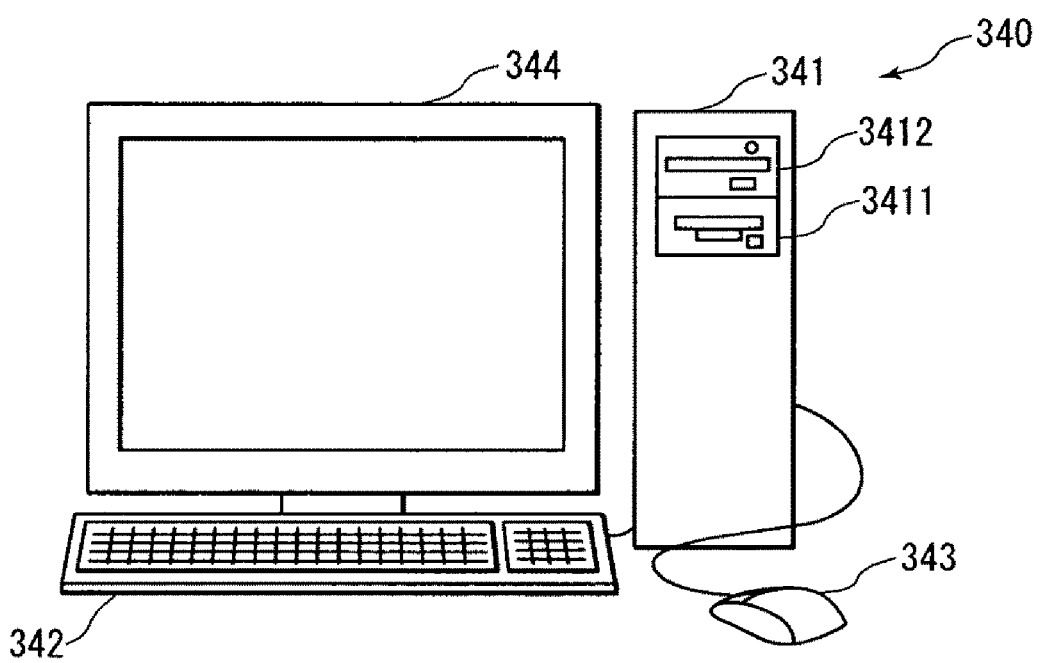
FIG. 66 is a view showing the external appearance of a computer that implements the information processing apparatus.
Figure 67:
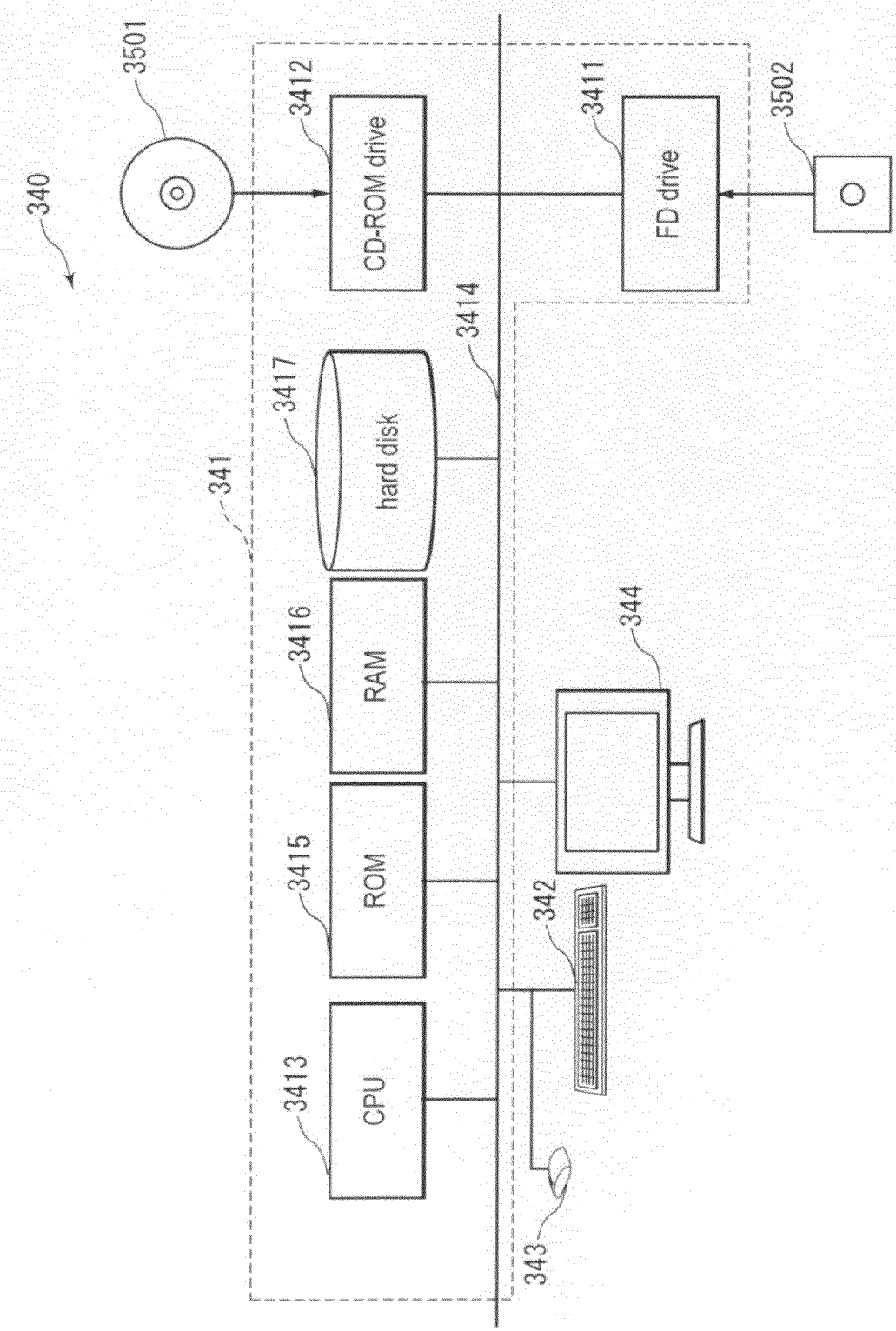
FIG. 67 is a block diagram of a computer system that implements the information processing apparatus

The invention claimed is:

1. An information processing apparatus, comprising:
a slice information group storage portion in which a slice information group having multiple pieces of slice information is stored, the slice information being information constituted based on two-dimensional image data obtained as a result of extraction with multiple planes from 3D voxel information, which is volume texture of a three-dimensional object, and being constituted by information of multiple points having positional information, which is information indicating position, and elasticity information, which is information of elasticity;
a slice information group output portion that outputs the slice information group;
an instruction receiving portion that receives an instruction for a given point or region in the slice information group that has been output;
a positional information acquiring portion that acquirers at least one piece of positional information of the point, or a point constituting the region, corresponding to the instruction;
an elasticity information acquiring portion that acquires at least one piece of elasticity information paired with the at least one piece of positional information that has been acquired by the positional information acquiring portion; and
an elasticity information output portion that performs output based on the at least one piece of elasticity information that has been acquired by the elasticity information acquiring portion,
wherein when the instruction receiving portion receives an instruction for a internal point or internal region of the three-dimensional object:
the positional information acquiring portion acquirers at least one piece of positional information of the internal point, or at least one point constituting the internal region of the three-dimensional object, corresponding to the instruction, and
the elasticity information output portion performs output based on the at least one piece of elasticity information of the internal point, or the point constituting the internal region of the three-dimensional object.

2. The information processing apparatus according to claim 1, further comprising:
an object information storage portion in which 3D voxel information, which is volume texture of a three-dimensional object, is stored; and
a slice information group acquiring portion that extracts multiple pieces of slice information perpendicular to a line of sight and sliced at constant intervals, from the 3D voxel information stored in the object information storage portion, thereby acquiring a slice information group,
wherein the slice information group in the slice information group storage portion is the slice information group that has been acquired by the slice information group acquiring portion.

3. The information processing apparatus according to claim 1, further comprising an input/output portion that inputs an instruction for a given point or region in the slice information group that has been output, and receives output of the elasticity information output portion and outputs a force corresponding to the output.

4. The information processing apparatus according to claim 1, wherein the information of the points contained in the slice information has color information, which is information of color.

5. A program product stored in tangible non-transitory program memory, the program product for causing a computer to execute the steps of:
a slice information group output step of outputting a slice information group having multiple pieces of slice information, the slice information being information constituted based on two-dimensional image data obtained as a result of extraction with multiple planes from 3D voxel information, which is volume texture of a three-dimensional object acquired by capturing with a medical device, and being constituted by information of multiple points having positional information, which is information indicating position, and elasticity information, which is information of elasticity;
an instruction receiving step of receiving an instruction for a given point or region in the slice information group that has been output;
a positional information acquiring step of acquiring at least one piece of positional information of the point, or a point constituting the region, corresponding to the instruction;
an elasticity information acquiring step of acquiring at least one piece of elasticity information paired with the at least one piece of positional information that has been acquired in the positional information acquiring step; and
an elasticity information output step of performing output based on the at least one piece of elasticity information that has been acquired in the elasticity information acquiring step,
wherein when the instruction receiving portion receives an instruction for a internal point or internal region of the three-dimensional object:
a positional information acquiring portion acquirers at least one piece of positional information of the internal point, or at least one point constituting the internal region of the three-dimensional object, corresponding to the instruction, and a elasticity information output portion performs output based on the at least one piece of elasticity information of the internal point, or the point constituting the internal region of the three-dimensional object.

* * * * *